US012766327B2

(12) United States Patent
Van Gerwen et al.

(10) Patent No.: US 12,766,327 B2
(45) Date of Patent: Oct. 20, 2026

(54) INTELLIGENT MODULARIZATION

(71) Applicant: Cochlear Limited, Macquarie University (AU)

(72) Inventors: Peter Bart Jos Van Gerwen, Mechelen (BE); James Roy Easter, Lyons, CO (US)

(73) Assignee: Cochlear Limited, Macquarie University (AU)

( * ) Notice: Subject to any disclaimer, the term of this patent is extended or adjusted under 35 U.S.C. 154(b) by 605 days.

(21) Appl. No.: 15/224,755

(22) Filed: Aug. 1, 2016

(65) Prior Publication Data

US 2018/0028811 A1 Feb. 1, 2018

(51) Int. Cl.
*A61N 1/36* (2006.01)
*A61N 1/372* (2006.01)

(52) U.S. Cl.
CPC ....... *A61N 1/37252* (2013.01); *A61N 1/3603* (2017.08); *A61N 1/36036* (2017.08); *A61N 1/36038* (2017.08)

(58) Field of Classification Search
CPC ... A61N 1/3603; A61N 1/3608; A61N 1/3606
See application file for complete search history.

(56) References Cited

U.S. PATENT DOCUMENTS

| | | | |
|---|---|---|---|
| 3,875,349 | A | 4/1975 | Ruegg |
| 4,443,666 | A | 4/1984 | Cote |
| 4,450,930 | A | 5/1984 | Killion |
| 4,504,703 | A | 3/1985 | Schneiter et al. |
| 4,532,930 | A | 8/1985 | Crosby et al. |
| 4,606,329 | A | 8/1986 | Hough |
| 4,607,383 | A | 8/1986 | Ingalls |
| 4,621,171 | A | 11/1986 | Wada et al. |
| 4,774,933 | A | 10/1988 | Hough et al. |
| 4,815,560 | A | 3/1989 | Madaffari |
| 4,837,833 | A | 6/1989 | Madaffari |
| RE33,170 | E | 2/1990 | Byers |

(Continued)

FOREIGN PATENT DOCUMENTS

| | | | |
|---|---|---|---|
| WO | 0191678 | A1 | 12/2001 |
| WO | 2004024212 | A1 | 3/2004 |

(Continued)

OTHER PUBLICATIONS

W. West et al., "The Design of a Loud-Speaker," I.E.E. Wireless Proceedings, vol. 15, No. 44, Jun. 1940, pp. 4 and 54-67.

(Continued)

*Primary Examiner* — Jennifer Pitrak McDonald
*Assistant Examiner* — Jennifer L Ghand
(74) *Attorney, Agent, or Firm* — Pilloff Passino & Cosenza LLP; Martin J. Cosenza

(57) ABSTRACT

An implantable device, including an implantable module including a first functional component, the implantable module being configured to effectively differentiate between a plurality of different second modules respectively placeable into signal communication with the module. In an exemplary embodiment, the implantable module is configured to analyze respective signals from the plurality of different second modules and determine a respective functionality of the second modules based on the respective signals.

20 Claims, 47 Drawing Sheets

(56) References Cited

U.S. PATENT DOCUMENTS

| | | | | |
|---|---|---|---|---|
| 4,932,405 | A | 6/1990 | Peeters et al. | |
| 4,936,305 | A | 6/1990 | Ashtiani et al. | |
| 5,015,224 | A | 5/1991 | Maniglia | |
| 5,105,811 | A | 4/1992 | Kuzma | |
| 5,163,957 | A | 11/1992 | Sadéet al. | |
| 5,176,620 | A | 1/1993 | Gilman | |
| 5,276,739 | A | 1/1994 | Krokstad et al. | |
| 5,277,694 | A | 1/1994 | Leysieffer et al. | |
| 5,363,452 | A | 11/1994 | Anderson | |
| 5,411,467 | A | 5/1995 | Hortmann et al. | |
| 5,411,537 | A * | 5/1995 | Munshi | A61N 1/3708 607/33 |
| 5,456,654 | A | 10/1995 | Ball | |
| 5,554,096 | A | 9/1996 | Ball | |
| 5,558,618 | A | 9/1996 | Maniglia | |
| 5,624,376 | A | 4/1997 | Ball et al. | |
| 5,702,431 | A | 12/1997 | Wang et al. | |
| 6,039,685 | A | 3/2000 | Bushek | |
| 6,067,474 | A | 5/2000 | Schulman et al. | |
| 6,272,382 | B1 | 8/2001 | Faltys et al. | |
| 6,308,101 | B1 * | 10/2001 | Faltys | A61N 1/375 607/57 |
| 6,325,755 | B1 | 12/2001 | Bushek et al. | |
| 6,482,144 | B1 | 11/2002 | Müller | |
| 6,517,476 | B1 | 2/2003 | Bedoya et al. | |
| 6,554,761 | B1 | 4/2003 | Puria et al. | |
| 6,556,870 | B2 | 4/2003 | Zierhofer et al. | |
| 6,648,914 | B2 | 11/2003 | Berrang et al. | |
| 6,786,860 | B2 | 9/2004 | Maltan et al. | |
| 6,807,445 | B2 | 10/2004 | Baumann et al. | |
| 7,197,152 | B2 | 3/2007 | Miller et al. | |
| 7,204,799 | B2 | 4/2007 | Miller, III et al. | |
| 7,204,800 | B2 | 4/2007 | Easter et al. | |
| 7,214,179 | B2 | 5/2007 | Miller et al. | |
| 7,354,394 | B2 | 4/2008 | Slattery et al. | |
| 7,489,793 | B2 | 2/2009 | Miller, III et al. | |
| 7,522,738 | B2 | 4/2009 | Miller, III | |
| 7,556,597 | B2 | 7/2009 | Miller, III et al. | |
| 7,775,964 | B2 | 8/2010 | Miller, III | |
| 7,822,479 | B2 | 10/2010 | Stracener | |
| 7,840,020 | B1 | 11/2010 | Miller, III et al. | |
| 8,550,977 | B2 | 10/2013 | Kasic, II et al. | |
| 8,626,308 | B2 | 1/2014 | Meskens | |
| 8,657,734 | B2 | 2/2014 | Parker | |
| 8,771,166 | B2 | 7/2014 | Conn | |
| 10,646,709 | B2 | 5/2020 | Mazanec et al. | |
| 10,994,129 | B2 | 5/2021 | Roehrlein et al. | |
| 2002/0032401 | A1 | 3/2002 | Fereira et al. | |
| 2003/0031336 | A1 | 2/2003 | Harrison et al. | |
| 2003/0055311 | A1 | 3/2003 | Neukermans et al. | |
| 2005/0005421 | A1 | 1/2005 | Wang et al. | |
| 2005/0101832 | A1 | 5/2005 | Miller, III et al. | |
| 2006/0183965 | A1 | 8/2006 | Kasic, II et al. | |
| 2007/0016267 | A1 | 1/2007 | Griffin et al. | |
| 2007/0167671 | A1 | 7/2007 | Miller, III | |
| 2007/0217640 | A1 | 9/2007 | Maltan et al. | |
| 2007/0280495 | A1 | 12/2007 | Abolfathi | |
| 2008/0049953 | A1 | 2/2008 | Harney et al. | |
| 2008/0085023 | A1 | 4/2008 | Kulkarni et al. | |
| 2008/0132750 | A1 | 6/2008 | Miller | |
| 2008/0167516 | A1 | 7/2008 | Jaeger et al. | |
| 2008/0234539 | A1 | 9/2008 | Slattery et al. | |
| 2009/0163978 | A1 | 6/2009 | Miller, III et al. | |
| 2009/0187065 | A1 | 7/2009 | Basinger | |
| 2009/0198146 | A1 * | 8/2009 | Gerber | A61B 5/0031 600/549 |
| 2009/0216296 | A1 * | 8/2009 | Meskens | A61N 1/36036 607/57 |
| 2010/0272287 | A1 | 10/2010 | Miller, III | |
| 2010/0317913 | A1 | 12/2010 | Conn et al. | |
| 2011/0034755 | A1 | 2/2011 | Parker | |
| 2011/0087325 | A1 * | 4/2011 | Van Baelen | A61N 1/36036 623/10 |
| 2011/0218605 | A1 * | 9/2011 | Cryer | A61N 1/0541 607/137 |
| 2011/0264155 | A1 | 10/2011 | Van den Heuvel et al. | |
| 2012/0041515 | A1 | 2/2012 | Meskens et al. | |
| 2012/0109297 | A1 * | 5/2012 | Van den Heuvel | A61F 2/18 623/10 |
| 2013/0079844 | A1 | 3/2013 | Conn et al. | |
| 2014/0316190 | A1 | 10/2014 | Conn et al. | |
| 2015/0380972 | A1 * | 12/2015 | Fort | H02J 50/402 320/108 |
| 2016/0199644 | A1 * | 7/2016 | Van den Heuvel | A61N 1/36038 607/57 |
| 2018/0333577 | A1 * | 11/2018 | Nygard | A61N 1/36039 |

FOREIGN PATENT DOCUMENTS

| | | | |
|---|---|---|---|
| WO | 2006081361 | A1 | 8/2006 |
| WO | 2009117767 | A1 | 10/2009 |
| WO | 2010126996 | A1 | 11/2010 |

OTHER PUBLICATIONS

C. Gibbons et al., "Design of a Biomimetic Directional Microphone Diaphragm," Proceedings of International Mechanical Engineering Congress and Exposition, Nov. 5-10, 2000, Orlando, FL, pp. 1-7.

A. Rens Leeuw et al., "Advantages of Directional Hearing Aid Microphones Related to Room Acoustics," Audiology, Jan. 1991, 30: 330-344.

Specification sheet for beyerdynamic MCE 60 Condenser Microphone, pp. 1-2, accessible on line at http://northamerica.beyerdynamic.com/shop/mce-60-09-cable-with-free-ends-4.html, available Feb. 21, 2009.

* cited by examiner

INTELLIGENT MODULARIZATION

BACKGROUND

Hearing loss is generally of two types, conductive and sensorineural. Sensorineural hearing loss is due to the absence or destruction of the cochlear hair cells which transduce sound into nerve impulses. Various hearing prostheses have been developed to provide individuals suffering from sensorineural hearing loss with the ability to perceive sound. For example, cochlear implants have an electrode assembly which is implanted in the cochlea. In operation, electrical stimuli are delivered to the auditory nerve via the electrode assembly, thereby bypassing the inoperative hair cells to cause a hearing percept.

Conductive hearing loss occurs when the natural mechanical pathways that provide sound in the form of mechanical energy to cochlea are impeded, for example, by damage to the ossicular chain or ear canal. For a variety of reasons, such individuals are typically not candidates for a cochlear implant. Rather, individuals suffering from conductive hearing loss typically receive an acoustic hearing aid. Hearing aids rely on principles of air conduction to transmit acoustic signals to the cochlea. In particular, hearing aids amplify received sound and transmit the amplified sound into the ear canal. This amplified sound reaches the cochlea in the form of mechanical energy, causing motion of the perilymph and stimulation of the auditory nerve.

Unfortunately, not all individuals suffering from conductive hearing loss are able to derive suitable benefit from hearing aids. For example, some individuals are prone to chronic inflammation or infection of the ear canal. Other individuals have a malformed or absent outer ear and/or ear canals resulting from a birth defect, or as a result of medical conditions such as Treacher Collins syndrome or Microtia.

For these and other individuals, another type of hearing prosthesis has been developed in recent years. This hearing prosthesis, commonly referred to as a middle ear implant, converts received sound into a mechanical force that is applied to the ossicular chain or directly to the cochlea via an actuator implanted in or adjacent to the middle ear cavity.

SUMMARY

In accordance with an exemplary embodiment, there is an implantable device, comprising an implantable module including a first functional component, the implantable module being configured to effectively differentiate between a plurality of different second modules respectively placeable into signal communication with the module.

In accordance with another exemplary embodiment, there is a method comprising operating an implantable component as part of a partially implantable prosthesis based on a first received signal received by the implantable component, and automatically operating the implantable component as part of a fully implantable prosthesis based on a second received signal received by the implantable component.

In accordance with an exemplary embodiment, there is an implantable system, comprising a first implantable module having a first role in the implantable system, wherein the first implantable module is configured to adopt a second role automatically upon a changed circumstance.

BRIEF DESCRIPTION OF THE DRAWINGS

Embodiments are described below with reference to the attached drawings, in which.

DETAILED DESCRIPTION

Figure 1:
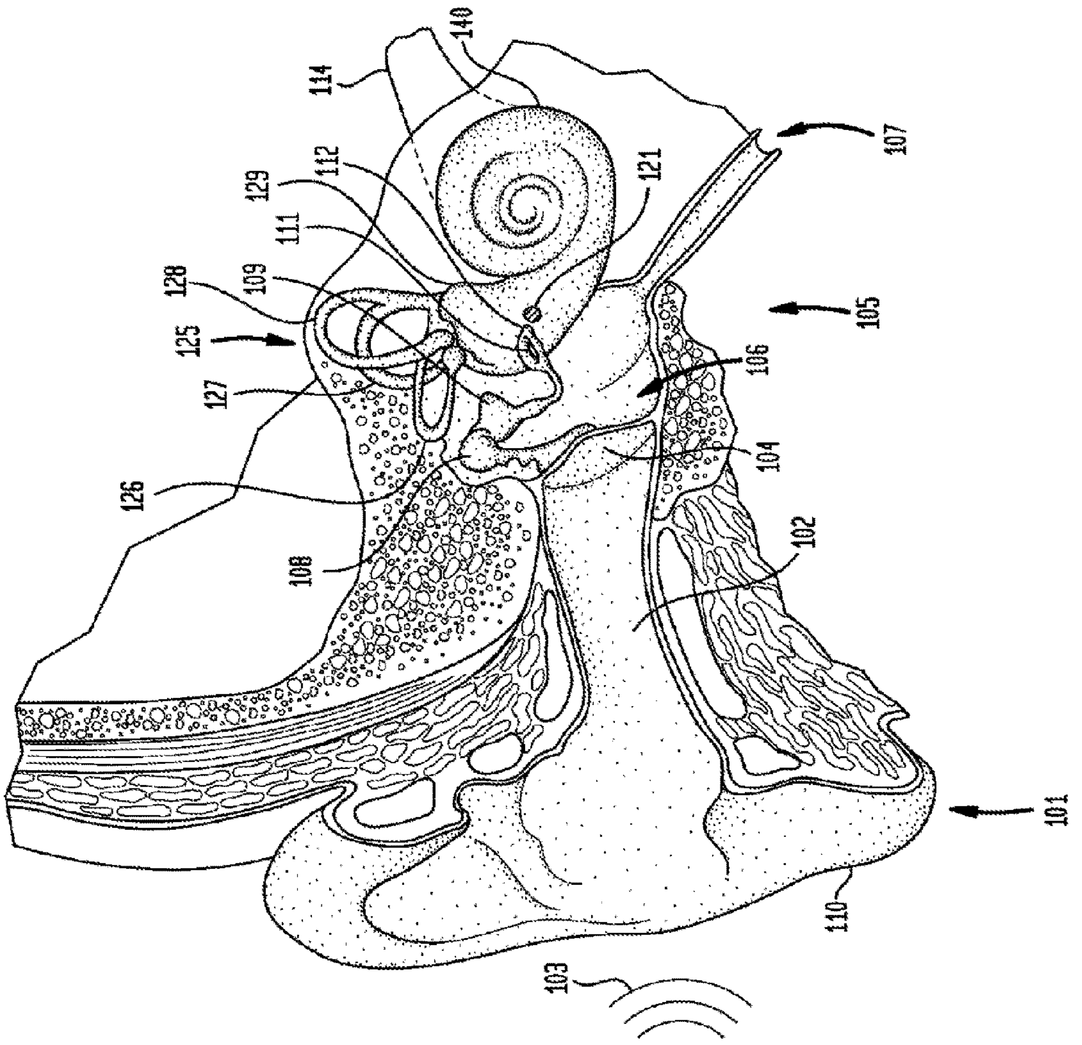
FIG. 1 is a perspective view of an ear system of a recipient.

FIG. 1 is a perspective view of a human skull showing the anatomy of the human ear. As shown in FIG. 1, the human ear comprises an outer ear 101, a middle ear 105, and an inner ear 107. In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112, which is adjacent round window 121. This vibration is coupled through three bones of middle ear 105, collectively referred to as the ossicles 106 and comprising the malleus 108, the incus 109, and the stapes 111. Bones 108, 109, and 111 of middle ear 105 serve to filter and amplify sound wave 103, causing oval window 112 to articulate, or vibrate in response to the vibration of tympanic membrane 104. This vibration sets up waves of fluid motion of the perilymph within cochlea 140. Such fluid motion, in turn, activates hair cells (not shown) inside cochlea 140. Activation of the hair cells causes nerve impulses to be generated and transferred through the spiral ganglion cells (not shown) and auditory nerve 114 to the brain (also not shown) where they cause a hearing percept.

As shown in FIG. 1, semicircular canals 125 are three half-circular, interconnected tubes located adjacent cochlea 140. Vestibule 129 provides fluid communication between semicircular canals 125 and cochlea 140. The three canals are the horizontal semicircular canal 126, the posterior semicircular canal 127, and the superior semicircular canal 128. The canals 126, 127, and 128 are aligned approximately orthogonally to one another. Specifically, horizontal canal 126 is aligned roughly horizontally in the head, while the superior 128 and posterior canals 127 are aligned roughly at a 45 degree angle to a vertical through the center of the individual's head.

Each canal is filled with a fluid called endolymph and contains a motion sensor with tiny hairs (not shown) whose ends are embedded in a gelatinous structure called the cupula (also not shown). As the orientation of the skull changes, the endolymph is forced into different sections of the canals. The hairs detect when the endolymph passes thereby, and a signal is then sent to the brain. Using these hair cells, horizontal canal 126 detects horizontal head movements, while the superior 128 and posterior 127 canals detect vertical head movements.

Figure 2A:
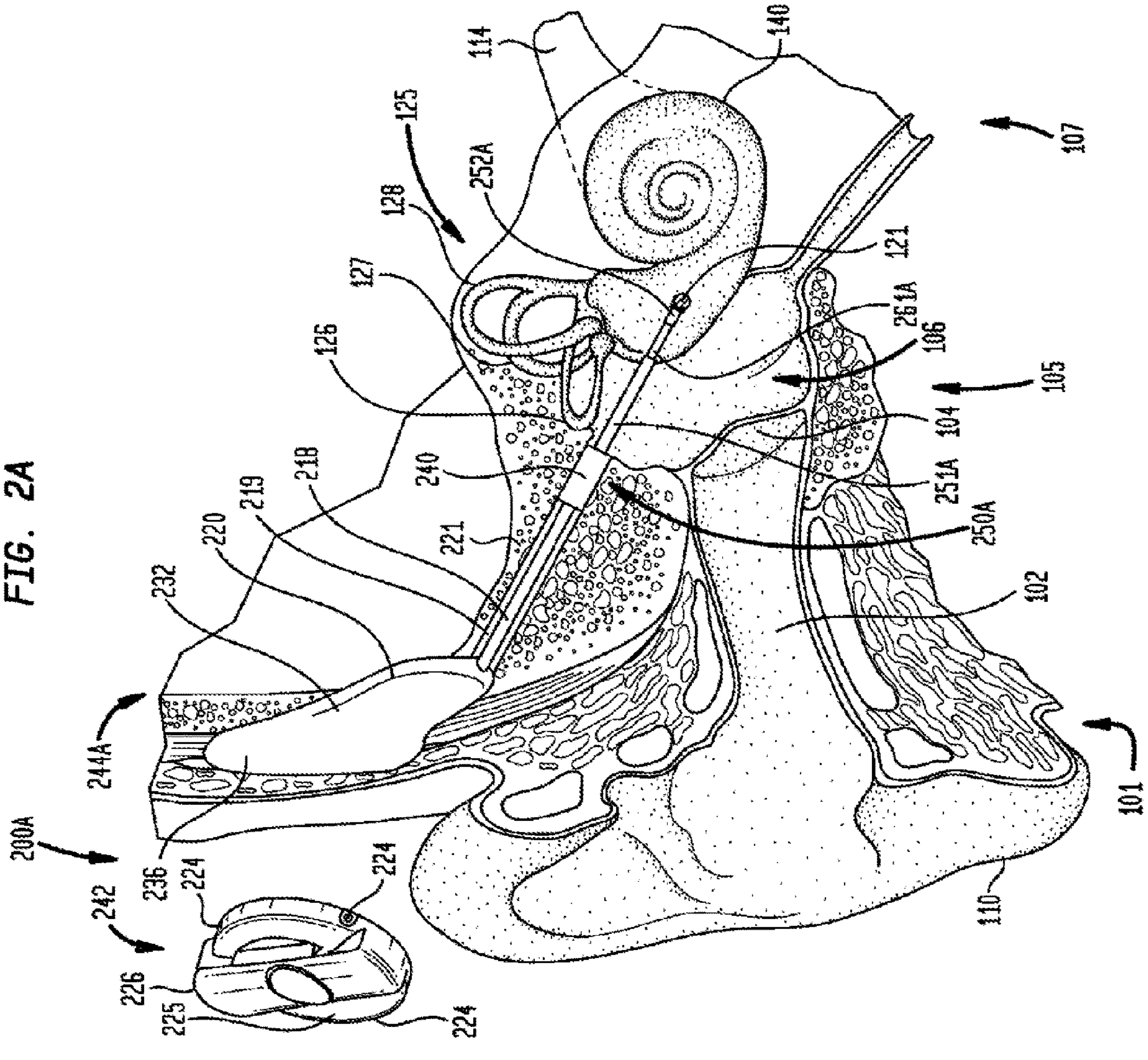
FIG. 2A is a perspective view of an exemplary hearing prosthesis in which at least some of the teachings detailed herein are applicable.

FIG. 2A is a perspective view of an exemplary direct acoustic cochlear stimulator 200A in accordance with an exemplary embodiment. Direct acoustic cochlear stimulator 200A comprises an external component 242 that is directly or indirectly attached to the body of the recipient, and an internal component 244A that is temporarily or permanently implanted in the recipient. External component 242 typically comprises two or more sound input elements, such as microphones 224 for detecting sound, a sound processing unit 226, a power source (not shown), and an external transmitter unit 225. External transmitter unit 225 comprises an external coil (not shown). Sound processing unit 226 processes the output of microphones 224 and generates encoded data signals which are provided to external transmitter unit 225. For ease of illustration, sound processing unit 226 is shown detached from the recipient.

Internal component 244A comprises an internal receiver/transmitter unit (hereinafter referred to as a communications unit) 232 including an inductance coil portion 236 (which is made, in some embodiments, out of silicone in which platinum coils (not shown) are embedded) and a stimulator unit 220, and a stimulation arrangement 250A in electrical communication with stimulator unit 220 via cable 218 extending through artificial passageway 219 in mastoid bone 221. Internal communications unit 232 and stimulator unit 220 are hermetically sealed within a biocompatible housing, and are sometimes collectively referred to as a stimulator/communications unit.

Internal communications unit 232 comprises an internal coil (not shown), and optionally, a magnet (also not shown) fixed relative to the internal coil. The external coil transmits electrical signals (i.e., power and stimulation data) to the internal coil via a radio frequency (RF) link. The internal coil is typically a wire antenna coil comprised of multiple turns of electrically insulated platinum or gold wire. The electrical insulation of the internal coil is provided by a flexible silicone molding (not shown). In use, implantable communications unit 232 is positioned in a recess of the temporal bone adjacent auricle 110.

In the illustrative embodiment of FIG. 2A, ossicles 106 have been explanted. However, it should be appreciated that stimulation arrangement 250A may be implanted without disturbing ossicles 106.

Stimulation arrangement 250A comprises an actuator 240, a middle ear prosthesis 252A and a coupling element 251A which includes an artificial incus 261B (represented in a quasi-functional manner—some additional details of these components are described below). Actuator 240 is coupled to mastoid bone 221 so as to be held in the interior of artificial passageway 219 formed in mastoid bone 221.

In this embodiment, stimulation arrangement 250A is implanted and/or configured such that a portion of middle ear prosthesis 252A abuts the round window 121. In an alternate embodiment, the middle ear prosthesis 252A can abut the oval window (not shown). In some alternate embodiments, stimulation arrangement 250B may alternatively be implanted such that the middle ear prosthesis 252A abuts an opening in horizontal semicircular canal 126, in posterior semicircular canal 127 or in superior semicircular canal 128. Any attachment regime that can enable a hearing percept to be evoked utilizing the stimulation arrangement 250A can be utilized.

As noted above, a sound signal is received by microphone(s) 224, processed by sound processing unit 226, and transmitted as encoded data signals to internal communications 232. Based on these received signals, stimulator unit 220 (sometimes referred to herein as a driver or driver unit) generates drive signals which cause actuation of actuator 240. The mechanical motion of actuator 240 is transferred to middle ear prosthesis 252A such that a wave of fluid motion is generated in the perilymph in the scala tympani of the cochlea. Such fluid motion, in turn, activates the hair cells of the organ of Corti. Activation of the hair cells causes appropriate nerve impulses to be generated and transferred through the spiral ganglion cells (not shown) and auditory nerve 114 to cause a hearing percept in the brain.

Figure 2B:
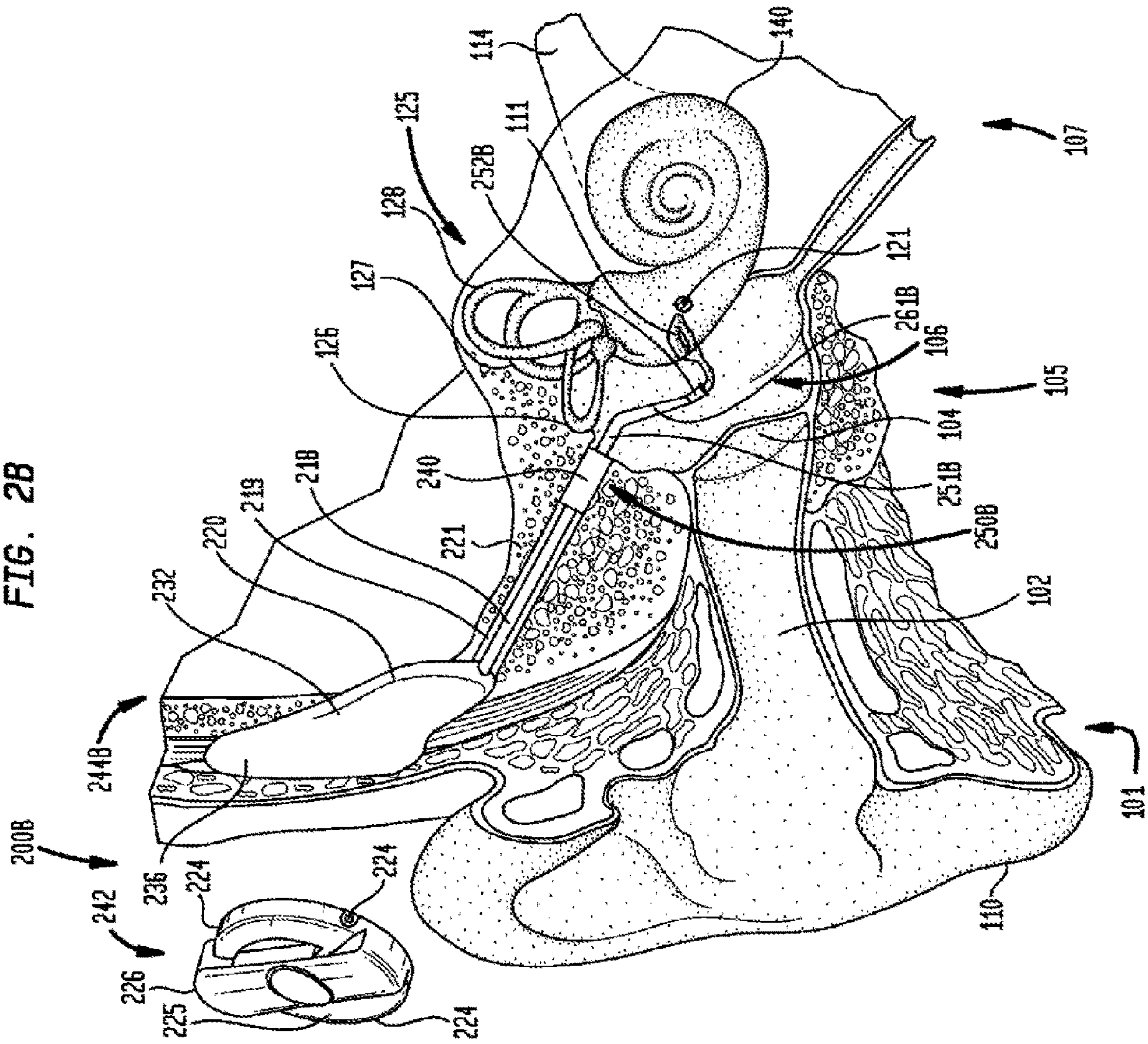
FIG. 2B is a perspective view of another exemplary hearing prosthesis in which at least some of the teachings detailed herein are applicable.

FIG. 2B depicts an exemplary embodiment of a middle ear implant 200B having a stimulation arrangement 250B comprising actuator 240 and a coupling element 251B. Coupling element 251B includes an ossicular replacement prosthesis or middle ear prosthesis 252B and an artificial incus 261B which couples the actuator to the middle ear prosthesis. In this embodiment, middle ear prosthesis 252B abuts stapes 111.

Figure 3:
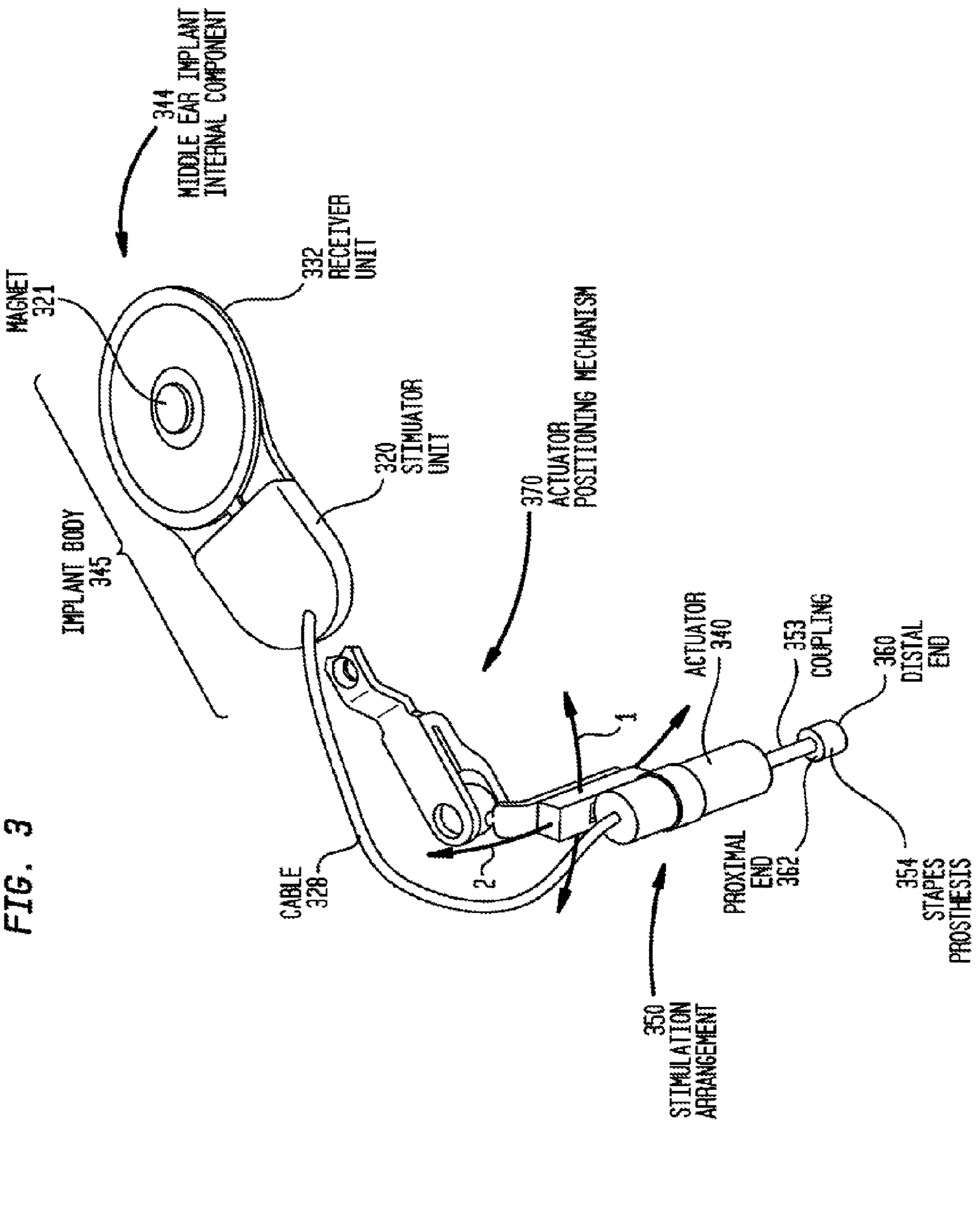
FIG. 3 is a perspective view of an exemplary implantable component of an exemplary hearing prosthesis in which at least some teachings detailed herein are applicable.

FIG. 3 is a perspective view of an exemplary internal component 344 of a middle ear implant in the form of a direct extra cochlear acoustic stimulator according to an exemplary embodiment. Internal component 344 comprises an internal communications unit 332, a stimulator unit 320, a stimulation arrangement 350, and an actuator positioning mechanism 370. As shown, communications unit 332 comprises an internal coil (not shown), and in some embodiments, a magnet 321 fixed relative to the internal coil. Internal communications unit 332 and stimulator unit 320 are typically hermetically sealed within a biocompatible housing. This housing has been omitted from FIG. 3 for ease of illustration, and hence the end of the actuator positioning mechanism 370, discussed in more detail below, which connects to the housing, is depicted with broken lines. Collectively, the internal communications unit 332, the stimulator unit 320 and the housing form an implant body 345.

Stimulator unit 320 is connected to stimulation arrangement 350 via a cable 328. Stimulation arrangement 350 comprises an actuator 340, a middle ear prosthesis 354, and a coupling element 353. A distal end of middle ear prosthesis 354 is configured to be positioned in one or more of the configurations noted above with respect to FIGS. 2A-2B. A proximal end of middle ear prosthesis 354 is connected to actuator 340 via coupling element 353 and the distal end of the prosthesis is directly or indirectly coupled to the cochlea. In operation, actuator 340 vibrates middle ear prosthesis 354. The vibration of middle ear prosthesis 354 generates waves of fluid motion of the perilymph, thereby activating the hair cells of the organ of Corti. Activation of the hair cells causes appropriate nerve impulses to be generated and transferred through the spiral ganglion cells and auditory nerve 114.

Middle ear implant internal component 344 further includes actuator positioning mechanism 370. As may be seen, actuator positioning mechanism 370 is connected to and extends from implantable body 345 and is configured to removably receive actuator 340.

Figure 4:
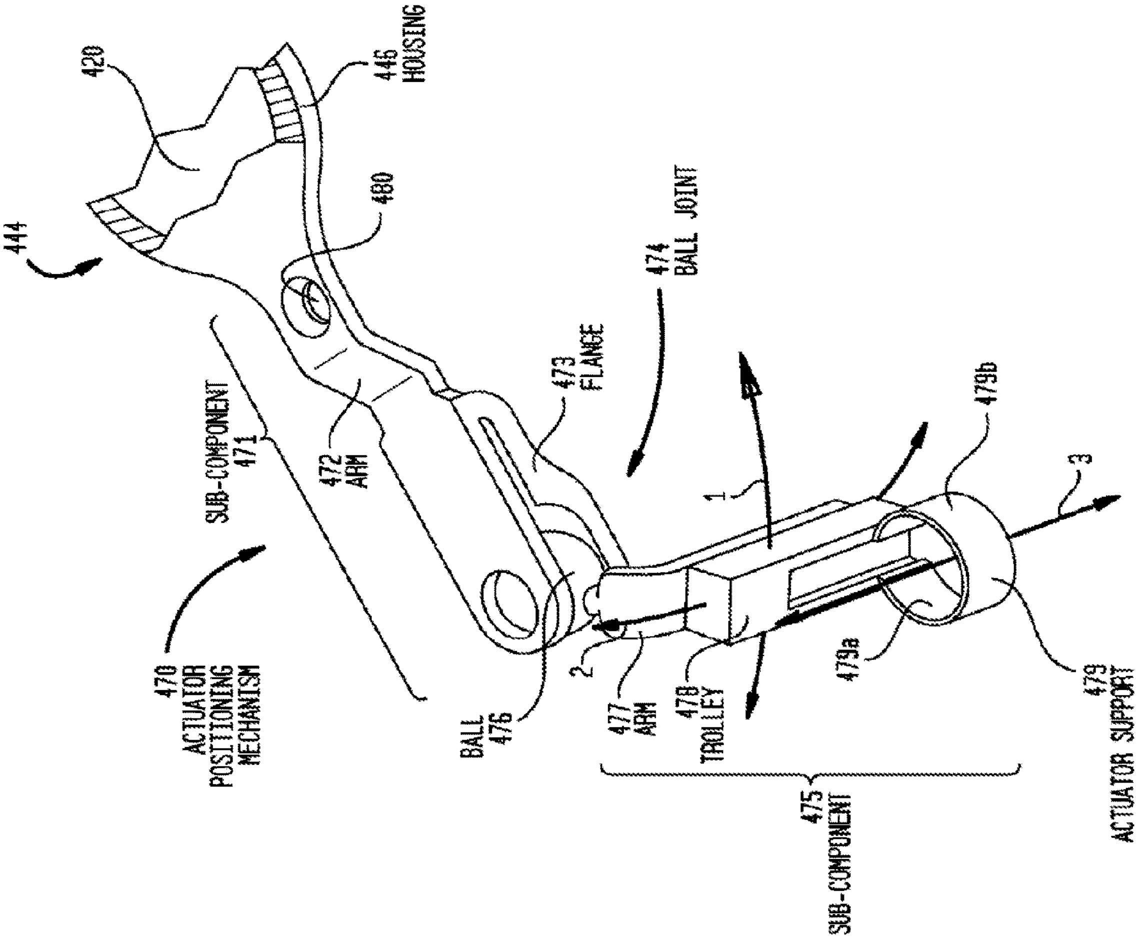
FIG. 4 is a perspective view of a component of the implantable component of FIG. 3.

FIG. 4 depicts actuator positioning mechanism 470 as comprising two sub-components: extension arm 471 and extension arm 475. Sub-component 471 includes arm 472 which is an integral part of housing 446 (where the cross-hatching of housing 446 seen in FIG. 4 corresponds to the wall of the housing, as will be described in greater detail below). In an exemplary embodiment, arm 472 may be part of the same casting forming at least part of housing 446 (i.e., the arm 472 and at least a portion of the housing 446 form a monolithic component), although in an alternate exemplary embodiment, arm 472 may be a separate component that is attached to the housing 446 (e.g., via laser welding). In an exemplary embodiment, the casting may be made partially or totally out of titanium. In this regard, it is noted that the actuator support mechanism may be made partially or totally out of titanium, and the housing 446 may be made out of a different material. Sub-component 471 also includes flange 473 which forms a female portion of ball joint 474. In this regard, sub-component 475 includes the male portion of the ball joint 474, in the form of a ball 476, as may be seen. Ball joint 474 permits the ball 476 of sub-component 475 to move within the female portion, thereby permitting sub-component 475 to articulate relative to sub-component 471, and thus permitting actuator 340 to likewise articulate relative to middle ear implant internal component 344.

Ball joint 474 enables the actuator 340 to be positioned at an adjustably fixed location relative to the implantable body 345. In an exemplary embodiment, the ball joint 474 permits the location of the actuator 340 to be adjustable relative to the implant body in two degrees of freedom, represented by arrows 1 and 2 (first and second degrees of freedom, respectively), in FIGS. 3 and 4, although in some embodiments the joint may permit the location of the actuator 340 to be adjustable relative to the implant body in only one degree of freedom or in more than two degrees of freedom.

While actuator positioning mechanism 470 is depicted with a ball joint 474, other types of joints may be utilized. By way of example, the joint may comprise a malleable portion of a structural component of the actuator positioning mechanism 470 that permits the actuator 340 to be positioned, as just detailed or variations thereof. In an exemplary embodiment, the joint is an elastically deformable portion or plastically deformable portion, or is a combination of elastically deformable and plastically deformable portions so as to enable the adjustment of the location of the received actuator relative to the implant body in the at least one degree of freedom.

As noted above, actuator positioning mechanism 470 further includes sub-component 475. Sub-component 475 comprises ball 476 of ball joint 474, arm 477, trolley 478, and actuator support 479. Actuator support 479 is depicted as being in the form of a collar, and receives and otherwise holds actuator 340 therein, and thus holds the actuator 340 to the actuator positioning mechanism 470.

The collar has an exterior surface 479A and an interior surface 479B, configured to receive actuator 340. The interior diameter of the collar, formed by interior surface 479B is approximately the same as the outer diameter of the cylindrical body of actuator 340. The outer diameter of the collar, formed by exterior surface 479A, is sized such that the collar will fit into the artificial passageway 219. The length of the collar is shorter than the cylindrical body of the actuator 340, but in other embodiments, it may be the same length or about the same length or longer.

As noted, actuator support 479 and actuator 340 are configured to enable the actuator 340 to be removably secured to the actuator support 479, and thus the actuator positioning mechanism 470. This removable securement may be, in some embodiments, sufficient to prevent actuator 340 from substantially moving from the retained location in the actuator support 479, and the actuator positioning mechanism 470 is configured to prevent the actuator support 479 from substantially moving within the artificial passageway 219 during operation of the actuator 340. For example, the removable securement may be achieved via an interlock between the actuator 340 and the collar that provides retention sufficient to withstand reaction forces resulting from operation of actuator 340.

In an exemplary embodiment, the interlock is provided by an interference fit between inner surface 479A of the collar of actuator support 479 and an outer surface of actuator 340. In an alternate embodiment, the interlock is implemented as threads of inner surface 479A that interface with corresponding threads on the outer surface of actuator 340. In another embodiment, O-rings or the like may be used to snugly wrap around actuator 340 and snugly fit inside the collar of actuator support 479. Grooves on the actuator 340 and/or on the collar may be included to receive the O-ring. In other embodiments, compression of the O-ring between the actuator 340 and the collar provides sufficient friction to retain the components in the actuator support 479. In another embodiment, actuator support 479 or actuator 340 includes a biased extension that is adjusted against the bias to insert the actuator into the support. The extension may engage a detent on the opposing surface to interlock the actuator and the support. Other embodiments include protrusions and corresponding channels on opposing surfaces of the actuator and support. An exemplary embodiment includes a spring-loaded detent that interfaces with a detent receiver of the opposing surface to hold the actuator in the support or that extends behind the actuator once the actuator has been positioned beyond the detent. An alternate embodiment may utilize O-rings to interlock the actuator in the support. Adhesive may be used to interlock the actuator in the support. Any device, system, or method that will interlock the actuator in the support that will permit embodiments detailed herein and/or variations thereof to be practiced may be utilized in some embodiments.

The trolley 478, which is rigidly connected to actuator support 479, is configured to move linearly in the direction of arrow 3 parallel to the longitudinal direction of extension of arm 477. In this exemplary embodiment, arm 477 includes tracks with which trolley 478 interfaces to retain trolley 478 to arm 477. These tracks also establish trolley 478 and arm 477 as a telescopic component configured to enable the adjustment of the location of actuator support 479, and thus actuator 340 when received therein, relative to the housing 446 (thus the implant body), in at least one degree of freedom (i.e., the degree of freedom represented by arrow 3). It is noted that other embodiments may permit adjustment in at least two or at least three degrees of freedom. Thus, when the trolley component is combined with the aforementioned joint 474, the actuator positioning system enables the location of the actuator 340 to be adjustable relative to the implant body in at least two or at least three degrees of freedom.

Movement of the trolley 478 along arm 477 may be accomplished via a jack screw mechanism where the jack screw is turned via a screw driver or a hex-head wrench. Movement of the trolley 478 may also or alternatively be achieved via application of a force thereto that overcomes friction between the trolley 478 and the arm 477. Any device, system, or method that permits trolley 478 to move relative to arm 477 may be used in some embodiments detailed herein and/or variations thereof.

Figure 5:
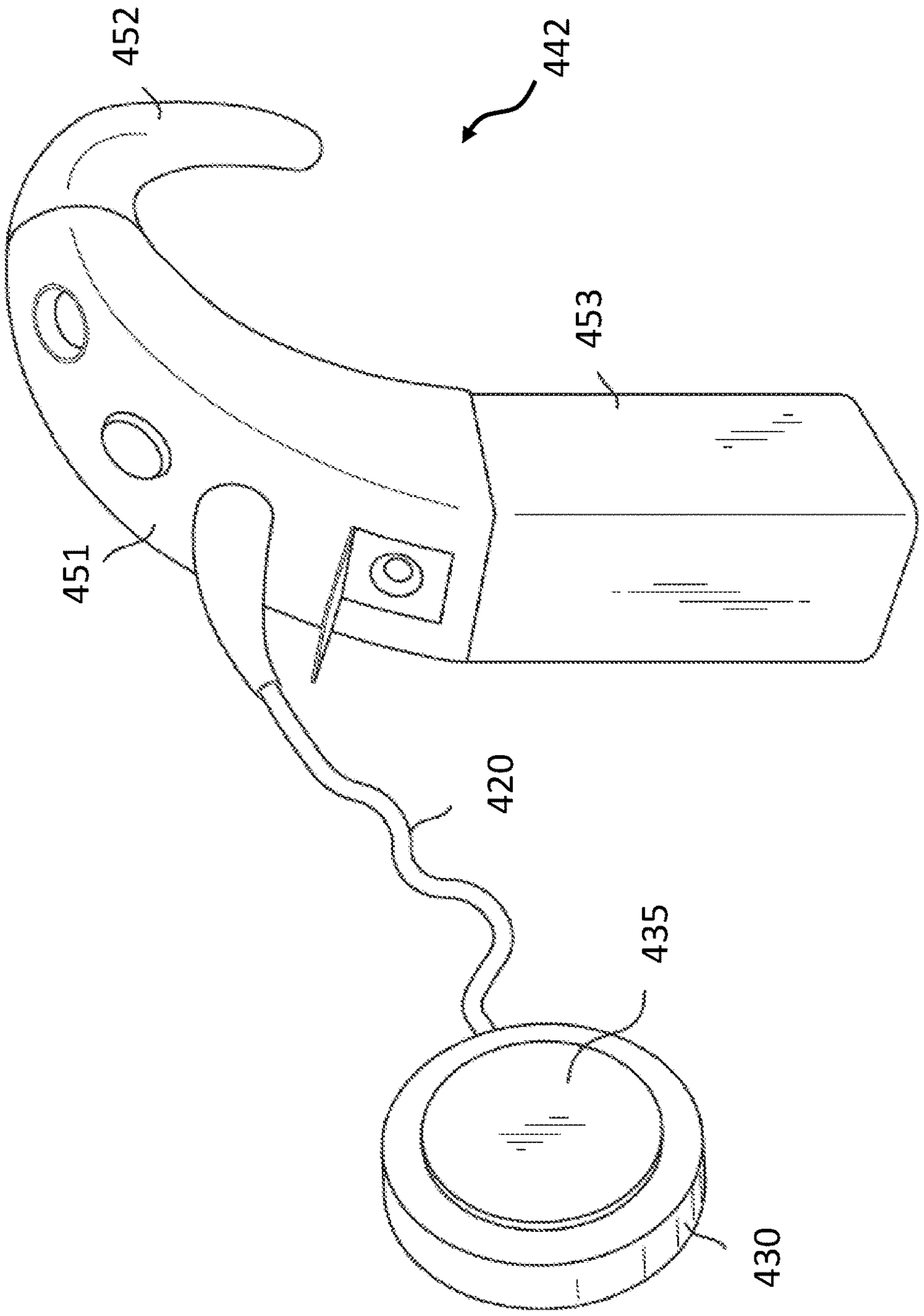
FIG. 5 is a perspective view of an exemplary external component of an exemplary hearing prosthesis in which at least some teachings detailed herein are applicable.

FIG. 5 depicts an alternate embodiment of an external component, external component 442, which corresponds to an external component usable as the external component FIGS. 2A-2B (i.e., in place of the button sound processor 242). In this embodiment, there is a behind-the-ear device that includes a behind the ear spine 451 having microphone ports, and ear hook 452, and a battery 453. In an exemplary embodiment, the microphone captures sound, and a sound processor in the behind-the-ear device converts that sound into an output signal which is fed to the headpiece 430 (sometimes referred to herein as the communications unit) via cable 420. That output signal energizes the inductance coil located in the headpiece 430 (which is held against the skin of the recipient via magnet 435) to evoke a hearing percept according to the teachings detailed herein.

Figure 6:
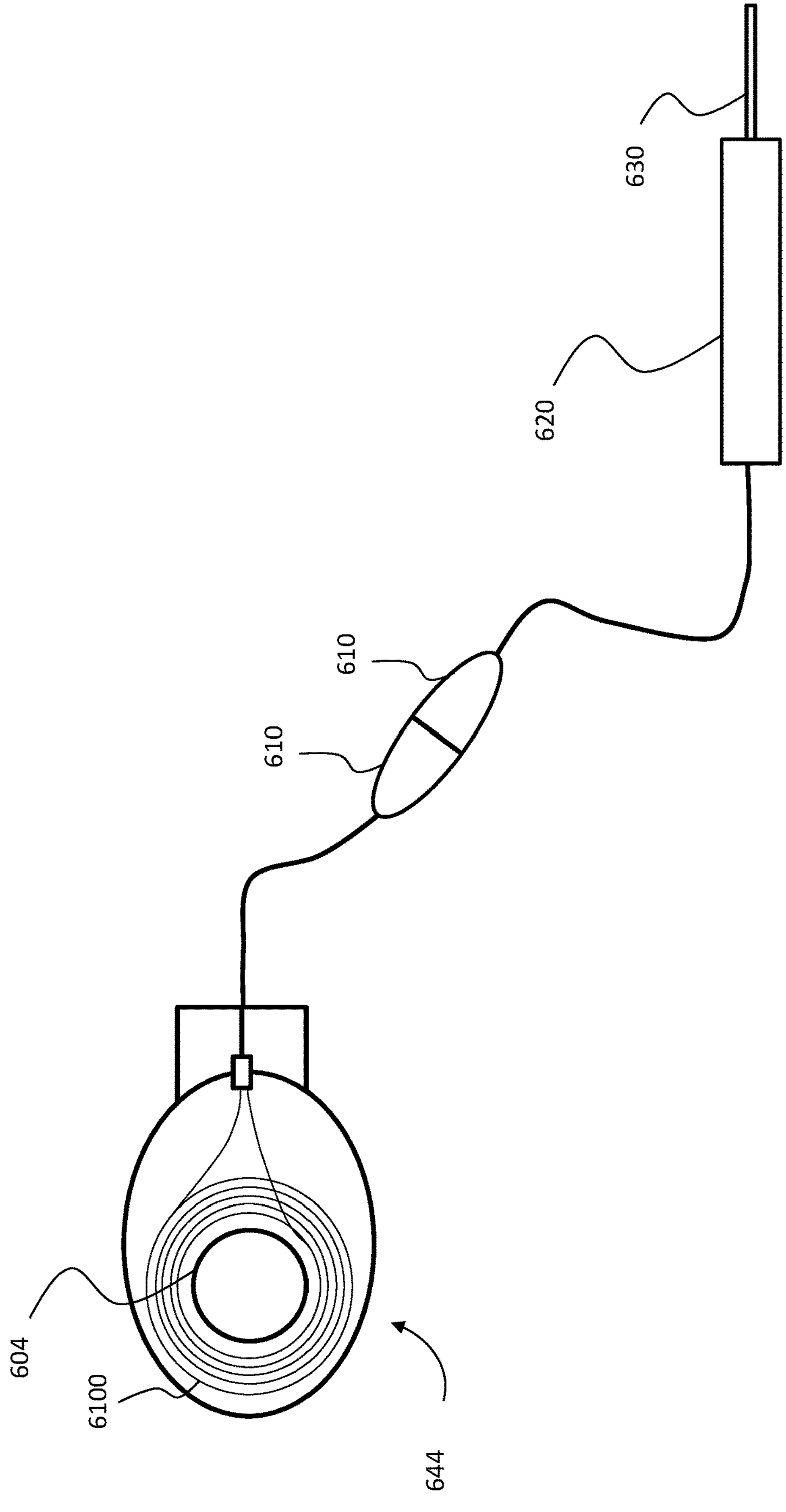
FIG. 6 is a perspective view of an exemplary implantable system according to an exemplary embodiment.

FIG. 6 depicts an alternate embodiment of an exemplary middle ear implant. Here, instead of a receiver unit and stimulator unit combined in a single implantable body (e.g., body 345 of FIG. 3), the receiver unit and the stimulator unit are bifurcated into two separate components coupled together with a connector. More specifically, a receiver unit 644 can be seen, including an inductance coil 6100. A magnet 604 is located inside the perimeter of the inductance coil so as to establish a magnetic attraction with the external component of the prostheses. In this regard, receiver unit 644 corresponds to receiver unit 330 detailed above. Inductance coil 6100 is in signal communication with a first connector 610 via electrical lead. This first connector 610 is connected to a second connector 610 that is in turn connected to a so-called intelligent actuator 620 via electrical lead. The intelligent actuator 620 includes an actuator, corresponding to actuator 340 detailed above and a coupling 630 corresponding to coupling 353 detailed above. The intelligent actuator 620 further includes a stimulator unit (or driver unit or drive unit, as it is sometimes referred to). Thus, in this regard, intelligent actuator 620 corresponds to stimulator unit 320 detailed above, plus additional functionalities of the actuator and the coupling. In an exemplary embodiment of use, an external component captures sound utilizing an external microphone, and transduces the sound into electrical signals which are provided to a sound processor located in the external component. The sound processor processes the sound, and outputs a signal to the inductance coil of the external component. The inductance coil of the implantable component receives this signal, and the signal is provided to the intelligent actuator 620. The intelligent actuator is configured with the stimulator unit to provide signals to an actuator thereof so as to actuate and evoke a hearing percept. In an exemplary embodiment, this stimulator unit is mapped or otherwise contains data associated with the unique features of the recipient or is otherwise calibrated so as to actuate in a specific manner related to the specific recipient for a given signal. Thus, in an exemplary embodiment, the intelligent actuator does not need an additional capsule for power, decoding and/or driving, in at least some exemplary embodiments.

Figure 7:
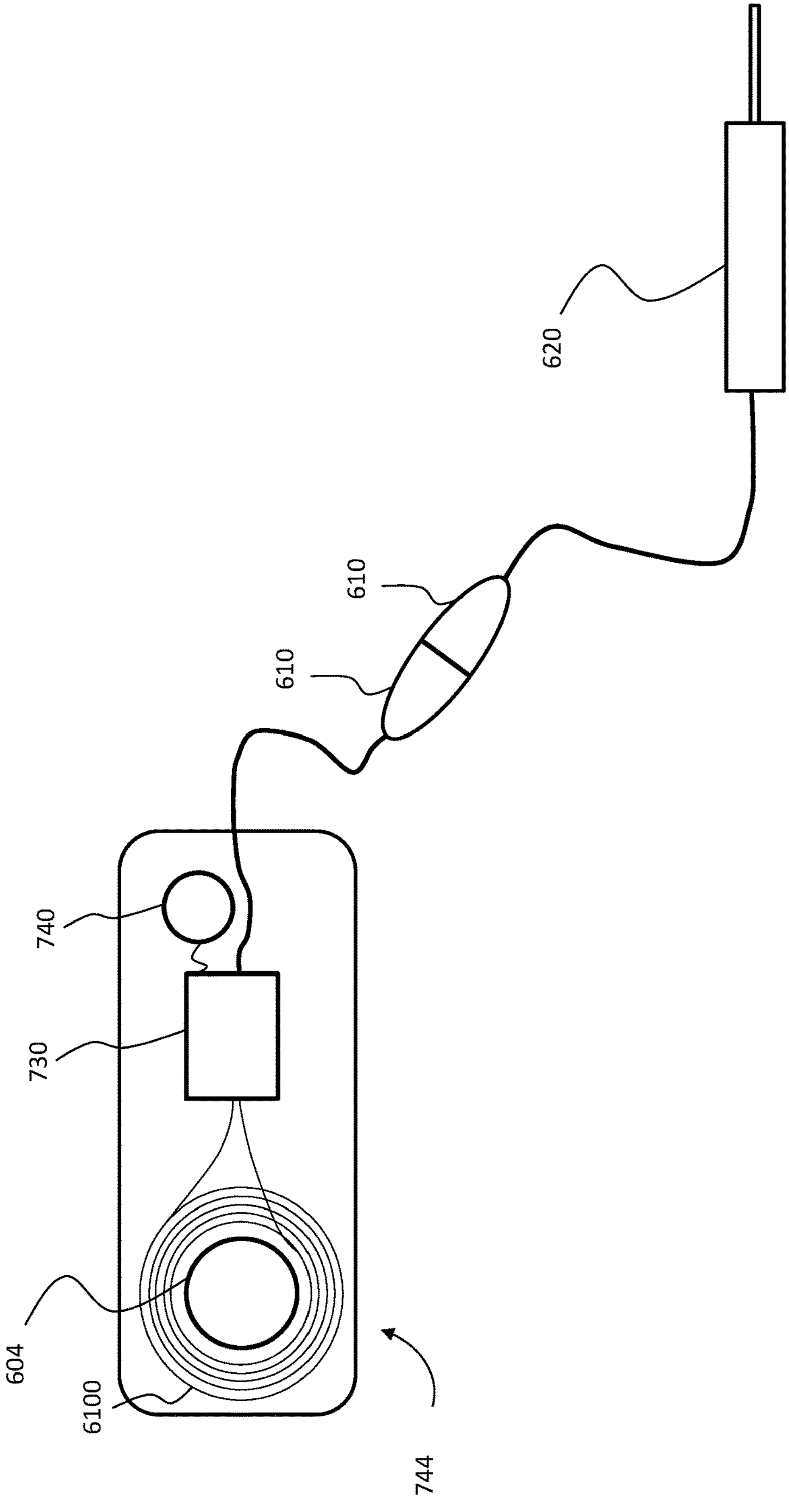
FIG. 7 is a perspective view of another exemplary implantable system according to an exemplary embodiment.

FIG. 7 depicts an alternate embodiment utilizing the intelligent actuator of FIG. 6. Here, implant body 744 includes a receiver unit, but also includes a sound processor unit 730. The sound processor unit 730 is in signal communication with an implanted microphone 740. In this regard, implant body 744 corresponds to a component for a totally implantable hearing prosthesis. As can be seen, signal processor 730 is in signal communication with the intelligent actuator 620 via connectors 610 and the associated leads. Here, sound captured by the implantable microphone 740 is transduced into electrical signals that are provided to the sound processor 730 the sound processor then generate a signal to the intelligent actuator 620. The signal can be generally the same the signals that are provided by the coil 6100 in the embodiment of FIG. 6. It is briefly noted that when the implant is being utilized as a totally implantable hearing prosthesis, the coil 6100 is only utilized for programming, charging and/or diagnostics, in at least some exemplary embodiments. That said, in some exemplary embodiments, the coil 6100 is utilized for sound streaming. In an exemplary embodiment, the same communication protocols utilized for sound streaming as that utilized when the implantable body 744 is receiving signals from the external component based on captured sound by the external component can be used when the implantable body is utilized as part of a partially implantable or semi-implantable hearing prosthesis. That said, in an alternate embodiment, a different protocol for sound streaming can be utilized than that which is utilized for the communication of sound captured by a microphone.

Figure 8:
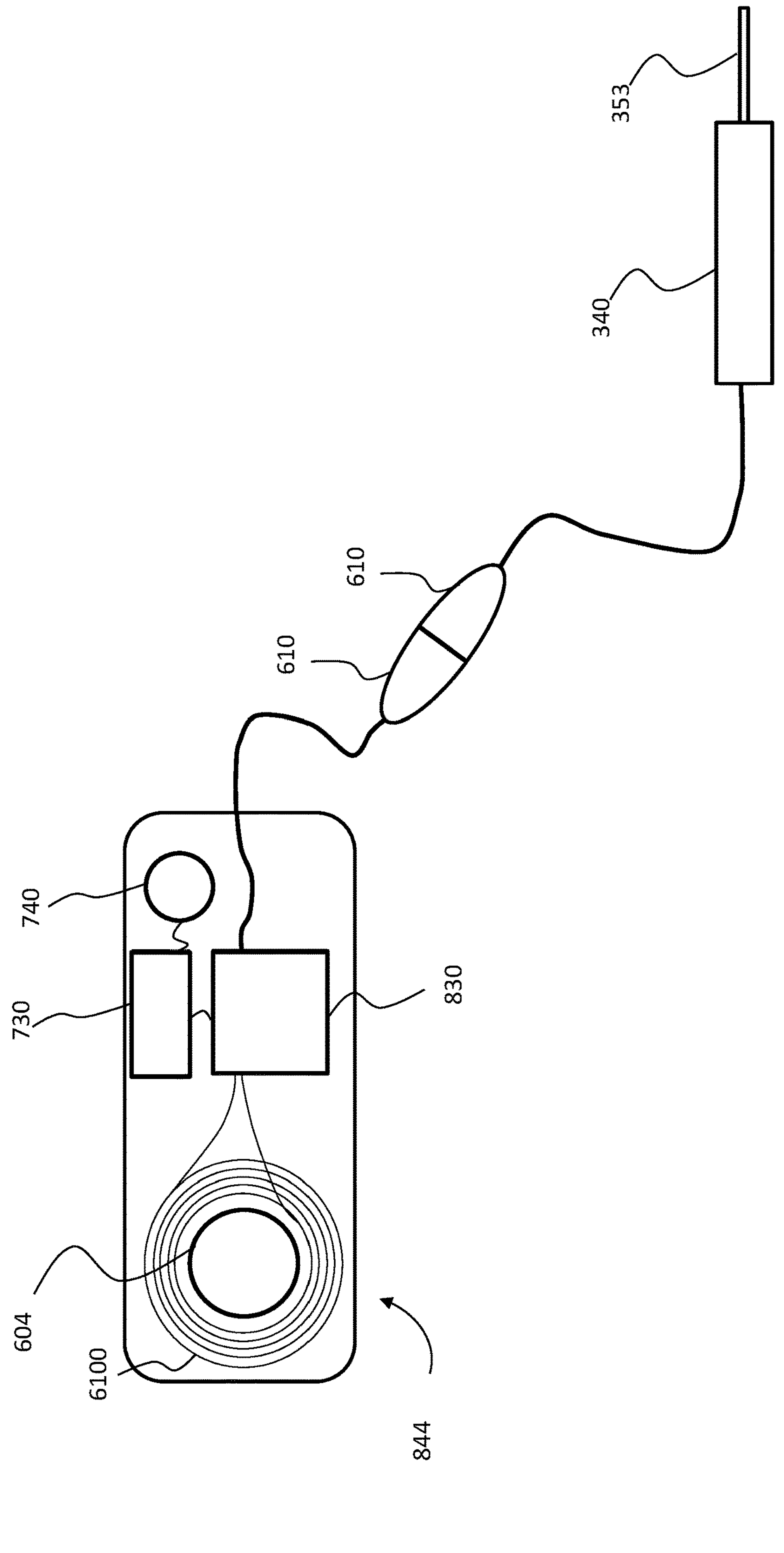
FIG. 8 is a perspective view of another exemplary implantable system according to an exemplary embodiment.

FIG. 8 depicts an alternate embodiment of an implant body, including an inductance coil 6100, the sound processor 730, the implantable microphone 740, and a stimulator unit 830. In this regard, the embodiment of FIG. 8 corresponds to a totally implantable version of the embodiment of FIG. 3 detailed above. Here, the actuator 340 corresponds to the actuator of FIG. 3 detailed above. That said, in an alternate embodiment, the intelligent actuator 620 can be utilized. In an exemplary embodiment, the intelligent actuator can be configured to determine whether or not the signals from the implantable body include signals from a stimulator unit, or otherwise simply contain data signals that are to be used by the intelligent actuator zone stimulator unit. Some additional details of this are described in greater detail below.

Figure 9:
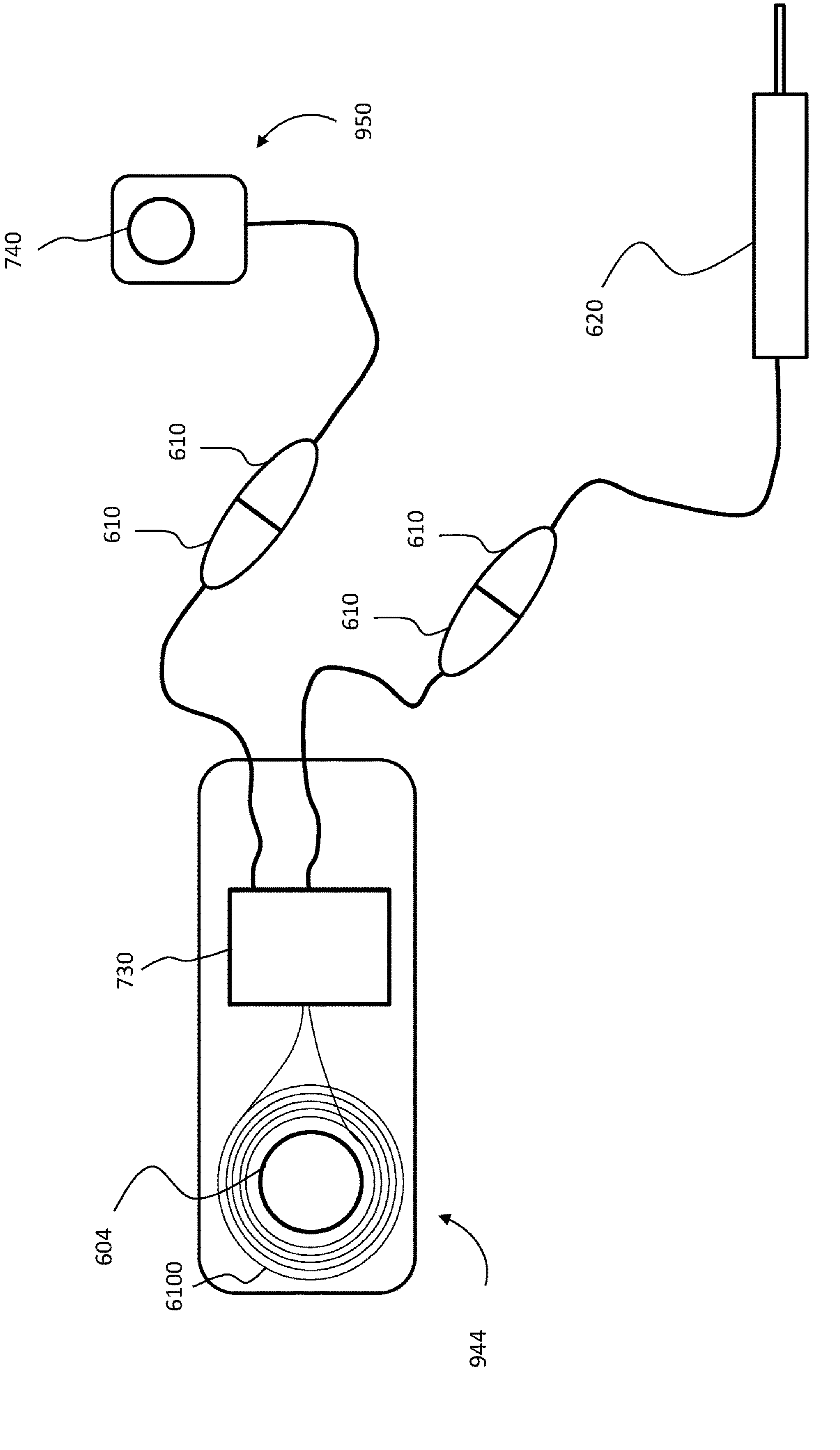
FIG. 9 is a perspective view of another exemplary implantable system according to an exemplary embodiment.

FIG. 9 depicts a variation of the embodiment of FIG. 7, where instead of an implantable microphone being part of the implant body 944, the implantable microphone is part of a remote microphone unit 950 that is in signal communication with the sound processor 730 via connectors 610 and the associated leads. Here, as is the case in the embodiment of FIG. 7, the intelligent actuator 620 is in signal communication with the sound processor 730 via the connectors 610 and the associated leads. Note that in an alternate embodiment, the embodiment of FIG. 9 can correspond to that of FIG. 8 with respect to the stimulator unit being part of the implant body 944, and the utilization of the actuator 340, etc.

Figure 10:
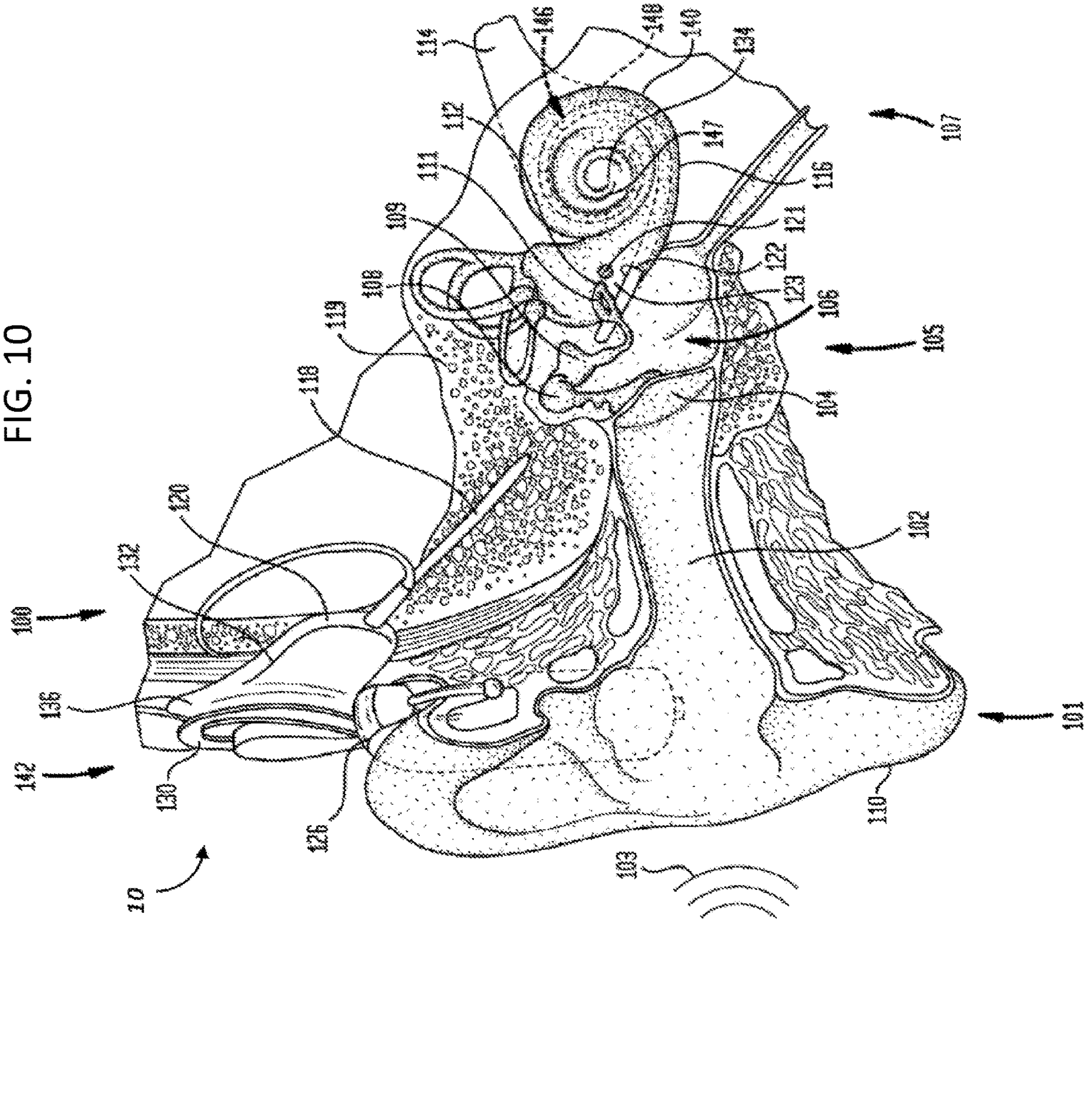
FIG. 10 is a perspective view of another exemplary prosthesis according to an exemplary embodiment.

FIG. 10 depicts a perspective cochlear implant, referred to as cochlear implant 100, implanted in a recipient, to which some embodiments detailed herein and/or variations thereof are applicable. The cochlear implant 100 is part of a system 10 that can include external components in some embodiments, as will be detailed below. It is noted that the teachings detailed herein are applicable, in at least some embodiments, to partially implantable and/or totally implantable cochlear implants (i.e., with regard to the latter, such as those having an implanted microphone and/or implanted battery). It is further noted that the teachings detailed herein are also applicable to other stimulating devices that utilize an electrical current beyond cochlear implants (e.g., auditory brain stimulators, pacemakers, etc.). It is noted that the teachings detailed herein are also applicable to so-called hybrid devices. In an exemplary embodiment, these hybrid devices apply both electrical stimulation and acoustic stimulation and/or mechanical stimulation to the recipient. Any type of hearing prosthesis to which the teachings detailed herein and/or variations thereof that can have utility can be used in some embodiments of the teachings detailed herein. Further, it is noted that the teachings detailed herein can be applicable to other types of prostheses, such as by way of example only and not by way of limitation, retinal prostheses.

In view of the above, it is to be understood that at least some embodiments detailed herein and/or variations thereof are directed towards a body-worn sensory supplement medical device (e.g., the hearing prosthesis of FIG. 10, which supplements the hearing sense, even in instances where all natural hearing capabilities have been lost). It is noted that at least some exemplary embodiments of some sensory supplement medical devices are directed towards devices such as conventional hearing aids, which supplement the hearing sense in instances where some natural hearing capabilities have been retained, and visual prostheses (both those that are applicable to recipients having some natural vision capabilities remaining and to recipients having no natural vision capabilities remaining). Accordingly, the teachings detailed herein are applicable to any type of sensory supplement medical device to which the teachings detailed herein are enabled for use therein in a utilitarian manner. In this regard, the phrase sensory supplement medical device refers to any device that functions to provide sensation to a recipient irrespective of whether the applicable natural sense is only partially impaired or completely impaired.

As shown, cochlear implant 100 comprises one or more components which are temporarily or permanently implanted in the recipient. Cochlear implant 100 is shown in FIG. 10 with an external device 142, that is part of system 10 (along with cochlear implant 100), which, as described below, is configured to provide power to the cochlear implant, where the implanted cochlear implant includes a battery that is recharged by the power provided from the external device 142.

In the illustrative arrangement of FIG. 10, external device 142 can comprise a power source (not shown) disposed in a Behind-The-Ear (BTE) unit 126, which can correspond to BTE unit 442 of FIG. 5. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive, and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 10 is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments, electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123, or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Figure 11:
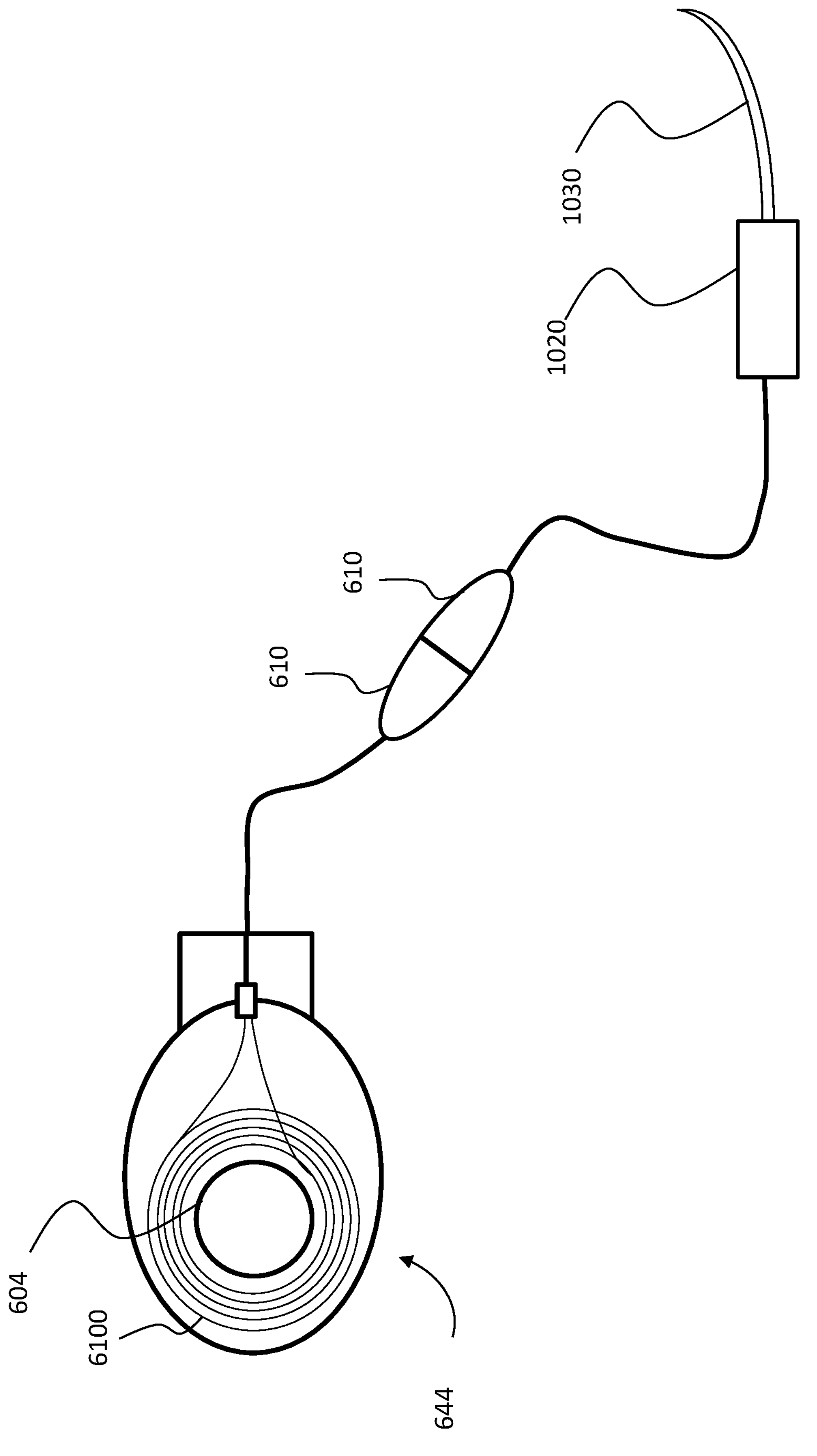
FIG. 11 is a perspective view of another exemplary implantable system according to an exemplary embodiment.

FIG. 11 depicts an exemplary embodiment of an implantable component of a cochlear implant, where, instead of the receiver stimulator unit being part of an integral component, instead, the receiver unit 644 is bifurcated from the stimulator unit of the cochlear implant. In this regard, element 1020 corresponds to the stimulator unit of the cochlear implant, with element and 30 corresponding to the electrode array. As can be seen, these components are in signal communication with the communication unit 644 via couplings 610 and their respective leads.

Figure 12:
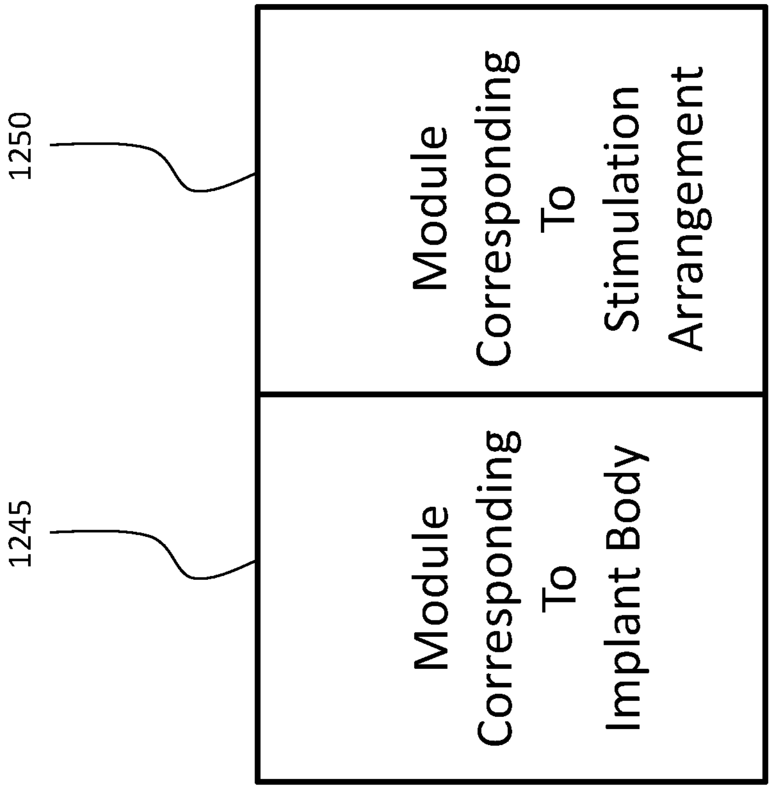
FIGS. 12-23 are functional block diagrams representing various exemplary hearing prostheses according to some of the teachings detailed herein in modularized format.
Figure 13:
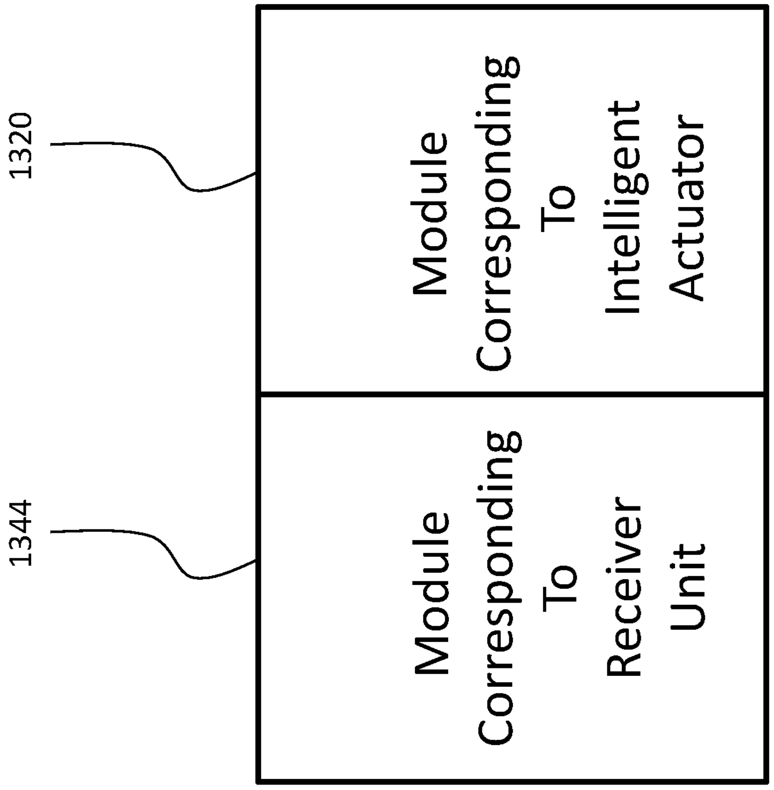
Figure 14:
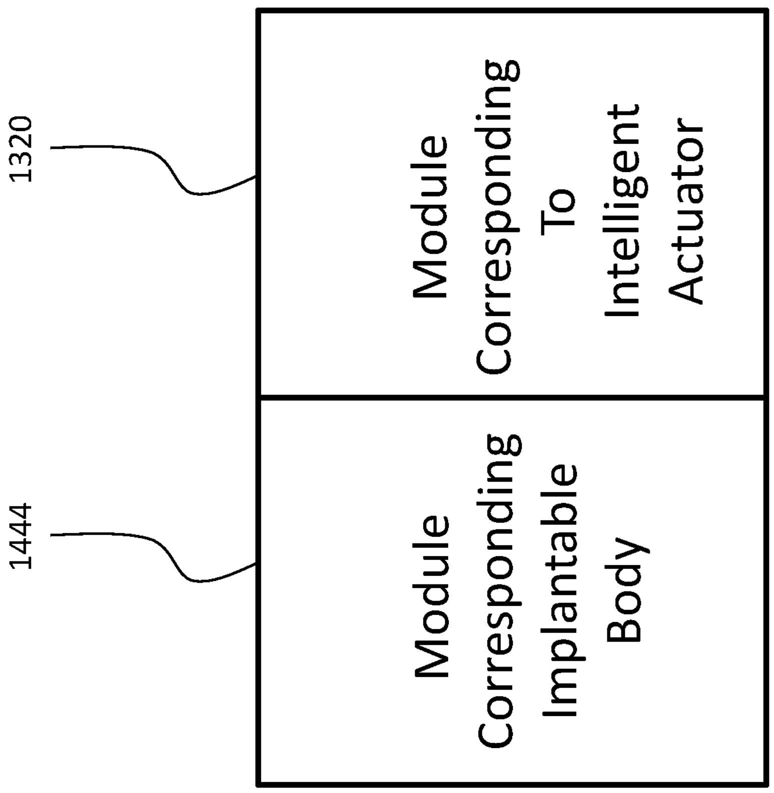
Figure 15:
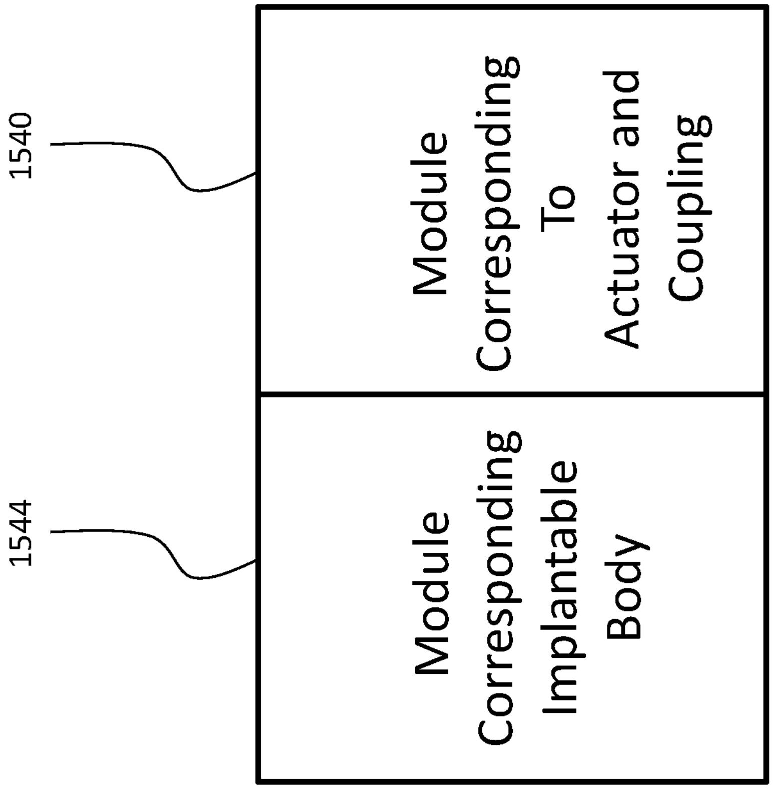
Figure 16:
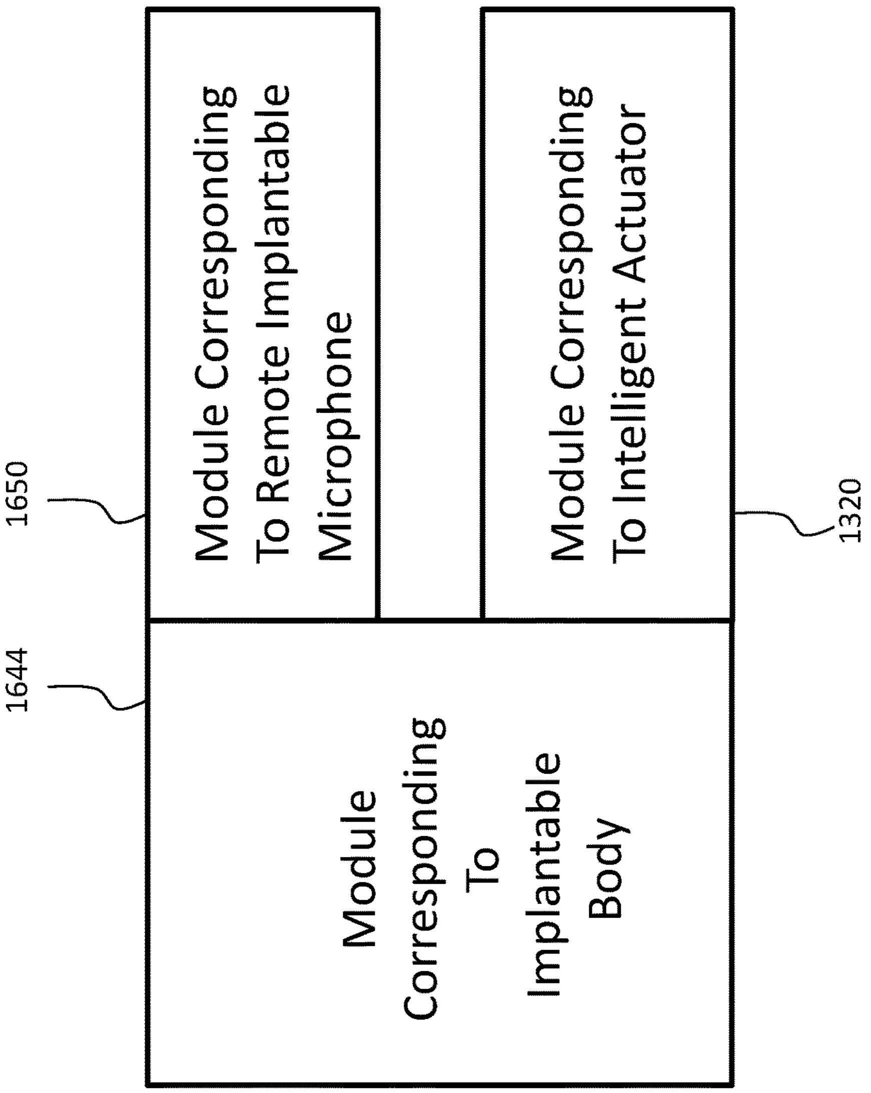
Figure 17:
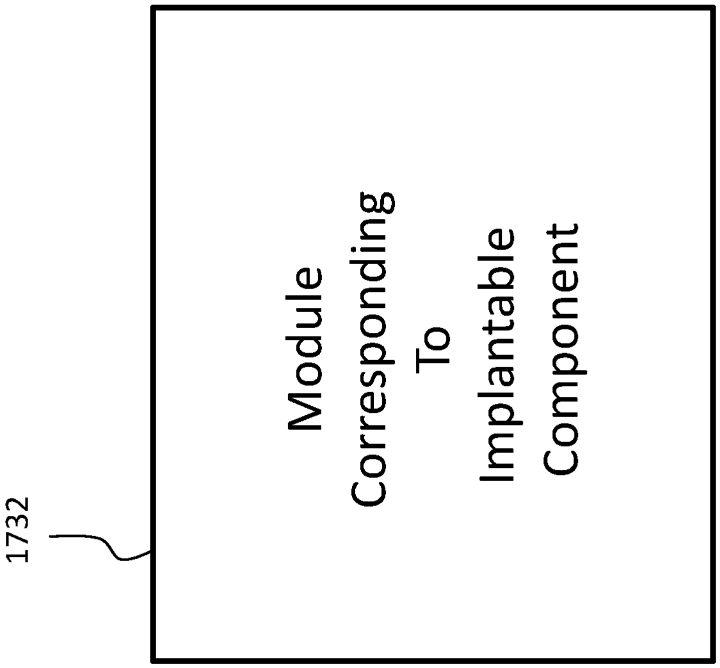
Figure 18:
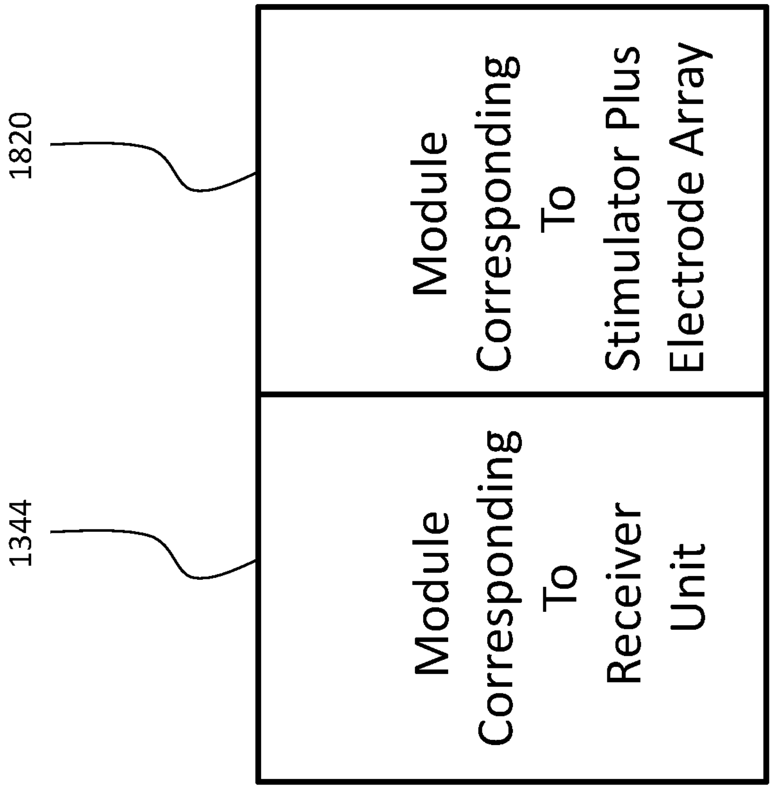

In an exemplary embodiment, the various components of the implantable prostheses detailed herein can be provided by way of implantable modules that are configured to communicate with one another. FIG. 12 depicts by way of functional block diagrams a module 1245 which corresponds to the implant body 345 of FIG. 3, and a module 1250, which corresponds to the stimulation arrangement 350. Herein, contact between the two blocs indicates that the components are in some form of signal communication with each other. By way of example, block 1250 would be in signal communication with block 1245 via cable 328 vis-à-vis FIG. 3. FIG. 13 depicts an alternate example of an embodiment again by way of functional block diagrams, a module 1344 which corresponds to the receiver unit 644 of FIG. 6. FIG. 13 also depicts a module 1320 which corresponds to the intelligent actuator 620 of FIG. 6. Again, the contact between the two modules represents signal communication between the communications unit/receiver unit 644 and the intelligent actuator 620 via the connectors 610 and the associated leads. FIG. 14 depicts an exemplary functional schematic representative of the embodiment of FIG. 7, where module 1444 corresponds to the implantable body 744 of that figure, and module 1320 corresponds to the intelligent actuator concomitant with the embodiment of FIG. 13. FIG. 8 depicts an exemplary functional schematic representative of the embodiment of FIG. 8, where module 1544 corresponds to the implantable body 844 thereof, and module 1540 corresponds to the actuator 340 and coupling 353 thereof (the stimulation arrangement 350 of FIG. 3). Continuing on, FIG. 16 depicts an exemplary functional schematic representative of the embodiment of FIG. 9, where module 1644 corresponds to the implantable body 944 of FIG. 9, module 1650 corresponds to the remote implantable microphone 950 of FIG. 9, and module 1320 corresponds to the intelligent actuator 620 of FIG. 9. As can be seen, modules 1650 and 1320 are not in contact with each other. This represents that this embodiment requires the module 1644 to "unite" the two, at least with respect to signal communications. Corollary to this is that because module 1650 is shown in contact with module 1644, and module 1320 is shown in contact with module 1644, the respective contacting modules are in signal communication with each other. FIG. 17 depicts an exemplary functional block diagram of a module 1732, which corresponds to the implantable component of FIG. 10. FIG. 18 depicts an exemplary functional block diagram including module 1344, which corresponds to the receiver unit 644 of FIG. 11, and module 1820, which corresponds to the stimulator 1020 plus the electrode array 1030 of FIG. 18.

Figure 19:
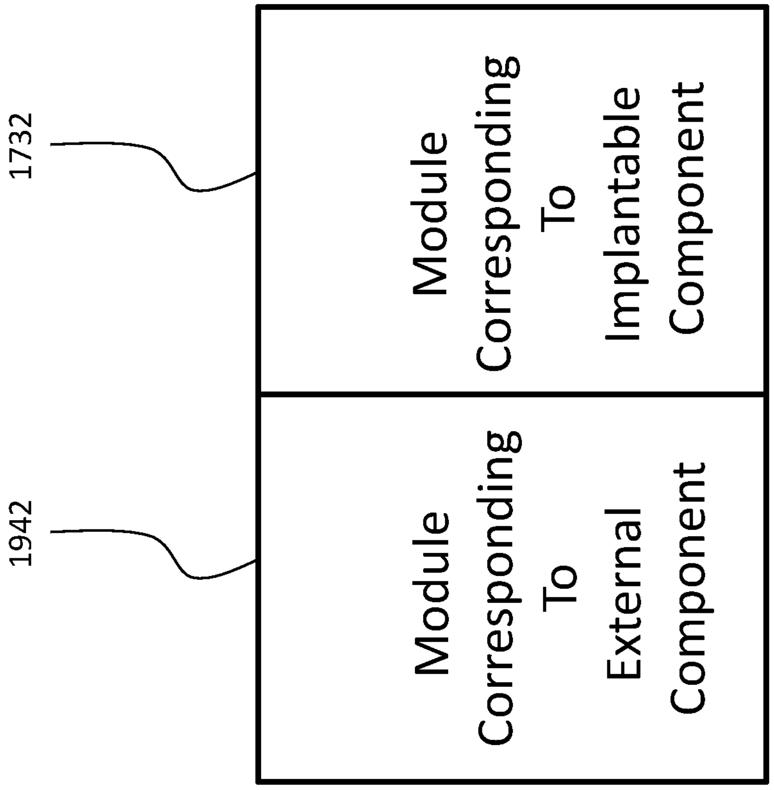

To be clear, it is noted that in the functional schematics depicting the modules, contact between the two modules as depicted in the FIGS. does not necessarily mean physical contact there between. In this regard, FIG. 19 depicts an exemplary functional schematic depicting module 1942 contacting module 1732. Here, module 1942 represents the external component 142 of FIG. 10. As noted above, the external component 142 is in signal communication with the implantable component 100 (represented by module 1732) via the transcutaneous inductance link. Thus, even though there is a layer of skin and other body tissue between these two modules, FIG. 19 depicts the modules in contact with each other. Corollary to this is FIG. 20, which depicts a module 2042. Module 2042 represents an external component of a bimodal hearing prosthesis. This external component is in signal communication with the receiver stimulator/implantable component of the cochlear implant 100, represented by module 1732. The external component is also in signal communication with a receiver/speaker unit of an acoustic hearing aid that is located in the outer ear or otherwise against the outer ear of a recipient. This receiver speaker unit is represented by module 2060. Here, module 2042 can represent a behind the ear device, such as behind the ear device 442 of FIG. 5. The receiver speaker of the acoustic hearing aid unit can be in signal communication with the BTE device via a cable connection. The BTE device can be in signal communication with the implantable component of the cochlear implant via the transcutaneous inductance field link.

Figure 20:
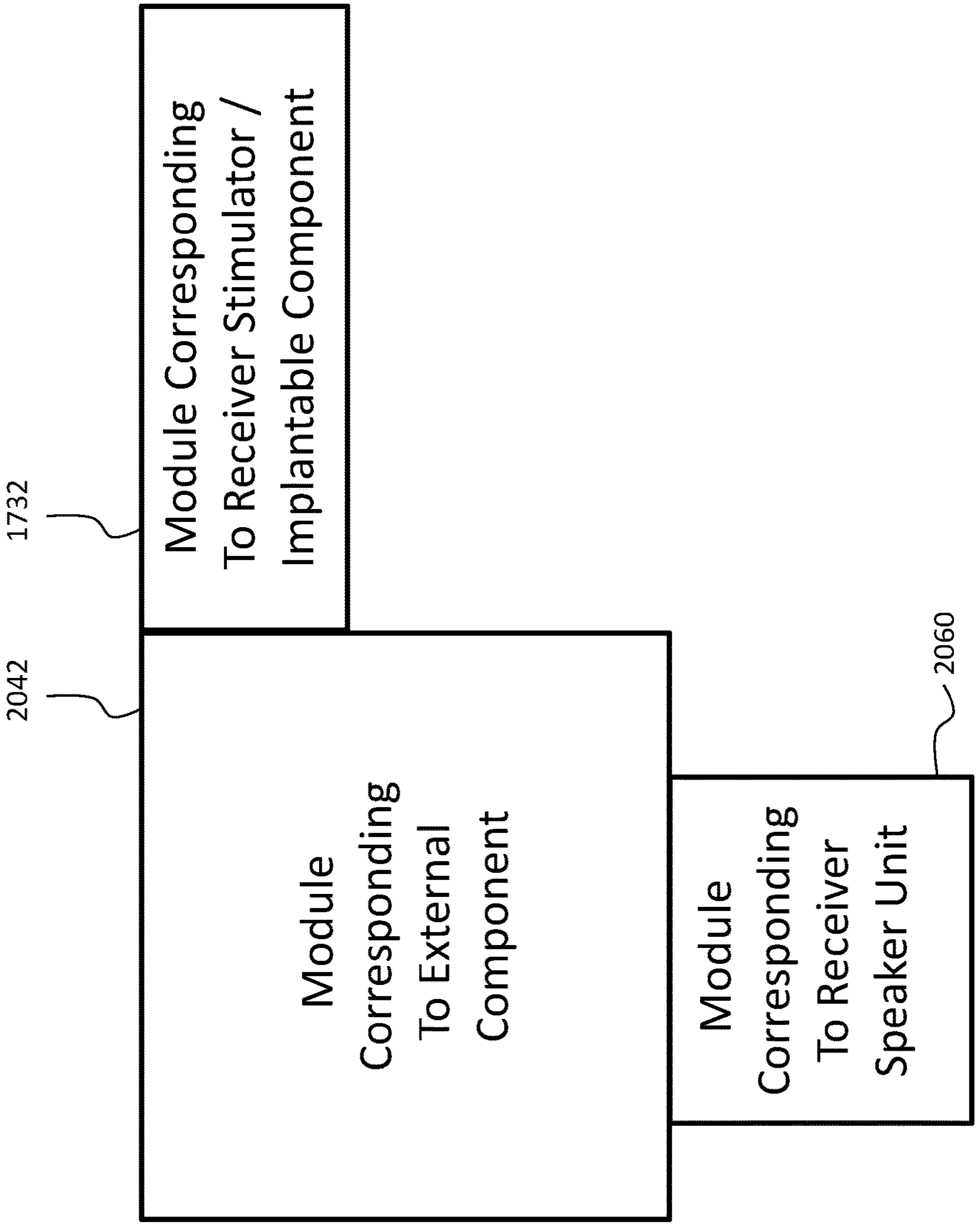
Figure 21:
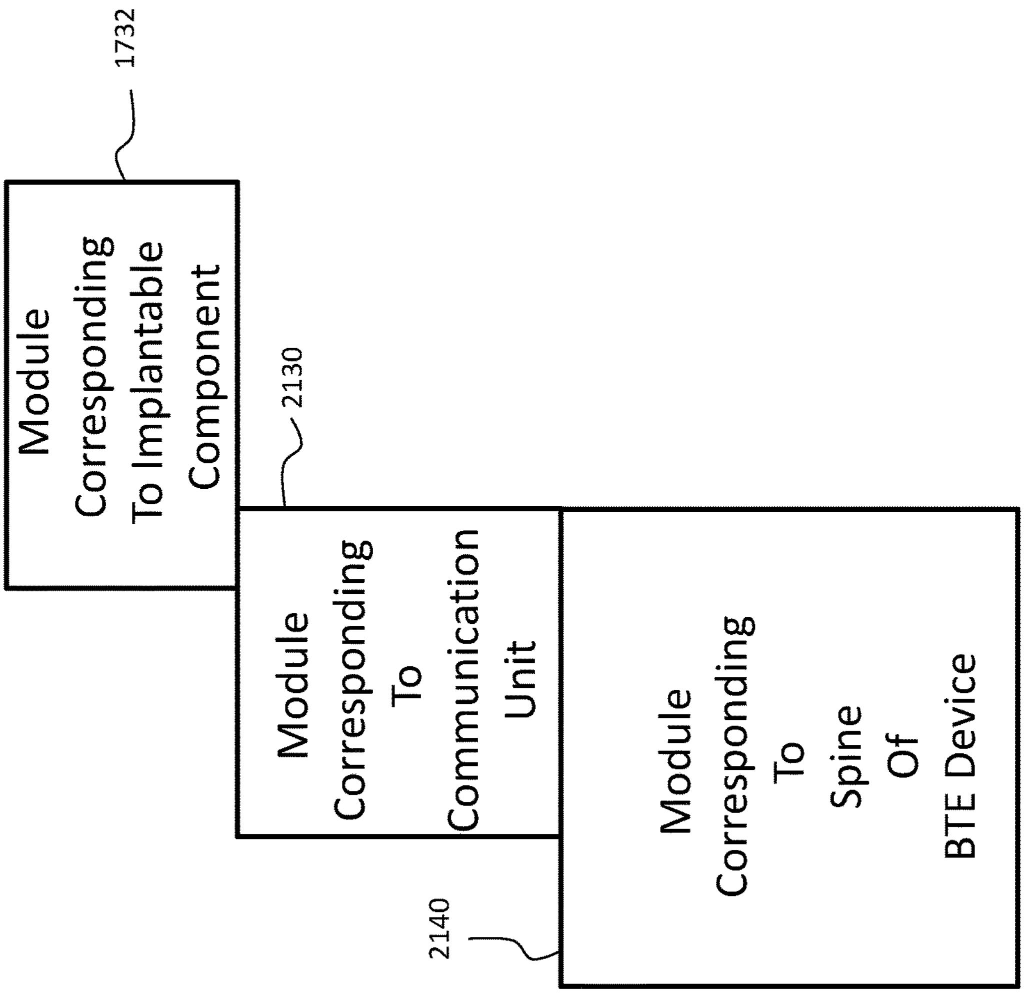

While the embodiment of FIG. 20 depicts the BTE device and the headpiece 430 (corresponding to a communications unit—effectively the same as element 644 detailed above) as being part of a single module, in an alternate embodiment, the two components can be presented in separate modules. According to the teachings detailed herein, this can be done in a scenario where the headpiece 430 of the BTE device could have unique capabilities or otherwise could operate in a different functional manner depending on how that device is utilized. For example, in a scenario where the headpiece 430 is a standard inductance coil that has an input connector, and the inductance coil operates based on the input thereto, the headpiece 430 would not be considered its own module. However, in an exemplary embodiment where the operation of the inductance coil could be changed depending on how it is used (e.g., some coils are deactivated when the inductance coil is utilized to charge the implant as opposed to when the inductance coil is utilized to communicate control information to the implant), the inductance coil could be modularized and considered for the purposes of implementing the teachings detailed herein as a separate module. To this end, FIG. 21 depicts an exemplary embodiment of the spine for 51 of the BTE device 442 of FIG. 5, represented by module 2140, in signal communication with module 2130, which corresponds to the communication unit 430 of FIG. 5 (the inductance coil), which in turn is in communication with module 1732, which represents the implantable component of the hearing prosthesis of FIG. 10. This is as contrasted with the embodiment of FIG. 20, where the inductance coil/communications unit (headpiece) of the BTE device is part of the module that includes the spine 451 of the BTE.

It is noted that while the above modularization and the teachings detailed herein are directed towards various components of a hearing prosthesis detailed herein, the modularization according to the teachings detailed herein are also applicable to other types of hearing prostheses/other components thereof. Further, the teachings detailed herein are applicable to other types of prostheses, such as by way of example, retinal implants or other sense implants. In this regard, the teachings detailed herein are but exemplary, and are applicable beyond the specific teachings detailed herein.

In an exemplary embodiment, one or more or all of the modules of a given module system (hereinafter, the aggregate of modules in signal communication with other modules is referred to as a module system) contain a set of utilitarian information regarding its own status and relationship to the overall system. The modules can include a chip, such as by way of example only and not by way of limitation, a nonvolatile memory chip, which contains information or otherwise stores information or otherwise stores data therein/thereon in a manner that permits the data to be stored over long periods without energy input (e.g., months, years, etc.). In some exemplary embodiments, such data can include by way of example only and not by way of limitation, module manufacturing information, model and serial number; parameters specific to the module, e.g. microphone sensitivity, actuator transformer constant; parameters specific to the recipient, e.g. implantation date, audiologic fitting parameters (gain by frequency, compression ratio and knee point), type of surgery and location of actuator (incus body, stapes capitulum, round window, etc.); and parameters specific to the implanted system, e.g., bilateral versus unilateral, microphone location, type of actuator, etc. In an exemplary embodiment, the modules are configured to transmit the data to another module and/or otherwise enable another module to read the data there from. Note further that in an exemplary embodiment, the modules are configured to read the data from another module, at least providing that the other module enables such reading.

In view of the above, it is to be understood that the modules can be configured so as to have the capability of communicating amongst themselves. In an exemplary embodiment, the modules or otherwise the module system is configured to prompt or otherwise enable the communication amongst themselves without instructions or otherwise prompting from outside the system. As will be detailed below, in an exemplary embodiment, the modules are configured so as to be self-reconfiguring and/or so as to enable one or more modules to reconfigure one or more other modules or at least instruct one or more other modules to reconfigure themselves. By way of example only and not by way of limitation, with respect to the module 2130 of FIG. 21, module 2130 can receive input from module 2140 corresponding to output from a signal processor/sound processor, and thus generate an inductance field based on that input. In another exemplary embodiment, the module 2130 can receive input from a power source or the like, and, based on that input, reconfigure itself so as to utilize fewer of the inductance coils so as to be more efficient when generating the inductance field to recharge the implantable component. Alternatively and/or in addition to this, the module 2130 can be configured so as to determine that instead of BTE spine 2140 in signal communication therewith, a charger component or the like utilized to specifically charge the implantable component, is in signal communication with the module 2130. Based on the recognition that this other type of component is now in signal communication with the module 2130, the module 2130 can reconfigure itself for recharging the implantable component. Subsequent to this, if module 2140 is again placed into signal communication with module 2130, and/or the recharging model is taken out of signal communication with module 2130, module 2130 can reconfigure itself back to the configuration that is optimized or otherwise more efficient for transmission of control signals to the implant to evoke a hearing percept. Note also that in alternate embodiments, module 2140 or the recharging module can be configured to instruct the module 2130 to reconfigure itself accordingly.

Figure 22:
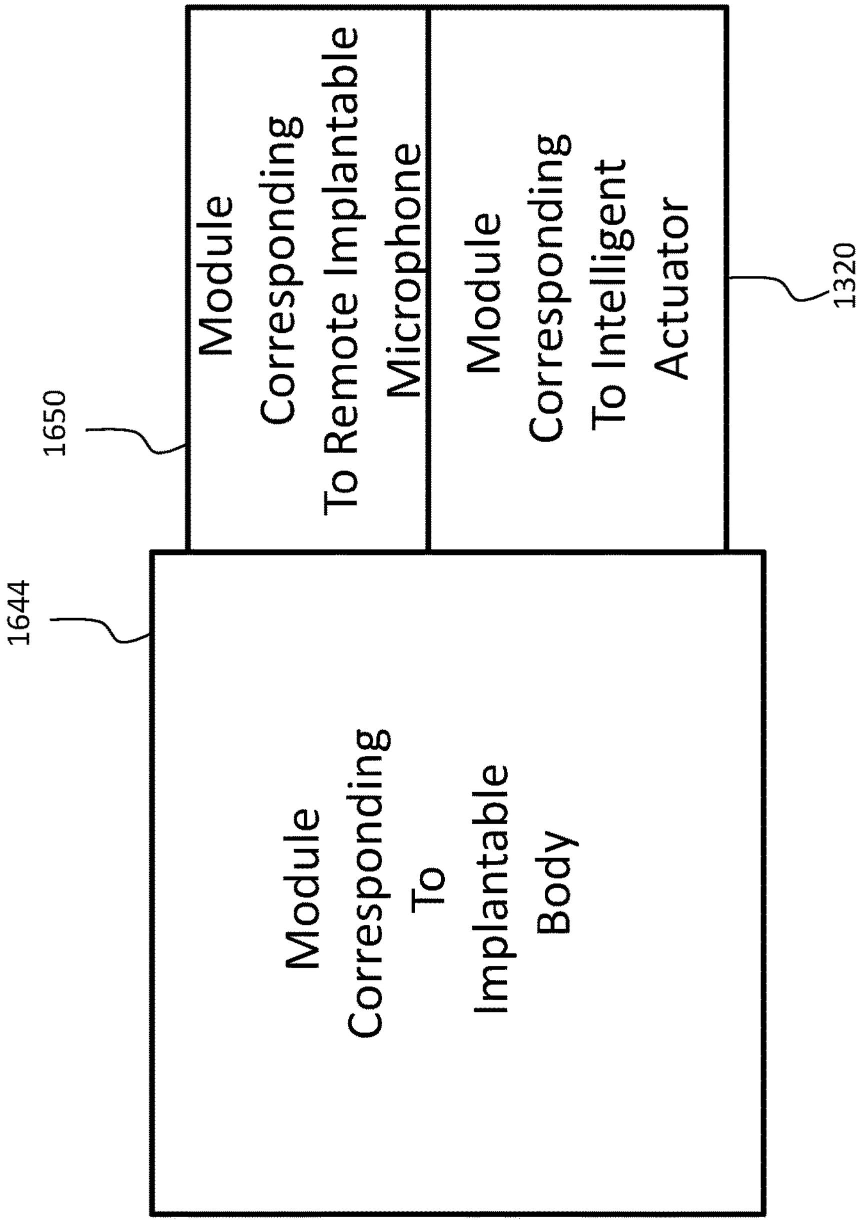

The communications between the modules may be executed by way of example only and not by way of limitation, and thus the modules may be configured to communicate via wired connection from the transmitting to the receiving module; wired connection from the transmitting, through an intermediate module, to the receiving module; wireless connection by implanted coil or antenna from the transmitting to the receiving module using near-field (inductive) or medium-field coupling; wireless connection in both directions between the implanted module and an external device such as an audiologist's programming interface or the recipient's own sound processor and/or wireless connection between one and any number of other modules using the external device as an intermediary. Any device, system, and/or method of communication between the modules can be utilized in at least some exemplary embodiments. In an exemplary embodiment, the modules can include, by way of example only and not by way of limitation, an implantable coil with connector, an intelligent actuator with RF decoder and driver, capable of receiving both power and audio signal from a coil, and also two-way communication with an external device or another module, an implantable sound processor with battery and integrated microphone, an implantable sound processor with battery and pendant microphone and/or an implantable intelligent microphone. To this again, in an exemplary embodiment, a given system can include a plurality of modules that are in turn in communication with a plurality of modules or otherwise are enabled to be placed or otherwise placed themselves into signal communication with a plurality of modules. By way of example only and not by way of limitation, with respect to the embodiment of FIG. 16, the implantable remote microphone represented by module 1650 could be configured to also communicate with the intelligent actuator represented by module 1320, at least in an exemplary embodiment where the intelligent actuator further includes a sound processor that can be redundant to the sound processor of module 1644. This is depicted by way of example in FIG. 22, where module 1650 is depicted as contacting module 1644 and module 1320, and module 1320 is depicted as contacting module 1644 and module 1650.

At least some exemplary embodiments of the teachings detailed herein can have utilitarian value with respect to enabling the combination and/or recombination and/or the decombination, etc. of modules of a module system as circumstances associated with the recipient change or otherwise other changes occur, where such changes can have utilitarian value. The following will be described in terms of some exemplary scenarios of changing a given system by removing and/or incorporating additional modules. The following exemplary scenario is just that, exemplary. It is to be understood that other exemplary scenarios are applicable to the teachings detailed herein and/or variations thereof.

By way of example only and not by way of limitation, an initial scenario may exist where a module system that includes an implantable component is implanted in a pediatric recipient. Initially, the pediatric recipient is implanted with only the communication unit 644 (e.g., the receiver coil) and an implantable intelligent actuator 620. This corresponds to the embodiment of FIG. 6 and FIG. 13 detailed above. The implantable portion of the system is represented in modular form by FIG. 13, where module 2342 corresponds to the external component 242 of FIG. 2A, which external component includes an inductance coil configured to communicate with the communications module 1344. In this regard, the system of FIG. 23 is utilized exclusively with an external sound processor located in module 2342.

In this exemplary scenario, module 1320 is initially programmed or otherwise configured with data/information residing in nonvolatile memory thereof. In an exemplary embodiment, a portion of the nonvolatile memory (e.g., a block thereof), includes information/data enabling identification of that module when read or otherwise accessed. By way of example only and not by way of limitation, the information/data can include the actuator module, the serial number of the module and/or of the actuator, the manufacturing date, etc. Indeed in an exemplary embodiment, case specific/recipient specific information can be included or otherwise stored in the memory. By way of example only and not by way of limitation, a recipient identification information can be stored in the memory, the implant center information to and/or the implant date can be stored in the memory. Still further, in another block of the nonvolatile memory, parameters specific to the recipient's method of ossicular attachment can be stored therein. By way of example only and not by way of limitation, information relating to attachment to the incus body, the incus long process, the stapedotomy or round window membrane can be stored therein. Still further, in an exemplary embodiment, the nonvolatile memory includes information or data relating to mapping of predicted output in equivalent SLP to input voltage. Any data or information having utilitarian value can be stored in the memory.

Figure 23:
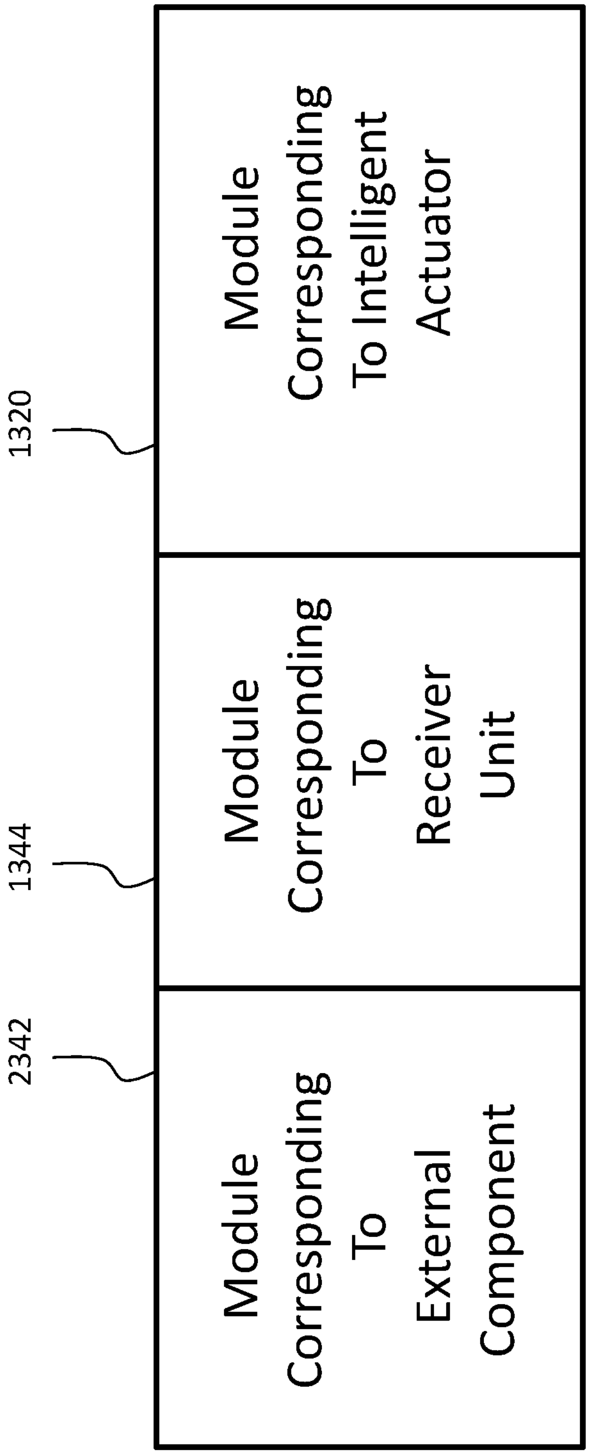

In an exemplary embodiment, the system of FIG. 23 is configured such that the external component 2342 can access this data or otherwise access at least some of the data. In an exemplary scenario, the external module 2342, which includes the sound processor, is configured to access this data and configure or otherwise adjust a processing regime of the sound processor based on this data so as to deliver a voltage based on the recipients fitting parameters and then translate such to the desired auditory stimulation level. In an exemplary embodiment, the external module 2342 is configured to read the data from the memory in module 2320. In an exemplary embodiment, the external module 1324 is configured to automatically read the data from the memory in module 2342 upon being placed into signal communication with module 1344 which is in signal communication with module 1320. Alternatively, and/or in addition to this, the module 1320 is configured to upload or otherwise output the data to the external component/module 2342 via module 1344 upon module 2342 being placed into signal communication with module 1344.

It is briefly noted that for purposes of linguistic economy, any disclosure of a first module reading data from a memory of a second module corresponds to a disclosure of the alternate embodiment and/or the additional embodiment of the second module uploading that data to the first module, unless otherwise noted.

The following is directed towards operation of the system of FIG. 23 when the intelligent actuator 1320 is being utilized in the intelligent mode. That is, the intelligent actuator 1320 is configured to operate based on a received input directly based on an RF signal or the like, and deconstruct that signal into a "stimulation signal" to be outputted to the actuator of the intelligent actuator. Basically, the intelligent actuator serves in part as the stimulator of the embodiment of FIG. 3 detailed above. In an exemplary embodiment, module 1320 (the intelligent actuator) contains a logic circuit that is configured to detect the signature of the external module 2342 and/or a signature of another module (more on this below). In an exemplary embodiment, the module 1320 is configured such that, when the external module 2342 is detected, module 1320 passes those signals received from module 1344 to an RF decoder circuit contained within module 1320 or otherwise in signal communication with module 1320 so as to decode the input signal with respect to a utilitarian coding regime (e.g. PWM or Sigma Delta, etc.). The ability to decode the input signal can have utilitarian value with respect to scenarios where the input to the module 1320 corresponds to the RF signal from module 1344, such as when the system is in the configuration of FIG. 23. This is because the "stimulator" component of the intelligent actuator is driven by the RF signals from the external module 2342 which have been transmitted to the internal communication module 2344. Alternatively, and/or in addition to this, the external component numeral 2342 can embed a code into the signal transmitted to the implantable module 1344, and the implantable module 1320 can be configured to read or otherwise detect that signal, and recognize that the signal should be provided to the RF decoder circuit. Thus, the module 1320 need not necessarily recognize that the external module 2342 is in signal communication there with. Any device, system, and/or method that can enable the system of FIG. 23 to recognize that a given signal requires RF decoding and thus the decoding functionality of module 1320 or another module of the system should be engaged can be utilized in at least some exemplary embodiments.

Continuing with the exemplary scenario of use, as the recipient matures from the pediatric state, or otherwise as technology advances, there becomes a point in time where it is utilitarian to upgrade the system to a so-called totally implantable system. In this regard, FIGS. 7 and 8 detailed above depict totally implantable middle ear implant systems, the difference between the two being that the embodiments of FIG. 8 utilizes the standard actuator of the embodiment of FIG. 3, and the embodiment of FIG. 7 utilizes the intelligent actuator 620. In an exemplary embodiment, the entire prosthesis is explanted (e.g., modules 1344 and 1320 are removed from the recipient), albeit the coupling component to the ear system may be left in place for later use, and the prosthesis of FIG. 8 is implanted in its place. However, it can also be utilitarian to instead maintain the actuator as implanted/in its implanted location. This thus corresponds to maintaining the intelligent actuator 620 implanted in the recipient. Accordingly, in an exemplary embodiment, the connection between the intelligent actuator 620 and the receiver unit 644 can be broken at connectors 610, and the implantable body 744 of FIG. 7 can be instead connected thereto (implantable body also being implanted in the recipient). The resulting implanted portion of the system can be seen in FIG. 25, which corresponds to the arrangement of FIG. 14, with the nomenclature that module 1320 is the old module 1320 (1320 OLD).

In an exemplary embodiment, the old module 1320 (module 1320 OLD—hereinafter, the nomenclature "OLD" will be dispensed with) is configured to accommodate the fact that it no longer receives "raw" RF signals from communication module 1344. Instead, it receives signals that are analogous to indoor the same as the signals that it is internal stimulator (the stimulator of the intelligent actuator) outputs to the actuator. That is, the functionality of the module 1320/the intelligence actuator has been reduced to that of actuator 340 of FIG. 3. In this regard, module 1320 can include a logic circuit, which can be the same logic circuit detailed above or another logic circuit, which detects the signature of the module 1444 in general, and that of the implantable sound processor 730 in particular. Module 1320 is configured such that if the signature is present, the input from module 1444 (the input from the implantable sound processor 730) is directed through an output mapping circuit of the module 1320/intelligent actuator, to the actuator. This is as contrasted to the scenario of use detailed above, where the old module 1320/intelligent actuator decoded the RF signals received from module 1344. That is, because the intelligent actuator is no longer receiving raw RF signals, but instead receiving the refined output of the implantable sound processor 730/the equivalent of output from stimulator unit 320/the stimulator unit of the intelligent actuator, the intelligent actuator need not decode those signals.

Concomitant with the embodiment of FIG. 23, the module 1444 can be configured to embed a code into the output thereof to the intelligent actuator/module 1320. The intelligent actuator/module 1320 can be configured to read that code, and recognize that the intelligent actuator need not decode the signal. That said, in an alternate embodiment, module 1320 can be configured to automatically analyze a given signal, and determine that the signal is or is not an RF signal, and operate accordingly. Also, consistent with the embodiment of FIG. 23, module 1444 can be configured to output a signal to module 1320 instructing module 13202 operate accordingly. Note also that in an exemplary embodiment, consistent with the embodiment of FIG. 23, module 1444 can be configured to output and identification signal to module 1320, and module 1320 can be configured to read that identification signal, and recognize that it is in signal communication with module 1444, and operate accordingly. (Module 2342 can also be configured to output such an identification signal.) Note also that in an exemplary embodiment, module 1320 can be configured to read a memory in module 1444 and/or module 2342 and determine how module 320 should operate accordingly. Any device, system, and/or method that will enable module 1320 to recognize how it should operate based on the fact that it is in communication with another module can be utilized in at least some exemplary embodiments. Corollary to this is that any device, system, and/or method that will enable module 1320 to recognize how it should operate based solely and entirely and only on the fact that it is in communication with another module can be utilized in at least some exemplary embodiments. With regard to these features, at least some of the embodiments detailed herein can have utilitarian value with respect to enabling a given automatic reconfiguration and/or automatic change of operation and/or automatic change of functionality of a first module upon a second module being placed into signal communication with that first module. This as opposed to having a user, such as a healthcare professional, such as a surgeon, reconfigure or otherwise instruct the various modules (e.g., by activating a switch, by programming, etc.) to operate differently.

Figure 24A:
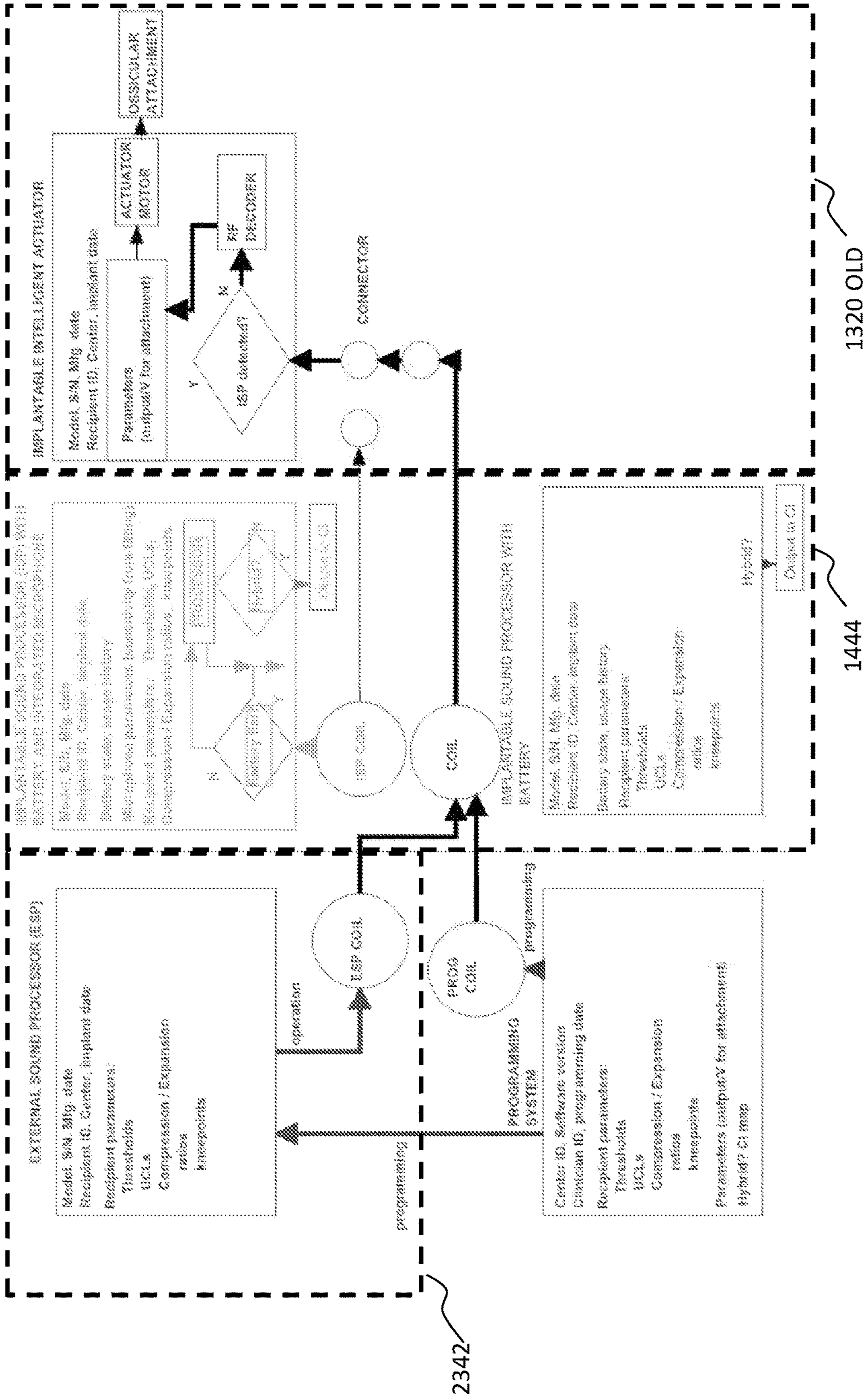
FIG. 24A depicts a functional block diagram of an exemplary system according to an exemplary embodiment with logic details and memory details.
Figure 24B:
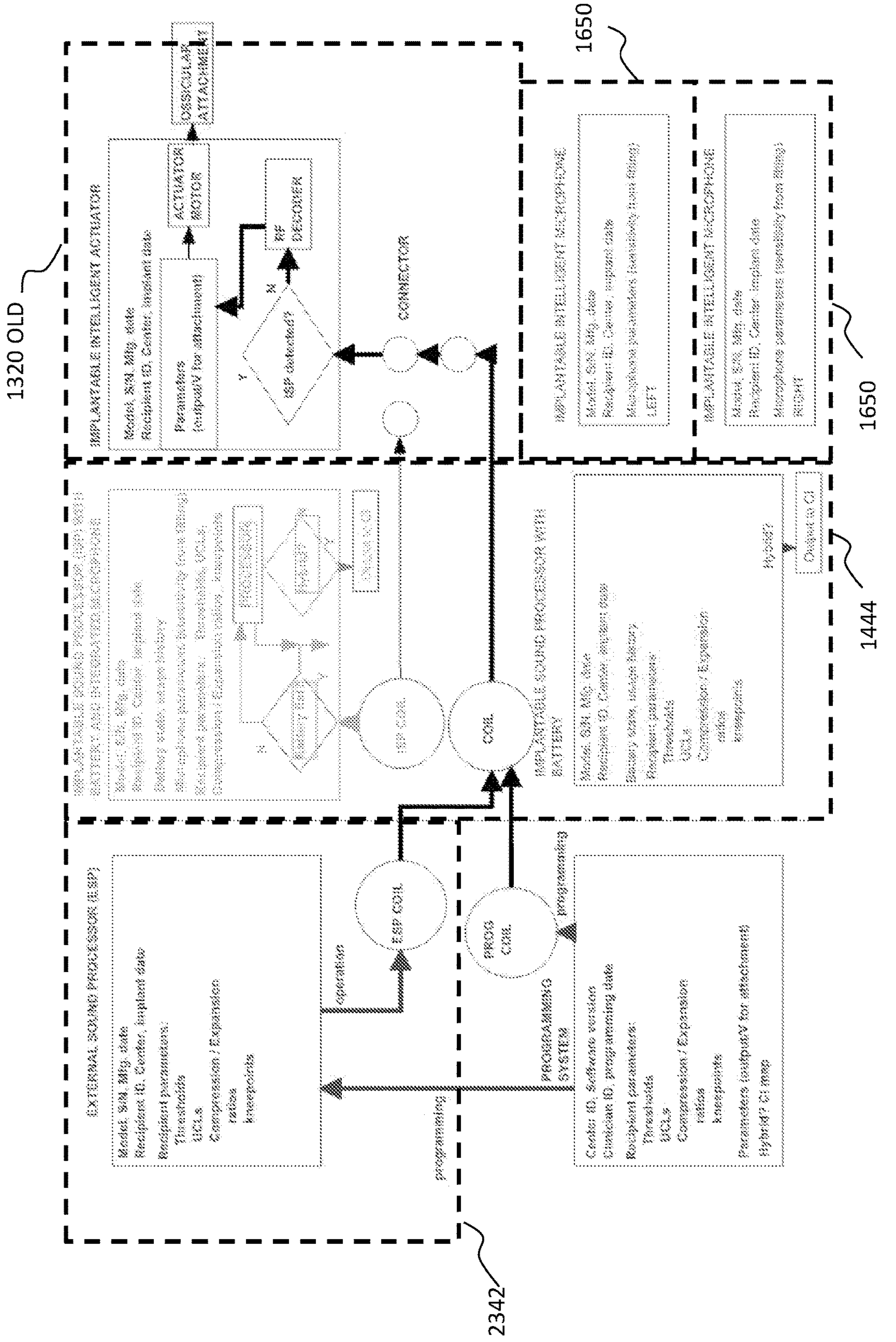
FIG. 24B depicts a functional block diagram of an exemplary system according to an exemplary embodiment with logic details and memory details.
Figure 25:
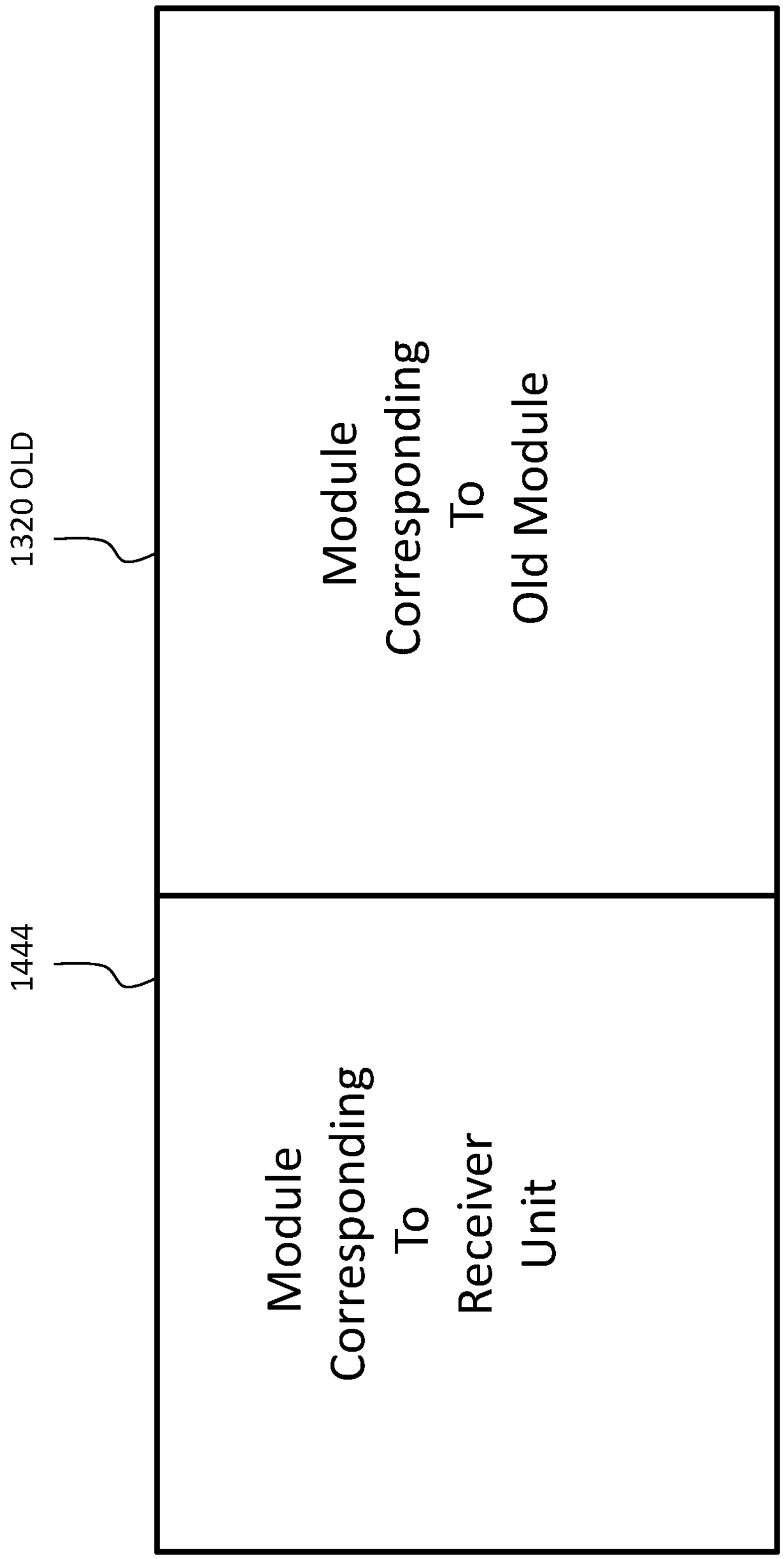
FIG. 25 is a functional block diagram representing an exemplary hearing prostheses according to some of the teachings detailed herein in modularized format.
Figure 26:
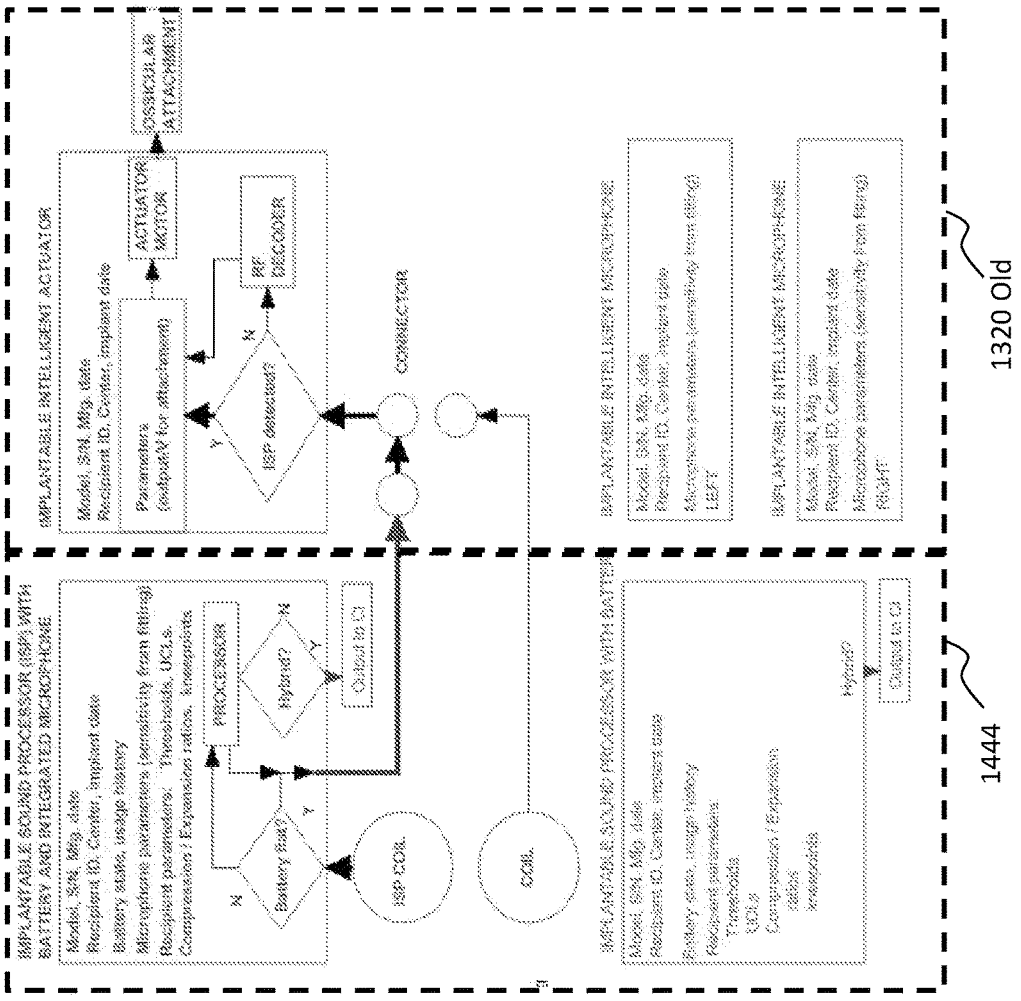
FIG. 26 depicts a functional block diagram of the prosthesis of FIG. 25.

FIG. 26 presents some exemplary logic flow assigning functionality to the given modules according to an exemplary embodiment of the embodiment of FIG. 25 after the embodiment of FIG. 23 is updated to the totally implantable system. It is briefly noted that module 1444 of FIG. 24 is presented with additional details relating to a scenario where module 1444 is instead module 1644, and the remote pendulum microphone 950 is in signal communication therewith. Indeed, in an exemplary embodiment, module 1444 can also be in signal communication with a pendulum microphone 950, as will be detailed below.

Note that FIG. 26 depicts additional details relating to a remote programmer, which details will be provided below.

With regard to FIG. 26, it can be seen that the module 1444, can include such data stored therein, such as in a memory of the like, data relating to the model of the module and/or sound processor, the serial number thereof, the manufacturing date, the recipient ID, the center that such was made and/or the center at where such was implanted, and the implantation date. Module 144 can further include data stored in a memory relating to recipient parameters, such as by way of example only and not by way of limitation, thresholds, UCLs, compression/expansion data, such as ratios and/or kneepoints. In an exemplary embodiment, module 1444 can further include such data as the battery state, the usage history, etc. As will be detailed below, module 1444 can also include a logic circuit to determine if it is being operated in a hybrid mode, and thus can be configured to output signals to a cochlear implant. With respect to the scenario where module 1644 is instead being utilized, any of the aforementioned data associated with module 1444, but directed to module 1644, can be stored therein in the memory of module 1644. Note also that data relating to microphone parameters, such as by way of example only and not by way of limitation, sensitivity data obtained from the fitting process, etc. can be stored in that module 1644. As will be detailed below, module 1444 and/or module 1644 includes a logic circuit that evaluates whether or not the battery is flat or will become flat (a "disablement mode"), as is schematically represented by the flowchart depicted in FIG. 26.*d*

It is noted that in the exemplary embodiment of FIGS. 7 and 14, where the implantable sound processor 730 is integrated with an implantable microphone 740 (e.g., implantable body 744/module 1444 includes both the sound processor 730 and the microphone 740), implantable body 744/module 1444 can include memory, such as nonvolatile memory, in which programming or data or the like is stored at the time of implantation into the recipient. In an exemplary embodiment, the memory can include identifying information that can be available for retrieval at a subsequent temporal period (e.g., serial number, manufacturing date, information about the recipient, such as the recipient ID, the implant center, the implanted dates, the model of the sound processor, the model of the microphone, etc.). Also, the memory can include (as part of, for example, the same block of the nonvolatile memory, or a different block of the nonvolatile memory) fitting parameters specific to the recipient, such as by way of example only and not by way of limitation, thresholds, compression and/or expansion ratios, kneepoints, UCLs, etc.). Any data having utilitarian value with respect to the teachings detailed herein and/or with respect to operating a hearing prosthesis can be utilized or otherwise stored in the memory of the implantable body 744/module 1444.

In an exemplary embodiment of use/implantation, as noted above, module 1320 is the old module. When module 1320 is connected via the connectors 610 to module 1444, in an exemplary embodiment, module 1320 detects the signature of the module 1444 (e.g., the signal processor 730 and output a signature and/or can have a signature they can be read by module 1320, etc.). In an exemplary embodiment, this occurs automatically upon (which includes subsequent) to the establishment of signal communication between module 1444 and module 1320. Upon such occurrence, module 1320 automatically reconfigures itself so as to direct the input from module 1444 to the output mapping circuit and the actuator motor of module 1320. This as opposed to directing the output from module 1444 to the RF decoder circuitry of module 1320. That is, module 1320 automatically reconfigures itself so as to operate in the non-intelligent mode/to operate in a manner akin to the traditional actuator 340 of FIG. 3. That said, alternatively and/or in addition to this, module 1444 is configured to look for module 1320 (or any other module) upon a new module being placed into signal communication there with (analogous to a Windows computer looking for a flash drive). Module 1444 is configured to identify module 1320 when placed into signal communication therewith, and instruct module 1320 to operate in the non-smart mode, or otherwise reconfigure module 1320 such that it will operate in the non-smart mode. Again, unless otherwise specifically detailed herein, in at least some exemplary embodiments, all modules are configured to both instruct or otherwise control another module and be controlled and be instructed by another module. Also, unless otherwise specifically detailed herein, all modules are configured to output data from the memory, and enable the data from the memory to be read. Any permutation of this can enable the reconfigurations of a given module.

In an exemplary embodiment, the above identification/control/reconfigurations, etc. occurs automatically, and is transparent to the surgeon and/or clinician who is implanting the module 1444. In this regard, in an exemplary embodiment, an exemplary method of surgery entails, after obtaining access to the implant system including modules 1344 and 1320, disconnect module 1344 from module 1320, remove module 1344 from the recipient, connect module 1444 to old module 1320, secure module 1444 to tissue of the recipient. In an exemplary embodiment, these are the only method actions executed between the time just before the module 1344 is disconnected from module 1320 to just after the time that module 1444 is secured to tissue of the recipient and/or just after the time that module 1444 is connected to old module 1320 so as to have a fully functioning totally implantable hearing prosthesis in the recipient. In this regard, in an exemplary embodiment, a surgeon or other healthcare professional or the like need not make adjustments for provide input into the module 1320 and/or the module 1444 to make the two modules work with each other so as to establish a hearing percept. That said, in an exemplary embodiment, fitting data or the like from module 2342 could be transferred to module 1444 prior to implantation or after implantation. However, that data simply customizes module 1444 to the recipient. That is, the data makes module 1444 and module 1320 more functional—those modules are already functional and the first instance.

Figure 27:
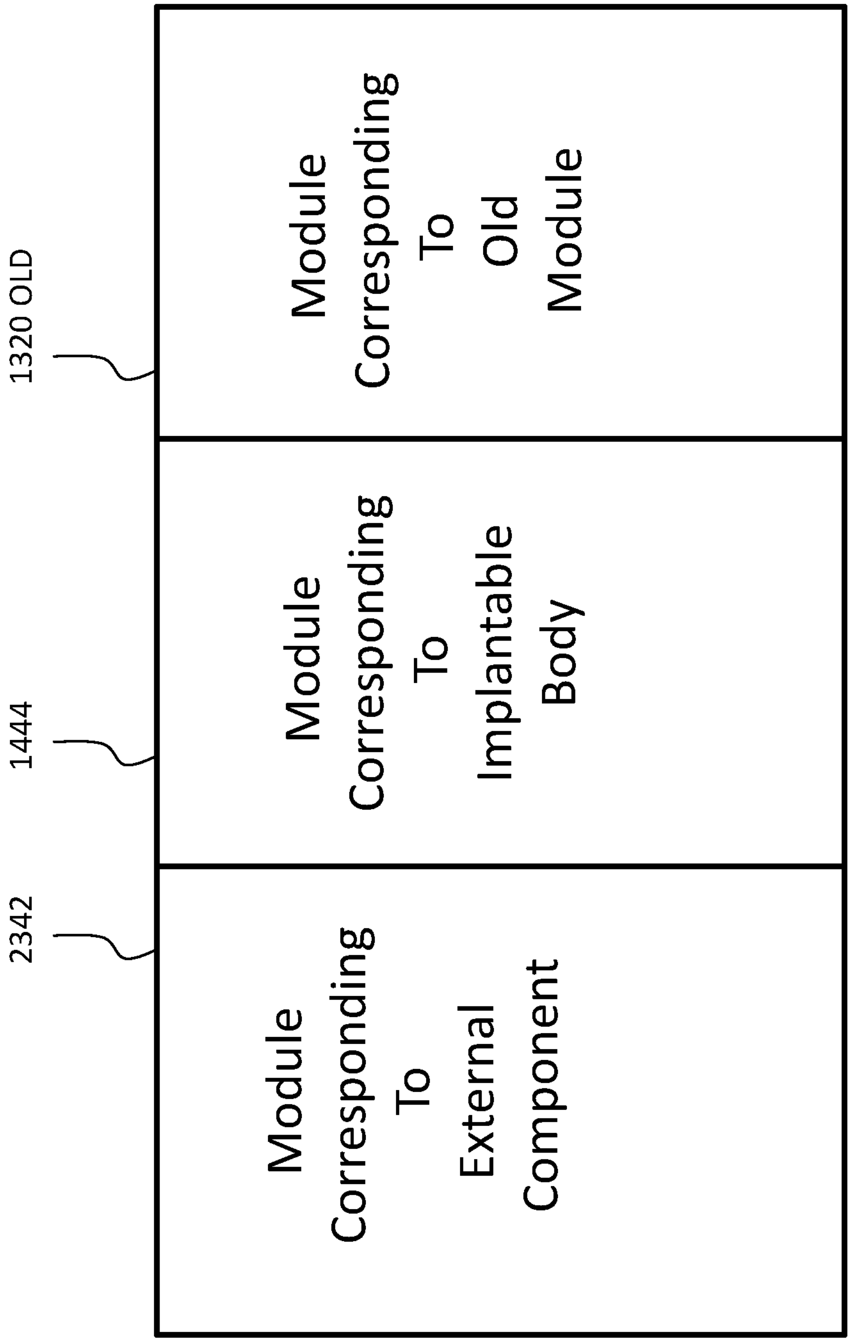
FIG. 27 is a functional block diagram representing an exemplary hearing prostheses according to some of the teachings detailed herein in modularized format.

It is noted that the embodiment of FIGS. 7 and 14 and the embodiments of FIGS. 8 and 15 and 9 and 16 are configured so as to function or otherwise continue to enable the evocation of a hearing percept in the event of a failure or otherwise inability of the implanted sound processor 730. By way of example only and not by way of limitation, in an exemplary embodiment, the implantable battery located in the implantable body 744, 844, and 944 could become discharged, thus preventing the sound processor 730 from being powered. Still further, in an exemplary embodiment, the implantable microphone 740 could fail, and thus, because input to the sound processor based on captured sounds is not available, the sound processor 730 does not have input to process, and thus cannot output useful signals to the actuator 1320. In any event, whatever the "failure mode" or "disable mode," some exemplary embodiments of the totally implantable hearing prostheses are configured to operate in partially implantable mode. For example, FIG. 27 depicts the modules 1444 and 1320 OLD in signal communication with external component/module 2342 of the embodiment of FIG. 3.

FIG. 24A depicts an exemplary logic flow assigning functionality for the various modules of FIG. 27, along with some additional details about an external programming system that will be briefly described in greater detail below. It is briefly noted that as with FIG. 26, module 1444 of FIG. 24 is presented with additional details relating to a scenario where module 1444 is instead module 1644, and the remote pendulum microphone 950 is in signal communication therewith. Indeed, in an exemplary embodiment, module 1444 can also be in signal communication with a pendulum microphone 950, as will be detailed below.

With regard to FIG. 24A, it can be seen that the module 1444, can include such data stored therein, such as in a memory of the like, data relating to the model of the module and/or sound processor, the serial number thereof, the manufacturing date, the recipient ID, the center that such was made and/or the center at where such was implanted, and the implantation date. Module 144 can further include data stored in a memory relating to recipient parameters, such as by way of example only and not by way of limitation, thresholds, UCLs, compression/expansion data, such as ratios and/or kneepoints.

The implanted module 1444 can also include any of the data just detailed with respect to module 2342, but directed to the module 1444. In an exemplary embodiment, module 1444 can further include such data as the battery state, the usage history, etc. Note also that this data can also be present in the module 2342, but directed to module 1444. As will be detailed below, module 1444 can also include a logic circuit to determine if it is being operated in a hybrid mode, and thus can be configured to output signals to a cochlear implant. With respect to the scenario where module 1644 is instead being utilized, any of the aforementioned data associated with module 1444, but directed to module 1644, can be stored therein in the memory of module 1644. Note also that data relating to microphone parameters, such as by way of example only and not by way of limitation, sensitivity data obtained from the fitting process, etc. can be stored in that module 1644. Again, as will be detailed below, module 1444 and/or module 1644 includes a logic circuit that evaluates whether or not the battery is flat or will become flat (a "disablement mode"), as is schematically represented by the flowchart depicted in FIG. 24A.

FIG. 24B presents a schematic representing logic associated with a system that further includes an implantable intelligent microphone (here, two microphones) represented by modules 1650. The utilitarian features of this implantable microphone will be described in greater detail below. However, as can be seen, the implantable intelligent microphone embodied by module 1650 can be placed into signal communication with module 1444 and/or module 1644. The module 1650 can include data related to that implantable microphone along the lines of that related to module 1444 and/or the module 2342. In an exemplary embodiment, information or otherwise data relating to the specific microphone parameters can be stored therein, such as by way of example only and not by way of limitation, the sensitivity data resulting from the fitting operation. Note also that data indicative of the implantation sides of the modules 1650 can also be stored in a memory thereof, such as whether or not the microphone is implanted on the left side or the right side of the recipient, or which side the microphone is implanted, etc. It is noted that the features associated with modules 1650 seen in FIG. 24B are also applicable to the system of FIG. 26 and the other functional logic block diagrams detailed herein and variations thereof.

Here, the module 2342 captures sound and processes that captured sound just as it would have done in the embodiment of 23 prior to conversion of the implant to the fully implantable system. The process sound is converted into a RF signal and transmitted from module 2342 to module 1444, where coil 6100 receives that signal. In this exemplary embodiment, module 1444 is configured to automatically recognize that it is incapable of processing signals from the microphone for whatever reason, and thus is configured to automatically place itself into a pass-through mode so as to pass the signal received by coil 6100 to the actuator 620 (module 1320 OLD). By way of example only and not by way of limitation, a logic circuit within module 1444 can be configured to detect a low battery level or the like, and thus redirect input (or control the components of module 14442 redirect input) from the coil 6100 directly to the actuator 620 (module 1320 OLD). In an exemplary embodiment, module 1444 is configured to automatically instruct module 1320 OLD to treat the signals from module 1444 as RF signals. In an exemplary embodiment, upon the occurrence of the failure mode and/or the disablement mode, module 1444 is configured to automatically provide an indication to module 1320 that it is instead module 1344 (communications unit/receiver unit 644) or otherwise treat signal there from as if those signals were from module 1344. In an exemplary embodiment, module 1444 can be configured to embed a code into the output thereof that will be read by module 1320 OLD such that module 1320 OLD will treat the signal as an RF signal and operate accordingly. Alternatively, and/or in addition to this, in an exemplary embodiment, module 1320 OLD is configured to detect that there exists a code and/or there is an absence of a code in the signal from module 1444, and thus reconfigure itself to operate in the intelligent actuator mode. In an exemplary embodiment, module 1320 OLD is configured to read or otherwise evaluate the status of module 1444, and upon a determination that module 1444 has experienced a failure mode and/or a disablement mode, operate in the intelligent actuator mode.

To be clear, in an exemplary embodiment, there is a method where an implanted battery goes flat or otherwise goes to a low-power state, and the system self-reconfigures into a semi-implantable hearing prosthesis, passing the signal from the external sound processor through to the actuator or to the other intelligent components thereof so as to evoke a hearing percept. In an exemplary embodiment, this action is automatic upon the battery going flat, in an alternate embodiment, this action is automatic when the battery power capacity reaches a low level or otherwise when a low level battery capacity is detected. That said, alternatively, and/or in addition to this, the reconfiguration of the system to a partially or semi implantable hearing prostheses can be executed via a "manual" invocation thereof.

In view of the above, it can be understood that in an exemplary embodiment, there is an implantable device, such as by way of example only and not by way of limitation, an implantable hearing prosthesis, comprising an implantable module (e.g., module 1444), including a first functional component (e.g., sound processor 730). In this exemplary embodiment, the implantable module is configured to effectively differentiate between a plurality of different second functional modules respectively placeable into signal communication with the module. In an exemplary embodiment, the different second functional modules can be selected from the group of the intelligent actuator module 1320, the standard actuator module 1540, the pendulum microphone module 1650 (intelligent or standard microphone), the cochlear implant stimulator module 1020 (intelligent or standard stimulator), etc. Consistent with the teachings detailed above, the implantable module of this exemplary embodiment is configured to analyze respective signals from the plurality of different second modules and determine a respective functionality of the second modules based on the respective signals. In an exemplary embodiment, this corresponds to a scenario where one or more of the second modules outputs an identification signal to the implantable module indicating its functionality or otherwise what module it is (intelligent actuator, pendulum microphone, bone conduction actuator, implantable battery module, etc.). In an exemplary embodiment, this corresponds to a scenario where the implantable module analyzes standard operational signals from these modules with respect to a closed circuit extending between the implantable module and the respective second modules to determine the respective functionality of the second modules. By way of example only and not by way of limitation, with respect to the embodiment where module 1020 is placed into signal communication with module 1444 or another implantable module, module 1444 or another implantable module could analyze the impedance of the given circuit to determine that module 1020 is placed into signal communication therewith. This can also be the case with respect to any of the other modules. For example, with respect to the modules corresponding to the remote pendulum microphones, the implantable module could analyze the signal and recognize, based on the frequency content thereof, that such corresponds to an audio signal, and because the implantable module has logic or otherwise is programmed to recognize that such a signal corresponds to a remote pendulum microphone, determine that the second module is a microphone module. Still further by way of example only and not by way of limitation, with respect to a remote inductance coil module, the implantable module could be configured to analyze the signal and determine that such signal corresponds to an RF signal, and because the implantable module is programmed or otherwise contains logic to identify such a signal as an RF signal, can determine that the module is a inductance coil module. It is noted that in some exemplary embodiments, lookup tables or the like can be utilized. Any device, system, and/or method that can enable the implantable module to analyze respective signals from the different second modules and determine the respective functionality thereof based on the signals can be utilized in at least some exemplary embodiments.

By “effectively differentiate,” it is meant that the implantable module can affirmatively differentiate between different modules placed into signal communication there with (e.g., the module knows that another module is a module for X, Y or Z etc.), and also that the implantable module can affirmatively differentiate between different modules because one module is acting differently than another module and/or that a given module is not providing data or otherwise is not reacting as it would if it was one such module. By way of example only and not by way of limitation, the implantable module could default to a conclusion that any module in signal communication there with that does not have identifying information is a microphone module or an inductance coil module (i.e., a module that does not have an active component). Thus, it would effectively differentiate between modules even though it is not affirmatively identifying the module.

Still further, in an exemplary embodiment, it can be understood that the implantable module is configured to adjust an operational parameter of the functional component based on the effective differentiation. In an exemplary embodiment, such as where the module is the intelligent actuator module 1320, the functional component can be a tissue stimulation device, and the implantable module is configured to enable the tissue stimulation device to operate differently based on the effective differentiation. With reference to the above exemplary scenario, if the intelligent actuator module 1320 determines that it is in signal communication with an inductance coil module corresponding to 1344, the module 1320 will control the tissue stimulation device to operate in the intelligent actuator mode, decode the RF frequencies and develop stimulation/driver output based on those received RF frequencies, which output is provided to the actuator of module 1320 to evoke a hearing percept. Conversely, if the intelligent actuator module 1320 determines that it is in signal communication with an implantable sound processor or the like (even if such determination is simply based on the fact that the signal is not an RF signal, thus effectively differentiating between a signal from an implantable signal processor module and from an implantable inductance coil module), the module 1320 will pass the signal directly to the actuator without the decoding and without generating a stimulator/driver signal. That is, the module 1320 will place the tissue stimulation device into the standard mode of operation. Corollary to this is that in an exemplary embodiment, the implantable module is configured to enable the tissue stimulation device to selectively operate under one of two regimes based on the effective differentiation. In an exemplary embodiment, the first regime of the two regimes is an operation of the tissue stimulating device in a smart device mode (e.g., that which decodes the RF signal and develops a stimulation/driver signal based thereon—the intelligent actuator mode). In an exemplary embodiment, the second regime of the two regimes is an operation of the tissue stimulating device in a slave mode (e.g., module 1320 receives the stimulation/driver signals from module 1444 and operates the actuator based solely on those signals—the standard mode of the intelligent actuator).

By “smart mode,” it is meant a mold in which the module operates in a more autonomous manner than that of the “slave mode.” By “slave mode,” it is meant that the module operates as a slave to the other module. That is, it is controlled by the other module. This is differentiated from operation where the module receives a signal and analyzes the signal and develops an operation mode based on the analysis. Again, with respect to the exemplary embodiment of the smart actuator, the slave mode is that which the intelligent actuator receives stimulation/driver signals and applies those driver signals to the actuator. In an exemplary embodiment of slave mode with respect to an intelligent cochlear implant electrode array (described in greater detail below) would be the receipt by module 1820 of a stimulation signal/drive signal from an implantable sound processor module, where the module 1820 stimulates tissue utilizing the electrode thereof bypassing that stimulation signal/drive signal directly to the electrodes.

Note also that in view of the above, it can be understood that in an exemplary embodiment, there is an implantable system, such as by way of example only and not by way of limitation, the system of FIG. 6, wherein there exists a first implantable module having a first role in the implantable system. By way of example only and not by way of limitation, that can be the module 1320 detailed above, with a role of that of a stimulator/driver combined with actuation functionality. In this exemplary embodiment, this implantable module, such as module 1320, is configured to adopt a second role automatically upon a changed circumstance. In an exemplary embodiment, the second role would be that of a standard actuator where the stimulator/driver functionality has been disabled. Such a changed circumstance can correspond to an upgrade of the prosthesis of which module 1320 is apart from a partially implanted prosthesis to a fully implantable prosthesis. Still further, in an exemplary embodiment, an exemplary implantable system can correspond to that of FIG. 7, where the first implantable module having a first role in the implantable system corresponds to module 1444, where again, module 1444 is configured to adopt a second role automatically upon exchange circumstance. In an exemplary embodiment, the first role would be that of a receiver plus an implantable speech processor, while the second role would be that of a receiver, where the module 1444 would simply pass the RF signals received by coil 610 to the module 1320, such as in the scenario where there is a failure mode or a disablement mode or a degraded mode, etc.

In view of the teachings herein, it is to be understood that in an exemplary embodiment, the first implantable module can include a signature detection functionality to analyze the signal from a module remote from the first module. This implantable first module can be configured such that, based on the analysis of the signal, the first implantable module determines that a circumstance has changed and adopt the second role. Consistent with the teachings detailed herein, in an exemplary embodiment, the first module can be module 1320, where the module 1320 is configured to analyze a signature of the module 1444, and, based on that analyzed signature, determine that it should operate in standard mode as opposed to intelligent actuator mode because there is a signal processor implanted in the recipient signal communication there with.

Still further, it is to be understood that in an exemplary embodiment, there exists an implantable system that includes the aforementioned first module along with a second module, where the second module has a functionality of a tissue stimulator. Again, this can be module 1320 although in other embodiments, this could be other modules as detailed herein. The first role of the first module (e.g., 1444) is that of a sound processor that receives a sound signal from an implantable microphone and wired communication with the sound processor. That first role further includes the ability to output a first control signal to a tissue stimulator in signal communication with the first module to activate the second module (e.g., module 1320) to stimulate tissue based on the first control signal. In an exemplary embodiment, the second role of the first module (e.g., 1444) is that of at least one of: (i) a receiver-stimulator that receives a signal from an external module external to the recipient and provides a stimulator control signal based on the received signal to activate the second module to stimulate tissue; or (ii) a pass-through device that receives the signal from the external module external to the recipient and provides the signal to the second module to activate the second module to stimulate tissue based on the received signal.

Corollary to the teachings above, in an exemplary embodiment, the system includes a second module in signal communication with the first module. The first implantable module is configured to send a first signal to the second module indicating the functionality of the first module. The second module is configured to automatically adapt itself to function differently upon receipt of the first signal so that the second module is operationally compatible with the first module. In an exemplary embodiment, the first module can be module 1444, and the second module can be module 1320, where module 1320 adapts itself to function as a standard actuator as opposed to an intelligent actuator upon receipt of this first signal. That said, that first signal can be a signal from the module 1444 indicating that the actuator 1320 should operate in the intelligent actuator mode, because there exists a disablement mode and/or a failure mode of module 1444. Still further, the first module can be an external component of the hearing prostheses, as will now be described.

While the embodiments detailed above have been directed towards the scenario where module 1444 experiences some type of failure mode and/or disablement mode, in an alternate embodiment, there need not be some form of failure mode and/or disablement mode to result in the configuration of FIG. 27. By way of example only and not by way of limitation, a recipient may find that the sound quality of a hearing percept based on the implanted microphone is not as utilitarian as that which might be the case from a microphone located external to the recipient. In this regard, the recipient may place the module 2342 against his or her head, and thus establish signal communication between module 2342 and module 1444. In an exemplary embodiment, module 1444 can be configured to identify the presence and/or absence of module 2342, and thus reconfigure itself to operate in the aforementioned pass-through mode instead of the sound processing mode. In an exemplary embodiment, codes can be provided from a signal from module 2342 instructing module 1444 to operate in the pass-through mode. In an exemplary embodiment, module 2342 can simply instruct module 1444 to operate in the pass-through mode.

Corollary to all of the above is that in an exemplary embodiment, there is an implantable module that can differentiate between modules as detailed above, where the implantable module is configured to differentiate between an implantable signal processor and an external signal processor based on a received signal (whether that signal is automatically generated from the implantable signal processor module with the external signal processor module, or whether that signal is a result of an interrogation by the implantable module of the external signal processor module or the implantable signal processor module).

Note also that in some alternate embodiments, module 1444 can be configured to provide signals based on sound captured by both the external module 2342 and the implantable module 1444. The intelligent actuator 620 (module 1320 OLD) can be configured to receive both signals perhaps in an interleave manner or the like, or via separate leads, and evaluate the signals and determine which signal should be utilized to evoke a hearing percept. Indeed, the signals can arrive from two separate sources entirely (i.e., one signal may never pass through module 1444).

Figure 28:
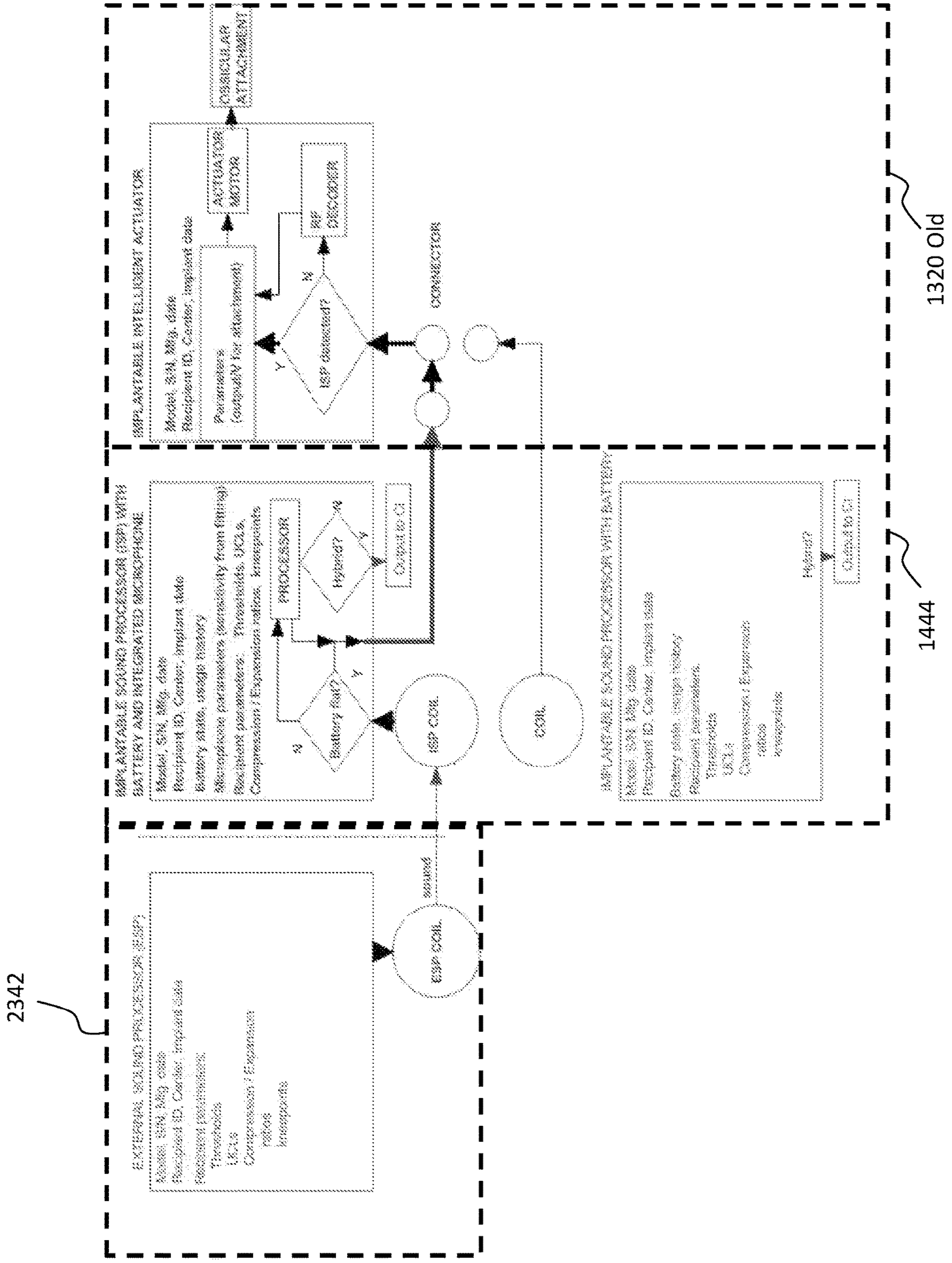
FIG. 28 depicts a functional block diagram of the prosthesis of FIG. 26.

FIG. 28 depicts an exemplary logic flow assigning functionality to the various modules of the embodiment of FIG. 27. FIG. 28 depicts the various information/data stored in the memories of the various modules, concomitant with FIGS. 24A, 24B and 26 detailed above. Is noted that any of the information/data presented in the logic flow diagrams can be information/data stored in the memory of the module.

Figure 29:
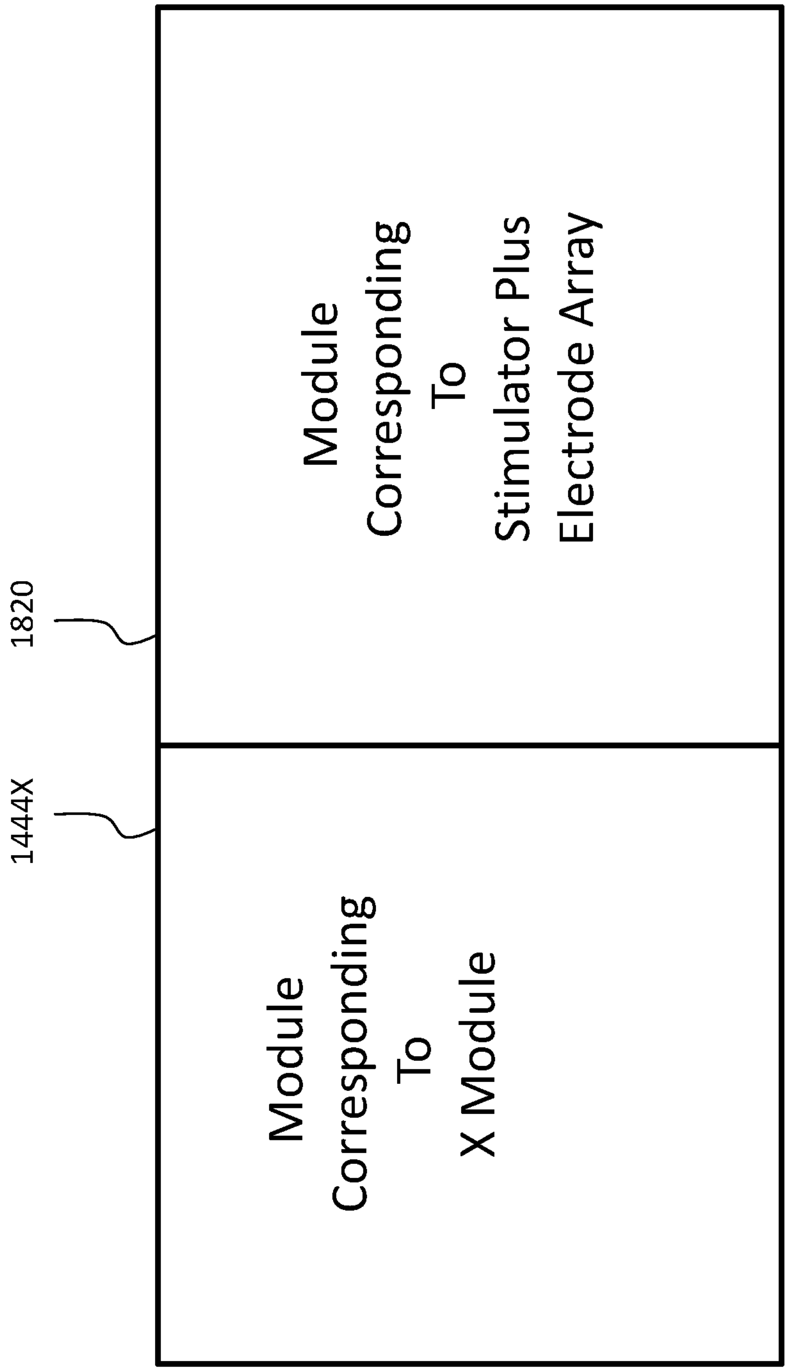
FIGS. 29-33 are functional block diagrams representing various exemplary hearing prostheses according to some of the teachings detailed herein in modularized format.
Figure 30:
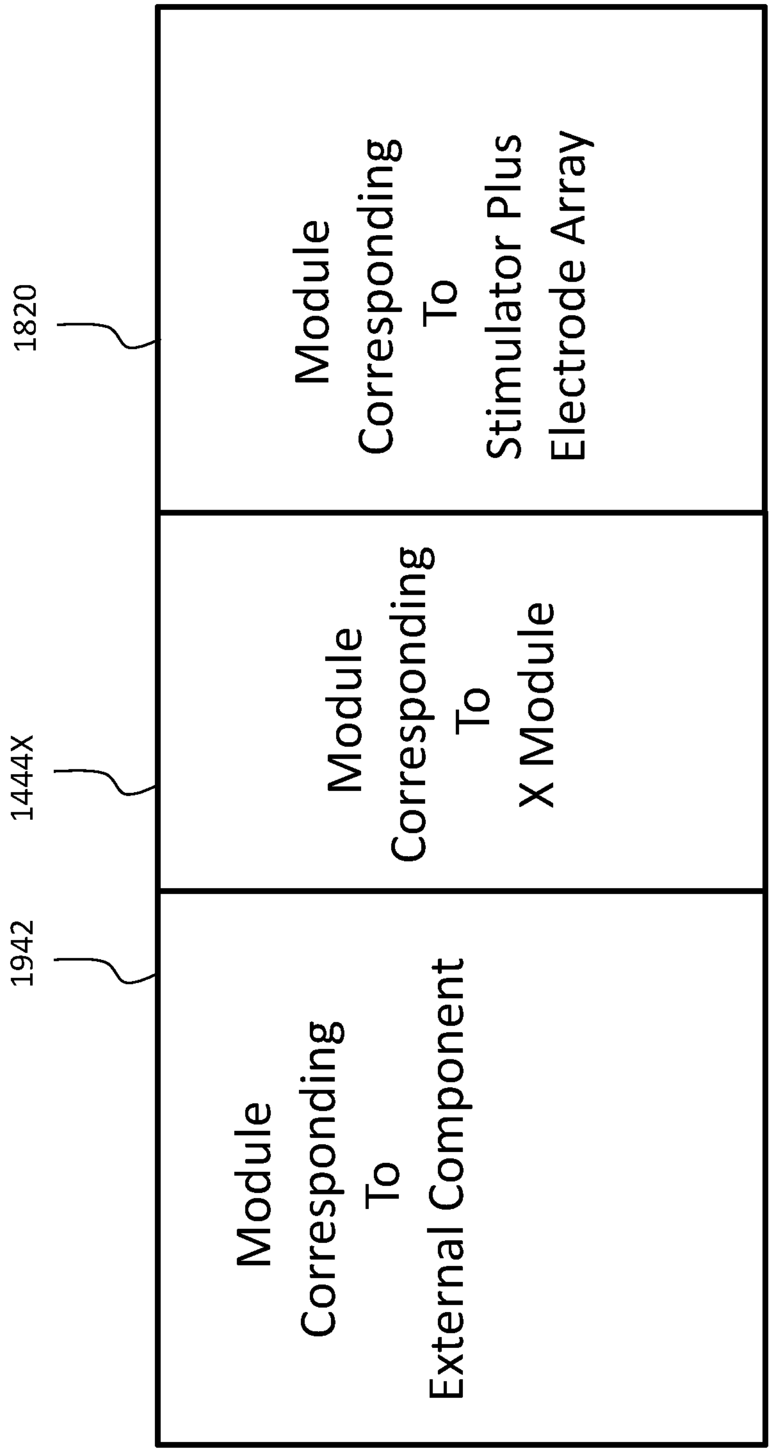

It is noted that while the teachings detailed above have been directed towards the conversion of a middle ear implant from a partially implantable hearing prosthesis to a fully implantable hearing prosthesis, these teachings can be also applicable to other types of hearing prostheses, such as by way of example only and not by way of limitation, cochlear implants and bone conduction devices. In this regard, FIG. 29 depicts an exemplary functional block diagram of a totally implantable hearing prosthesis in modularized format. Referring back to FIG. 11 and FIG. 18, in an exemplary embodiment, module 1344 is removed or otherwise explanted, and module 1444X is placed in signal communication with module 1820, where module 1820 is not removed from the recipient in view of the known risks of explaning and then implanting another cochlear electrode array in the cochlea. Module 1444X can correspond to module 1444 detailed above, which can correspond to implantable body 744, except that the sound processor 730 is instead a sound processor for a cochlear implants, and the output of such sound processor is not that which is utilized to drive an actuator, but instead that which is utilized to energize the electrodes of the electrode array. Any of the identification and reconfiguration and adjustments in operation detailed above with respect to the middle ear implant owing to the replacement of one module with another module are applicable to the embodiments associated with FIG. 29, at least as those teachings would be modified so as to implement such with a cochlear implant. Indeed, FIG. 30 depicts an exemplary scenario where the module 1444X has experienced a failure mode and/or a deactivation mode as detailed above or another variation thereof, or otherwise the recipient has deemed sound captured by an external microphone to be more utilitarian value in a given instance, and thus module 1942 is in signal communication with module 1444X, the effects of which are the same as or otherwise analogous to those detailed above when module 2342 is utilized in the embodiment of FIG. 27.

With reference back to FIG. 20, it is noted that the teachings detailed herein are applicable to so-called hybrid systems. In an exemplary embodiment, the recipient initially is implanted with a system corresponding to that of FIG. 6, 7, 8, or 9 (a middle ear implant). However, as the recipient ages, the ability of the cochlea to evoke a hearing percept based on waves of fluid motions therein for higher frequency sounds becomes degraded. Still, the cochlea remains in a state where it can evoke a hearing percept based on waves of fluid motions therein for the medium and/or lower frequencies sounds. Thus, a decision is made to add a cochlear implant to the existing system. For the exemplary scenario presented herein, it will be assumed that the recipient begins with a partially implantable hearing prosthesis according to FIG. 6, with a BTE sound processor utilized as the external component. This is represented by way of block diagrams in a modular form by FIG. 31, where module 3142 corresponds to a BTE sound processor, module 3144 corresponds to the receiver unit, and module 3120 corresponds to the intelligent actuator. In this regard, FIG. 31 corresponds to the embodiment of FIG. 23, except that the external component is a BTE device as opposed to a button sound processor.

Figure 31:
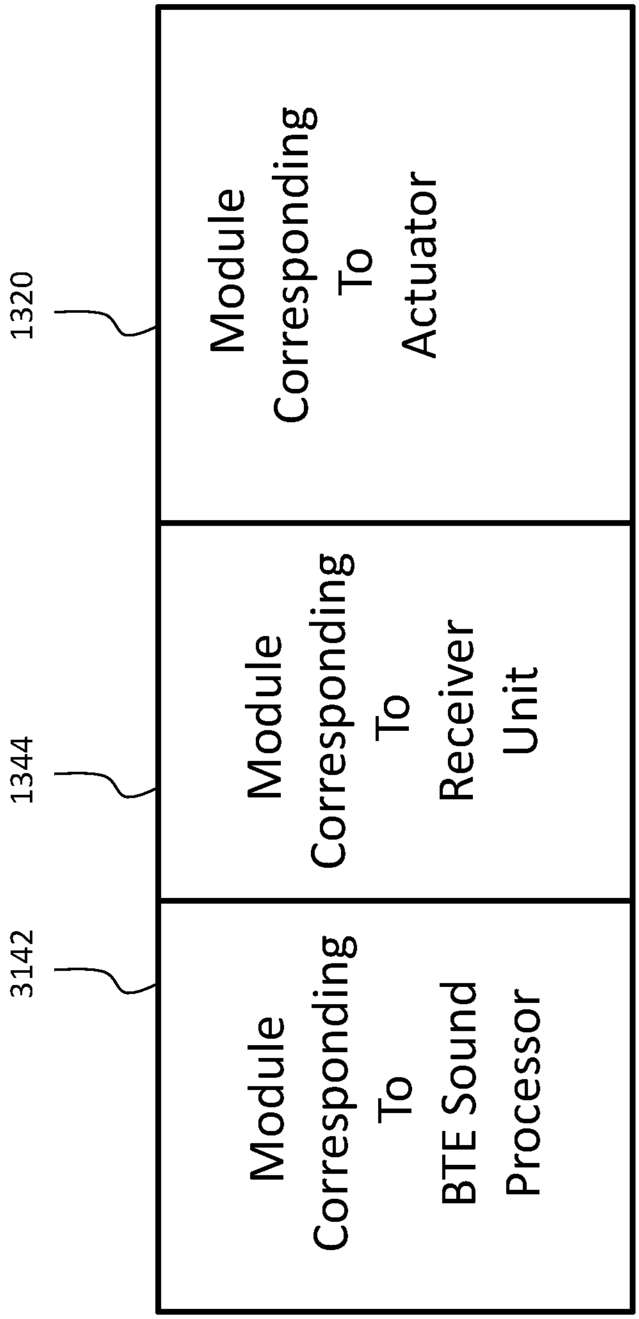

Subsequent to use of the embodiment corresponding to FIG. 31, the system is upgraded to a hybrid hearing prosthesis. Modules 3142 and 3144 are removed from the system, and modules 1344 and 1820 are added to the system by way of implantation. Here, module 1344 corresponds to communications unit 644, except that this communications unit has two outputs or otherwise includes two connectors, one connector for module 1320, and one connector for module 1820. Module 1820 corresponds to the stimulator 1020 and electrode array 1030 of FIG. 11. Module 3299 is also added, which corresponds to a BTE device configured to serve as an external component of a hybrid prosthesis.

Figure 33:
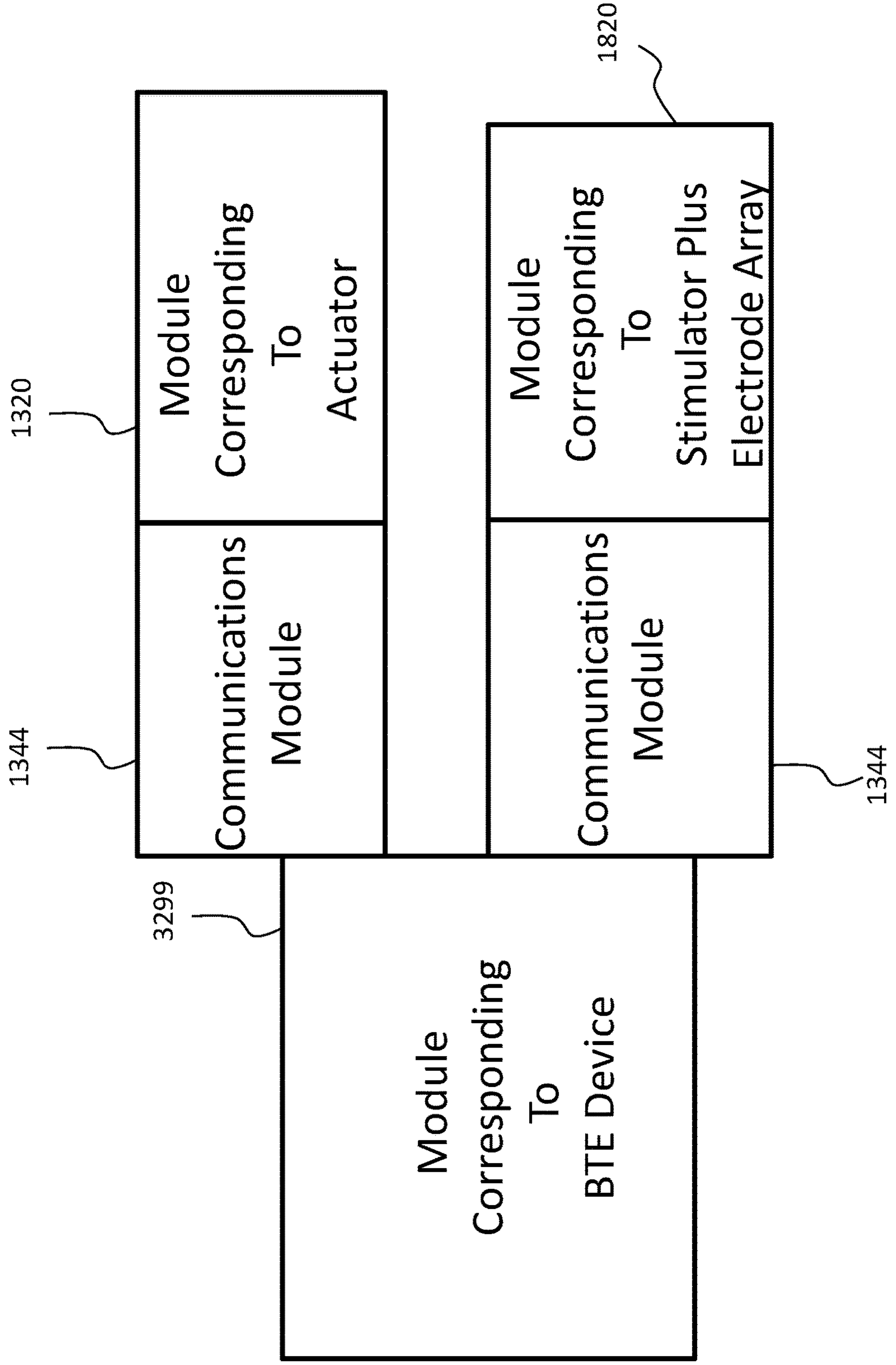

Briefly, it is noted that in an alternative embodiment, instead of a communication unit that communicates with both of modules 1320 and 1820, in an alternate embodiment, two separate communication modules 1344 are provided, as can be seen in FIG. 33.

In an exemplary embodiment, the external component 3299 is configured to recognize module 1320 and/or module 1820 upon the establishment of signal communication therewith. In an exemplary embodiment, the external component 3299 is configured with logic or otherwise circuitry so as to encode or otherwise manipulate the output such that the lower and/or medium frequency range signals outputted by module 3299 are utilized only by module 1320, and the high frequency and possibly the medium frequency range signals outputted by module 3299 are utilized only by module 1820 (or at least there is some form of bifurcation of the output, where possible overlap can exist). Concomitant with the teachings detailed above, the external module 3299 can be configured to read or otherwise access memory in the modules 1320 and/or 1820 so as to identify those modules and determine how the output of module 3299 should be managed so that the respective modules operate according to their respective functions vis-à-vis the hybrid arrangement (e.g., evoke a hearing percept at different frequencies). Still further, alternatively and/or in addition to this, the external module 3299 can be configured so that the modules 1320 and/or 1820 can read the memory therein and determine that module 3299 is an external component of a hybrid hearing prostheses so that those modules can operate accordingly. Note also that in some exemplary embodiments, module 1320 and/or module 1820 can be configured to recognize and/or be recognized by the other of module 1320 and/or module 1820. Such can occur via signal communication through module 1344A or through modules 1344 and module 3299.

Still, in an exemplary embodiment, a logic circuit within module 3299 can be configured to detect the presence of the module 1820 via the transcutaneous inductance link established with the pertinent communication module. Alternatively, and/or in addition to this, that logic circuit or another logic circuit within module 3299 can be configured to detect the presence of module 1320 via the transcutaneous inductance link established with the pertinent communication module. Upon such detection, the module 3299 can automatically configure itself to operate in a hybrid mode, or more accurately, to output signals so that modules 1320 and module 1820 will operate in the hybrid mode.

Figure 32:
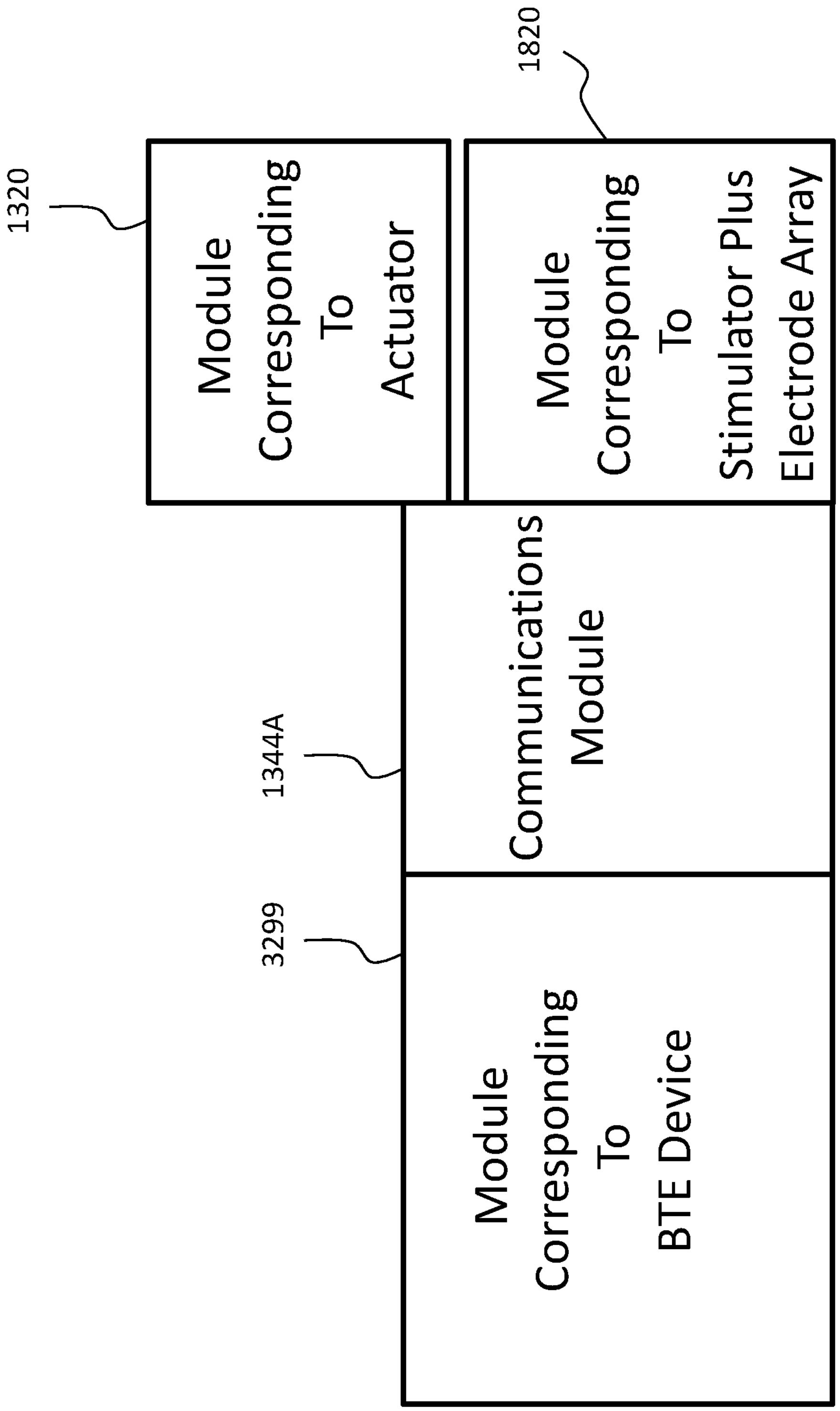

Any of the techniques detailed herein to enable automatic recognition of one module by another module or otherwise automatic reconfiguration of one module or otherwise automatic change of operation, etc. of a module as a result of that module being placed into signal communication with another module can be utilized in the embodiment of FIGS. 31 and 32.

Note that while the aforementioned embodiment entailing upgrading to a hybrid system has been directed towards a partially implantable hearing prosthesis, in an exemplary embodiment, such can also be the case with a fully implantable hearing prosthesis. In this regard, the recipient begins with a partially implantable hearing prostheses according to FIGS. 7 and 14. This is represented by way of block diagrams in a modular form by FIG. 14, as noted above.

Figure 34:
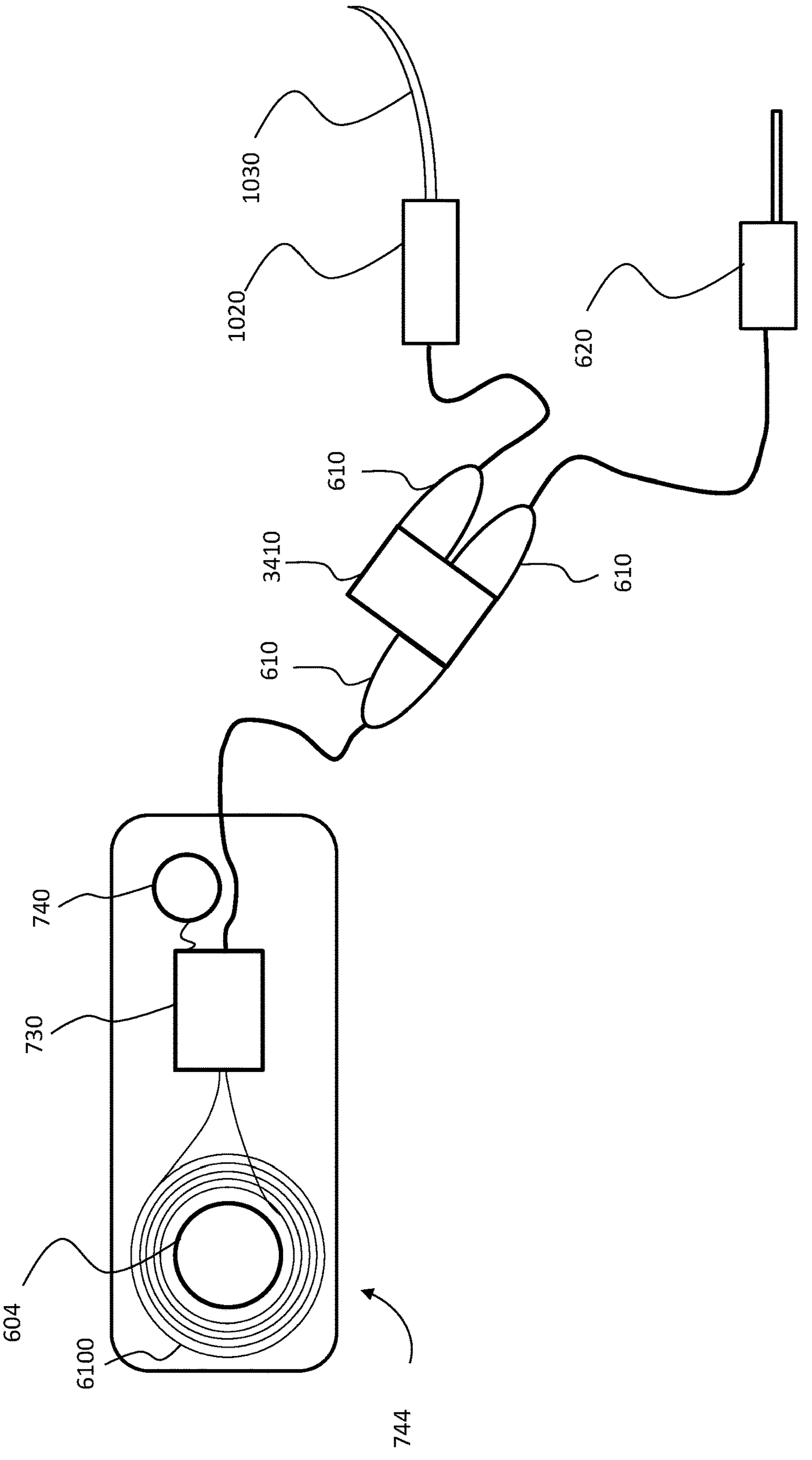
FIG. 34 is a perspective view of an exemplary implantable system according to an exemplary embodiment.
Figure 35:
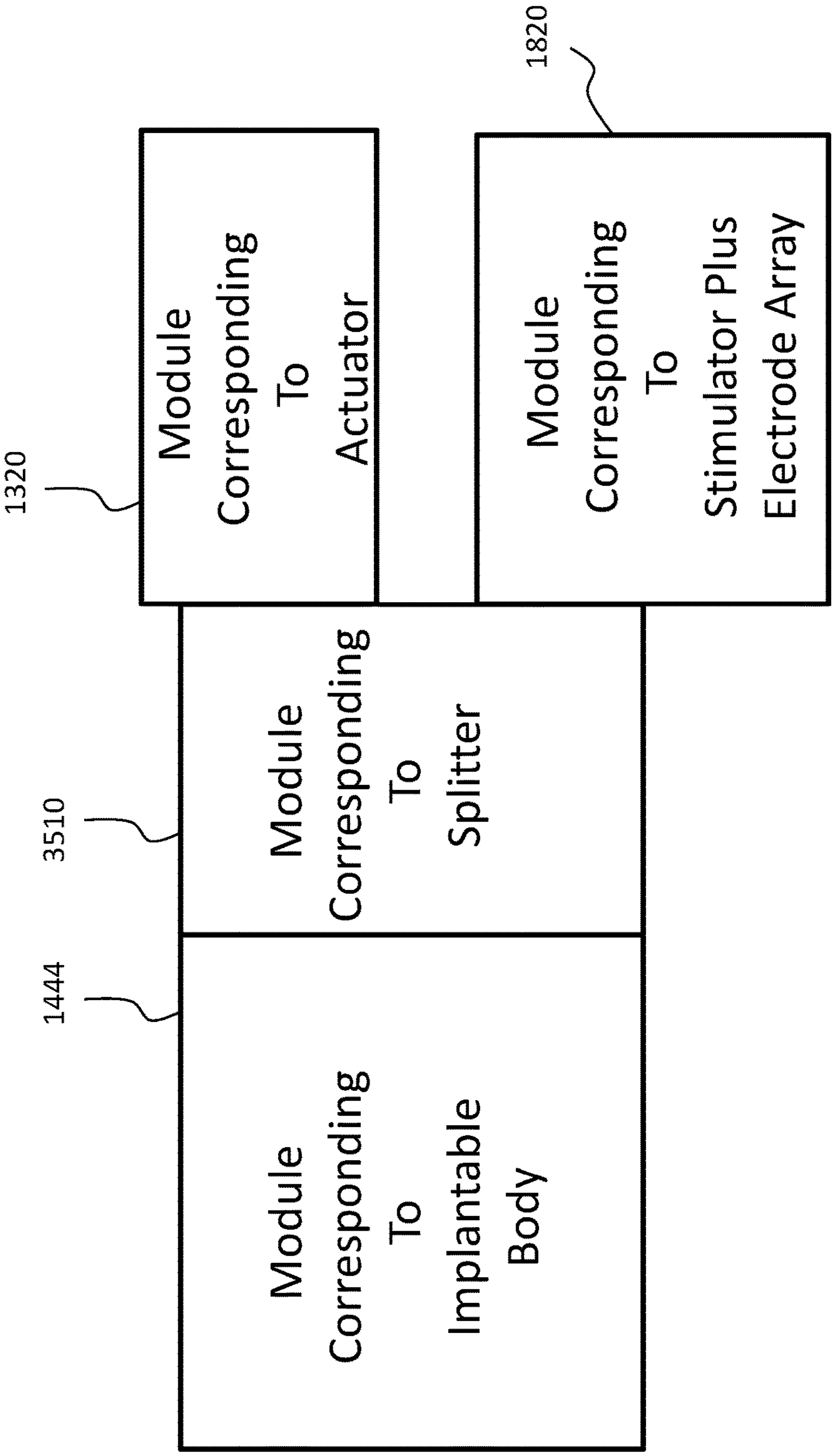
FIGS. 35-36 are functional block diagrams representing various exemplary hearing prostheses according to some of the teachings detailed herein in modularized format.

Subsequent to use of the embodiment corresponding to FIG. 14, the system is upgraded to a hybrid hearing prosthesis. Here, a splitter 3410 is added to the connector 610 as seen in FIG. 34 so as to enable the intelligent actuator 620 and the stimulator 1020 be placed into signal communication with the implantable body 744. FIG. 35 depicts the modularized system, where module 3510 corresponds to the splitter 3410.*d*

Briefly, it is noted that in an alternative embodiment, instead of utilizing a splitter that communicates with both of modules 1320 and 1820, in an alternate embodiment, two (or more) separate connectors can be provided with respect to module 1444 (implantable body 722). Indeed, FIG. 9 depicts such an exemplary embodiment, albeit where the second connector is connected to the remote microphone/pendant microphone 950. In this regard, module 1444 could instead be module 1644 of FIG. 16, with the appropriate modifications to the sound processor 730 and the addition of a microphone in implantable body 944.

In an exemplary embodiment, module 1444 is configured to recognize module 1320 and/or module 1820 upon the establishment of signal communication therewith. In an exemplary embodiment, the module 1444 is configured with logic or otherwise circuitry so as to encode or otherwise manipulate the output such that the lower and/or medium frequency range signals outputted by module 1444 are utilized only by module 1320, and the high frequency and possibly the medium frequency range signals outputted by module 1444 are utilized only by module 1820 (or at least there is some form of bifurcation of the output, where possible overlap can exist). Concomitant with the teachings detailed above, the module 1444 can be configured to read or otherwise access memory in the modules 1320 and/or 1820 so as to identify those modules and determine how the output of module 1444 should be managed so that the respective modules operate according to their respective functions vis-à-vis the hybrid arrangement (e.g., evoke a hearing percept at different frequencies). Still further, alternatively, and/or in addition to this, the external module 1444 can be configured so that the modules 1320 and/or 1820 can read the memory therein and determine that module 1444 is an implantable sound processor of a hybrid hearing prosthesis so that those modules can operate accordingly. Note also that in some exemplary embodiments, module 1320 and/or module 1820 can be configured to recognize and/or be recognized by the other of module 1320 and/or module 1820. Such can occur via signal communication through module 3510 or through module 1444

Still, in an exemplary embodiment, a logic circuit within module 1444 can be configured to detect the presence of the module 1820 via signal communication established with the pertinent communication module. Alternatively, and/or in addition to this, that logic circuit or another logic circuit within module 1444 can be configured to detect the presence of module 1320 via the establishment of signal communication established with the pertinent communication module. Upon such detection, the module 1444 can automatically configure itself to operate in a hybrid mode, or more accurately, to output signals so that modules 1320 and module 1820 will operate in the hybrid mode.

Any of the techniques detailed herein to enable automatic recognition of one module by another module or otherwise automatic reconfiguration of one module or otherwise automatic change of operation, etc. of a module as a result of that module being placed into signal communication with another module can be utilized in the embodiment of FIGS. 34 and 35.

It is noted that in an exemplary embodiment, there can be a dedicated output from the implant body 744 in general, and from the signal processor 730 in particular, to the cochlear implant module 1820, and another dedicated output from the implant body 744 in general, and from the signal processor 730 in particular, to the intelligent actuator module 1320. Such dedicated outputs can provide audio signals or signals based on audio data to the respective modules.

It is noted that in an exemplary embodiment, the implantable body 744 can be configured with a logic circuit that detects the presence of the various modules based on, for example, the characteristic input impedances thereof.

Figure 36:
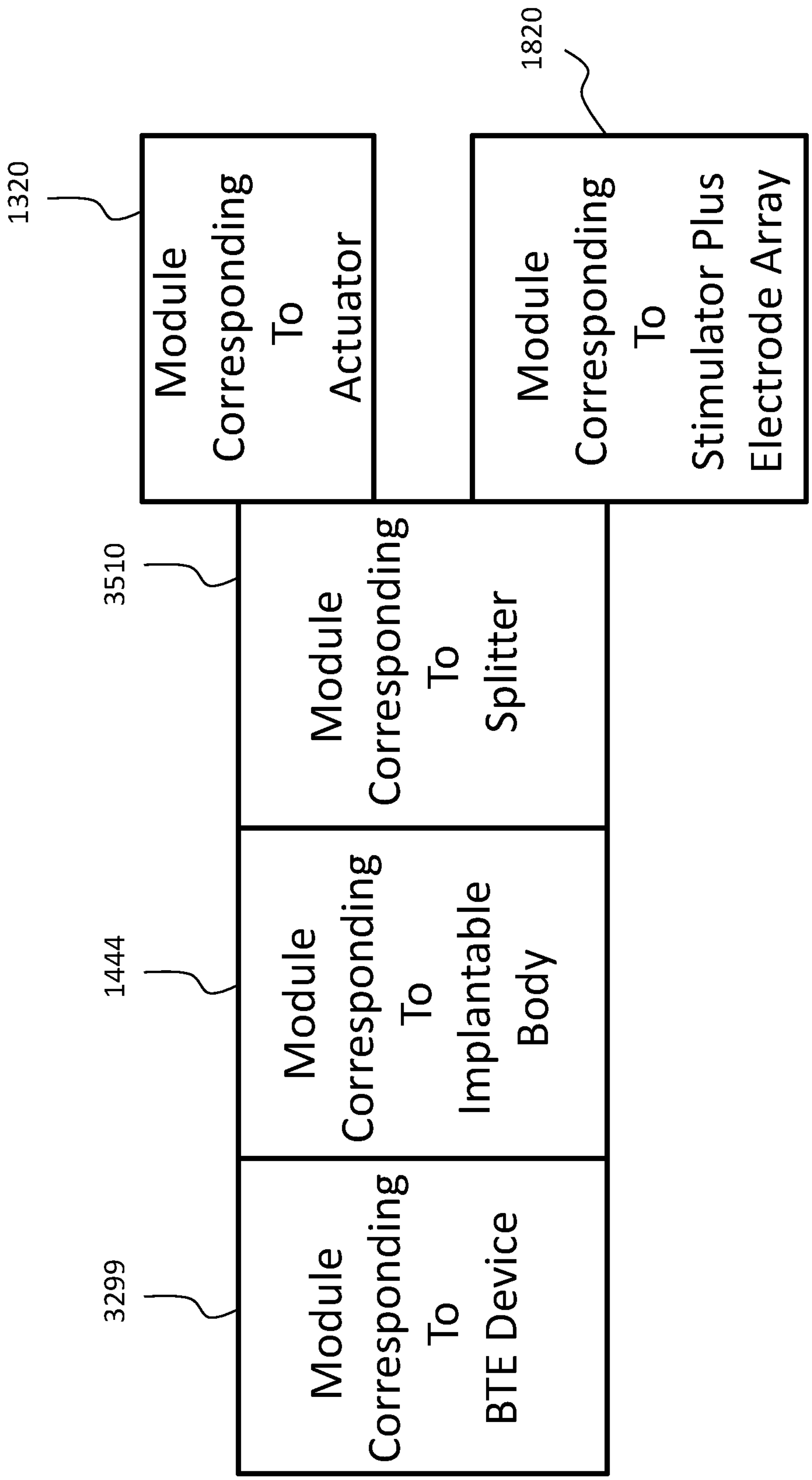

It is briefly noted that the embodiment of FIGS. 34 and 35 can be used in conjunction with an external sound processor as well. FIG. 36 depicts an exemplary system in modular format including module 3299 in signal communication with module 1444. Concomitant with the teachings detailed above with respect to a failure mode and/or a deactivation mode of a totally implantable system, or just a desire on the part of the recipient utilizing an external microphone, the external component 3299 can function in a manner analogous to or otherwise the same as the external component detailed above when such component is placed into signal communication with the implantable module including the implantable sound processor. Corollary to this is that module 1444 and/or the other modules of the system of FIG. 36 can function in a manner analogous to or otherwise the same as the implantable modules detailed above when the external module 3299 and placed into signal communication with module 1444.

Figure 37:
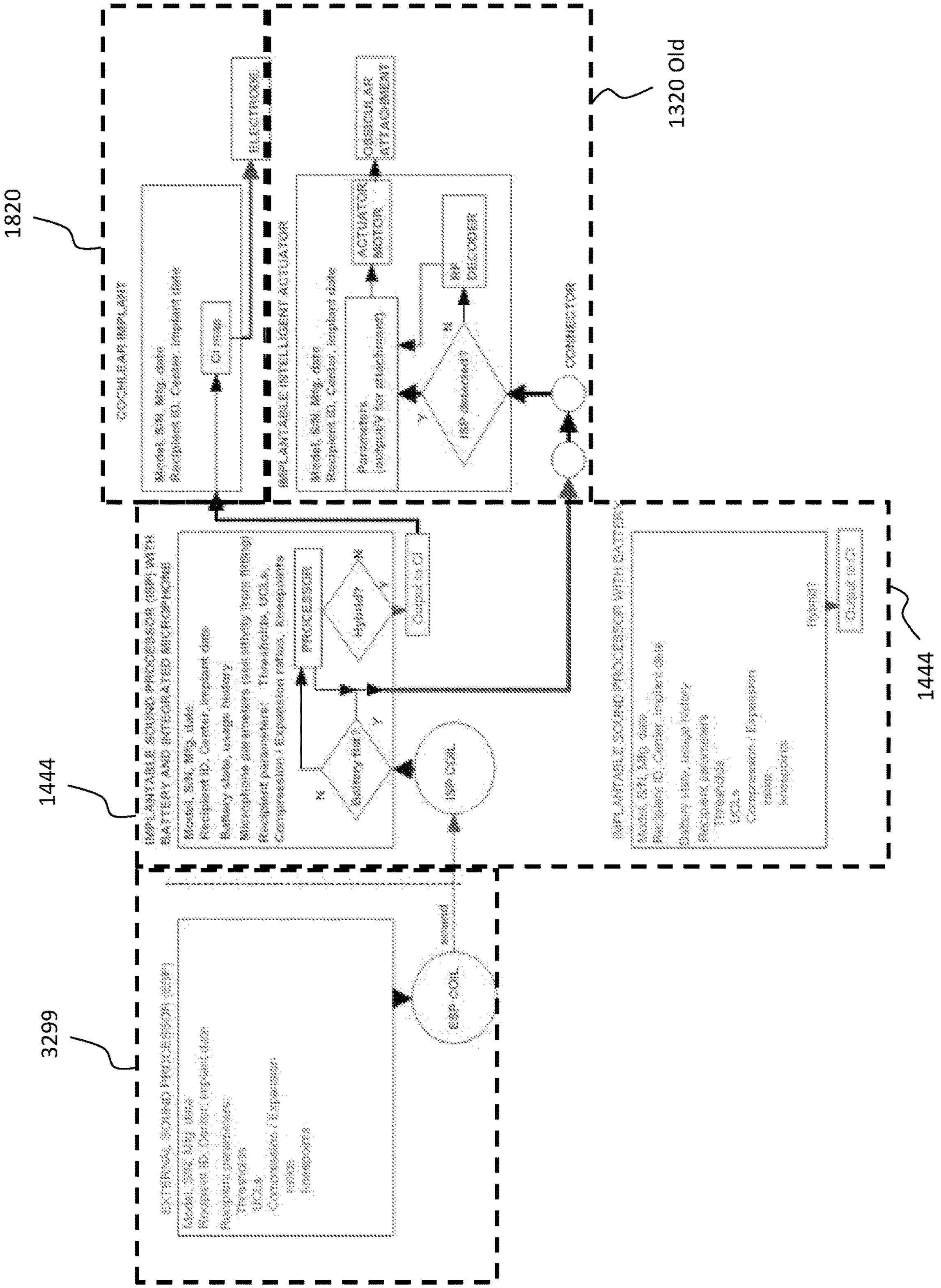
FIG. 37 depicts a functional block diagram of an exemplary system according to an exemplary embodiment with logic details and memory details.

FIG. 37 depicts an illustration of the logical flow assigning function to the various modules of the embodiment of FIG. 36 according to an exemplary embodiment.

Figure 38:
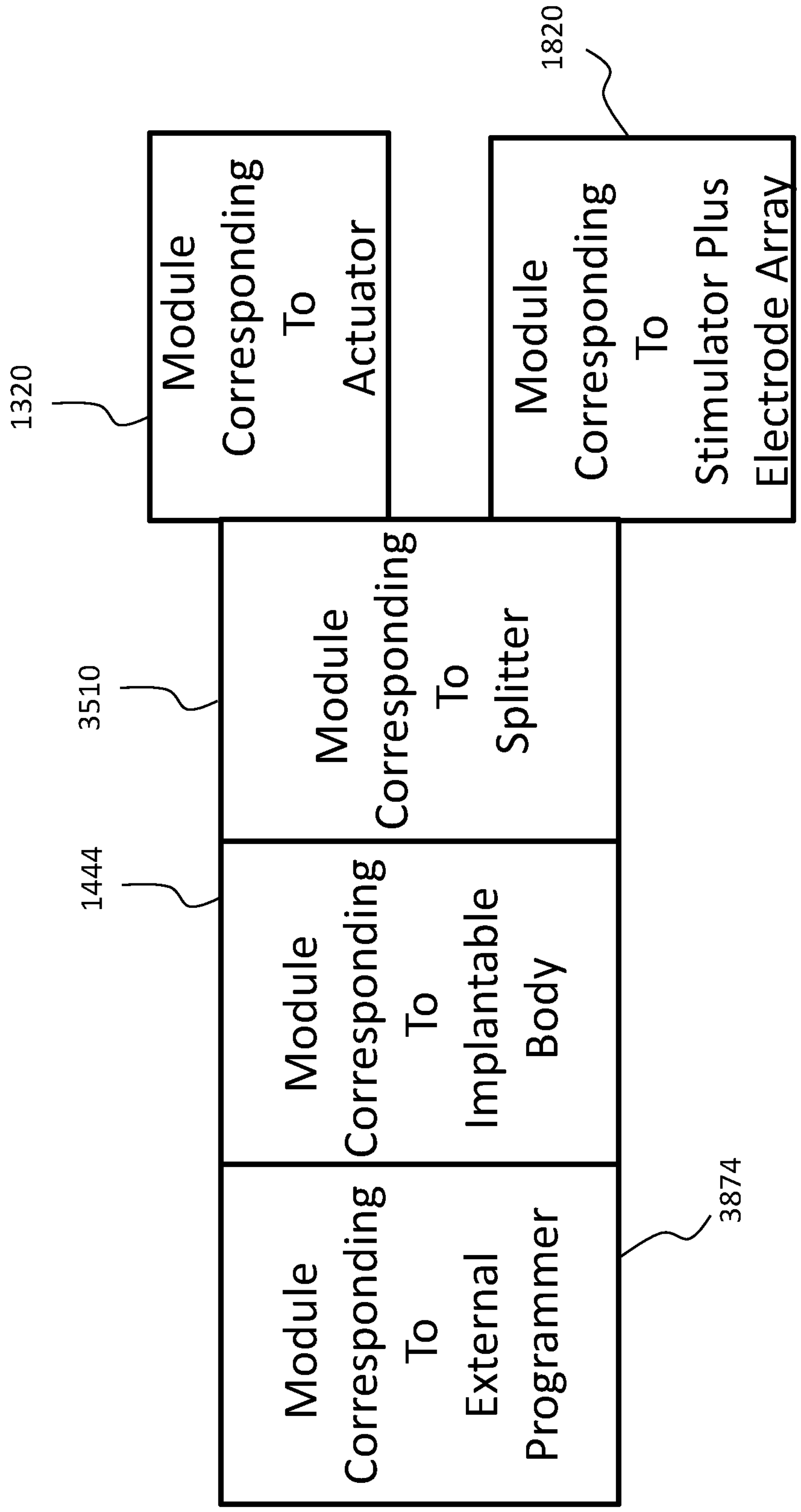
FIG. 38 are functional block diagrams representing various exemplary hearing prostheses according to some of the teachings detailed herein modularized format.

It is briefly noted that some exemplary embodiments include the utilization of a so-called external programmer. In an exemplary embodiment, the external programmer passes instructions to one or more modules of the implant system or otherwise provides data to one or more modules of the implant system so as to have an efficacious use thereof. FIG. 38 depicts an exemplary module 3874 corresponding to an external programmer that is placed into signal communication with the implantable module 1444 of the embodiment of FIG. 35. In an exemplary embodiment, the external programmer/module 3874 can be configured to provide programming instructions or otherwise data to module 1444, which then passes that information/data on to module 1820. In an exemplary embodiment, module 1820 is configured to create a cochlear implant map for the implanted electrodes based on that data. Alternatively, and/or in addition to this, the module 3874 (the external programmer) can provide data or instructions, etc. to the cochlear implant module 1820 so as to add specific parameters to that module, such as by way of example only and not by way of limitation, a group delay adjustment and/or a cutoff frequency etc.

Figure 39:
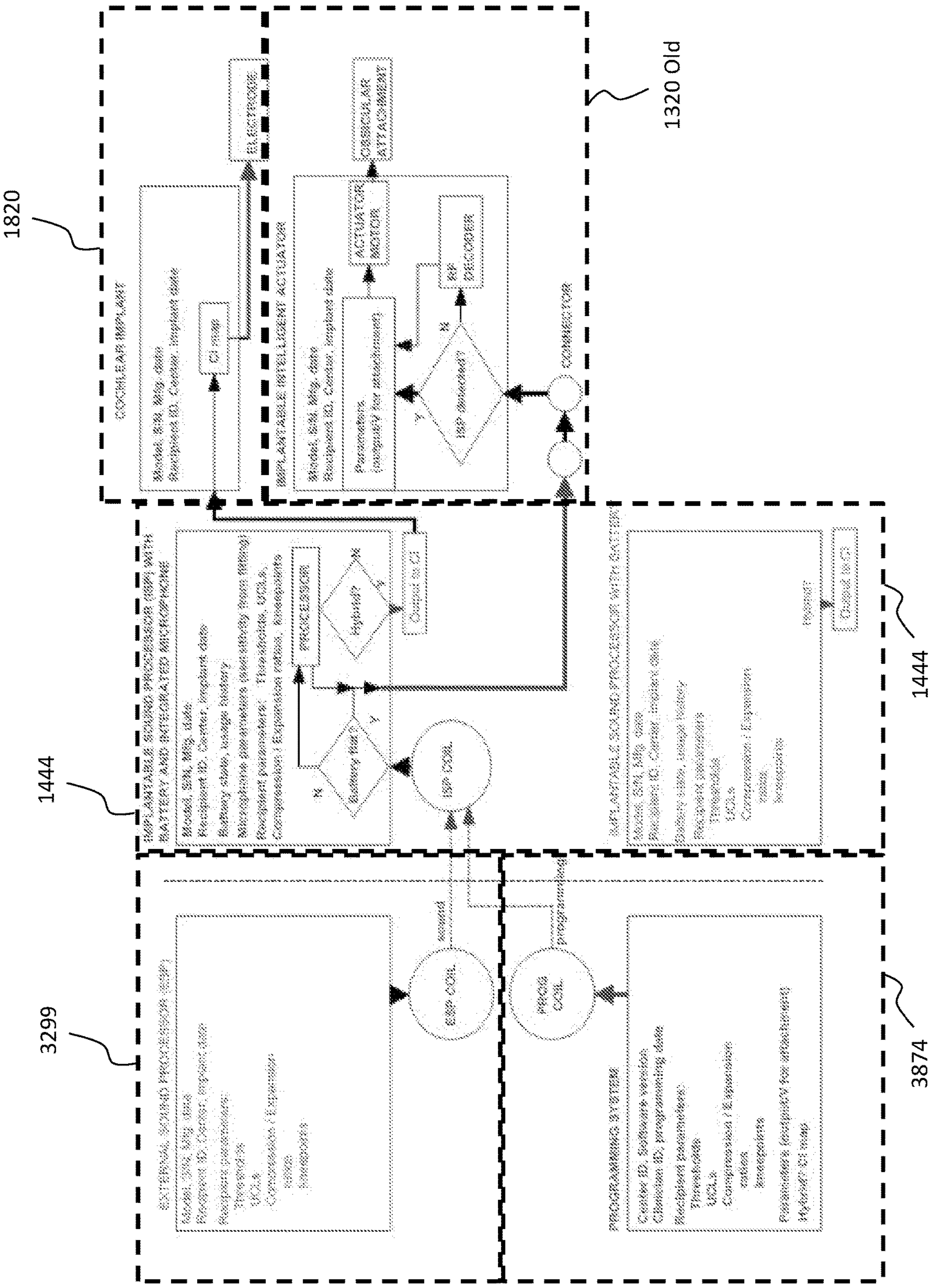
FIG. 39 depicts a functional block diagram of an exemplary system according to an exemplary embodiment with logic details and memory details.

FIG. 39 depicts the introduction of module 3874 into the logic flow of FIG. 37, were module 3299 is also included for frame of reference.

It is noted that while the embodiment of FIG. 35 is the embodiment in which the external programmer is introduced, it is noted that the external programmer can be applicable to any of the other embodiments detailed herein and/or variations thereof, where the external programmer can have different functionality or otherwise be configured to provide different programming information or data for the other modules present in such embodiments.

In view of the above, it is to be understood that at least some exemplary embodiments include an implantable module that is configured to effectively differentiate between other modules placed into signal communication there with. With respect to the above-noted embodiment of the implantable module that has a first functional component, in an exemplary embodiment, the first functional component and implantable speech processor, and the implantable module corresponds to a first module. By way of example only and not by way of limitation, this first module can correspond to module 1444. Still further by way of example, the first module is configured to automatically recognize that the second module has been placed into signal communication with the first module and recognize the second module is a module having a second functionality of a mechanical tissue stimulator. By way of example only and not by way of limitation, this can correspond to module 1320. With respect to an exemplary embodiment where the recipient ultimately upgrades to a hybrid of the like, the implantable module can be configured to automatically recognize that a third module has been placed into signal communication with the first module and recognize that the third module is a module having a third functionality of an electric tissue stimulator. By way of example, such can correspond to module 1820. In an exemplary embodiment, the first module (e.g., module 1444) is configured to automatically adjust an operating regime of at least one of the second module of the third module based on the automatic recognition. By way of example only and not by way of limitation, in a scenario where the implantable prosthesis is upgraded to a hybrid, the adjustments of the operating regime could be the adjustment to that of module 1320 such that module 1320 only stimulates at the lower frequencies whereas prior to the adjustments, module 1320 stimulated at all frequencies (low, medium and high frequencies). Corollary to this is that in an exemplary embodiment, the adjustment of the operating regime of the second module of the third module is one that reduces the operational range thereof. Again, in a scenario where recipient is losing his or her high frequency hearing with respect to mechanical stimulation of the cochlea or other tissue, and the third module is a module of a cochlear implant electrode array, the second module would no longer have the operational range across as much of the frequency spectrum as that which was the case prior to the implantation. Corollary to this is that in an exemplary embodiment, the operating regime of the other of the second module of the third module (e.g., in this embodiment, module 1820) is one that was encompassed at least in part by the operating regime of the second module prior to the reduction of the operational range. Again with respect to the embodiment where the module 1820 is provided to provide stimulation of the high frequency ranges, module 1820 thus operates in a range that was previously encompassed by that of module 1320.

Continuing with respect to the above-noted embodiment of the implantable module that has a first functional component, in an exemplary embodiment, the first functional component is one of a mechanical tissue stimulator (e.g., a middle ear actuator) or an electric tissue stimulator (e.g., a cochlear implant electrode array). In at least some exemplary embodiments, the implantable module can correspond to a first module, and this implantable module is configured to automatically recognize that a second module has been placed into signal communication with the first module and recognize that the second module is a module having a functionality corresponding to the other of a mechanical tissue stimulator or an electric tissue stimulator. In an exemplary embodiment, with respect to the aforementioned upgrade to the hybrid devices via the addition of module 1820, in an exemplary embodiment, module 1320 (or the pertinent external module, etc.) can be configured to automatically recognize that module 1820 has been placed into signal communication therewith. Module 1320 is configured to recognize that module 1820 has a functionality different from that of module 1320. In this exemplary embodiment, this first module (e.g., module 1320) is configured to automatically adjust an operating regime of the first functional component (e.g. the actuator) based on the automatic recognition of module 1820. That said, in an alternate embodiment, the second module can be configured to automatically adjust an operating regime of the second and functional component thereof based on this automatic recognition.

Still further, in an exemplary embodiment, the adjustment of the operating regime of the first functional component with a section functional component is one that reduces the operating range thereof. For example, whereas the operational range of the module 1320 could have been stimulating at all frequencies, the adjustments of the operating regime could result in stimulation by module 1320 only at low and/or low and middle frequencies. Still further, the operating regime of the other of the first functional component of the second functional component is one that was encompassed by that of the first functional component with a second functional component prior to the reduction of the operating range.

Still with reference to an exemplary embodiment corresponding to a hybrid hearing prosthesis, in an exemplary embodiment, as noted above, there is an exemplary implantable system that includes a first implantable module having a first role in the implantable system, wherein the first implantable module is configured to adopt a second roll automatically upon a changed circumstance. In this exemplary embodiment, the system includes a second module (e.g., 1320) in signal communication with the first module, the second module being an actuator of a mechanical stimulator. The first role of the first module is to receive a first signal based on captured sound having a frequency content including a first frequency content and a second frequency content and provide signals to drive the actuator based on the first signal to evoke a hearing percept at frequencies corresponding to the first frequency content and the second frequency content. In this regard, this can correspond to a scenario where the first module is module 1444 operating in a pre-hybrid mode prior to an upgrade. Still with respect to this exemplary embodiment, the second role can be to receive a second signal based on captured sound having a frequency content including the first frequency content and the second frequency content and provide signals to drive the actuator based on the second signal to evoke a hearing percept at frequencies corresponding to the first frequency content, but not the second frequency content. In this regard, this can correspond to a scenario where the first module is module 1444 operating in the post hybrid upgrade mode, where the module 1444 is bifurcating the frequencies into a component that will be utilized for electrical stimulation via module 1820 and a component that will be utilized for the actuator 1320. Note also that in this exemplary embodiment, the second module can be a so-called standard actuator, such as the actuator of module 1540. Thus, in an exemplary embodiment, the second role can also be to provide signals to drive a cochlear implant based on the second signal to evoke a hearing percept at frequencies corresponding to the second frequency content but not the first frequency content.

Figure 40:
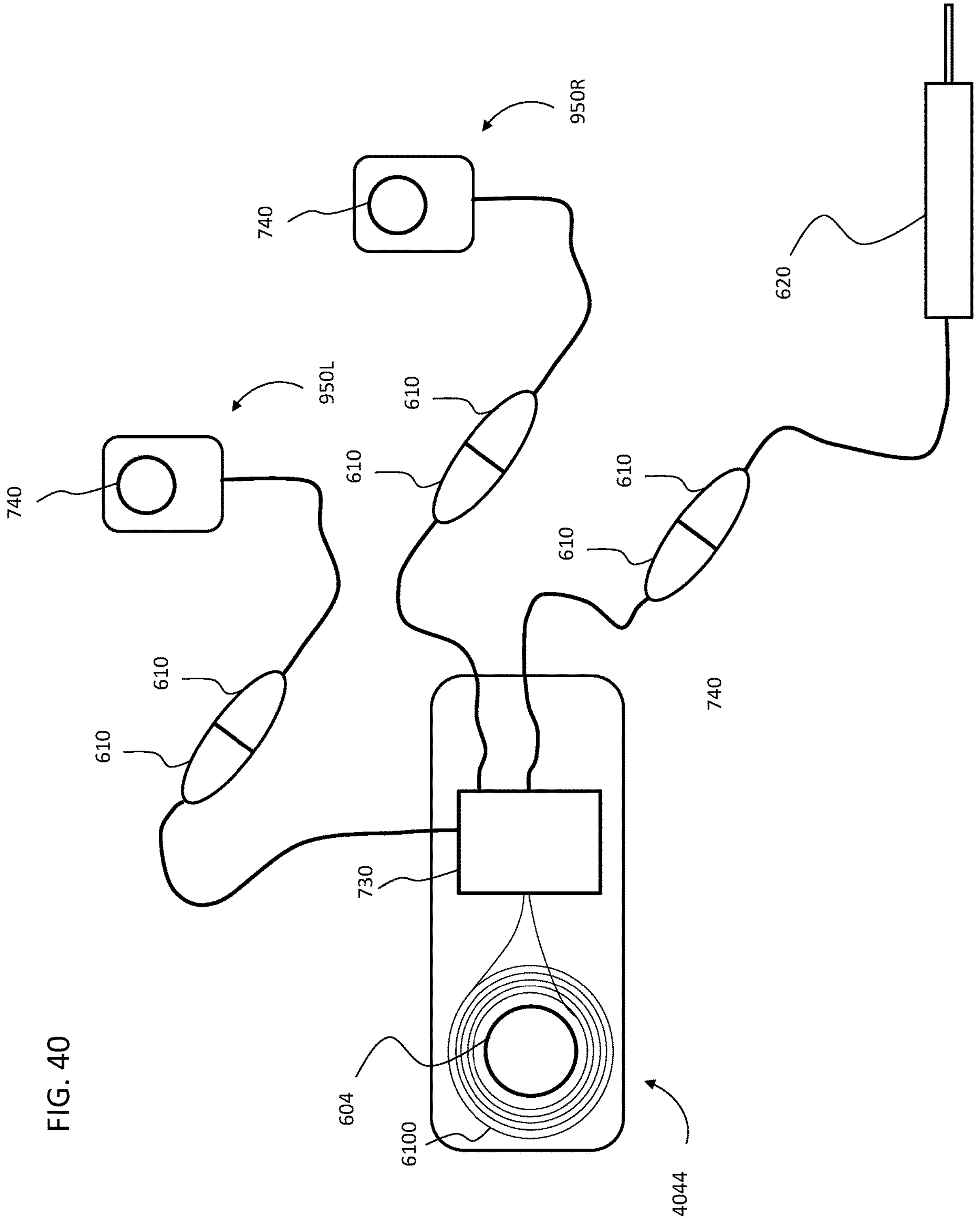
FIG. 40 is a perspective view of an exemplary implantable system according to an exemplary embodiment.
Figure 41:
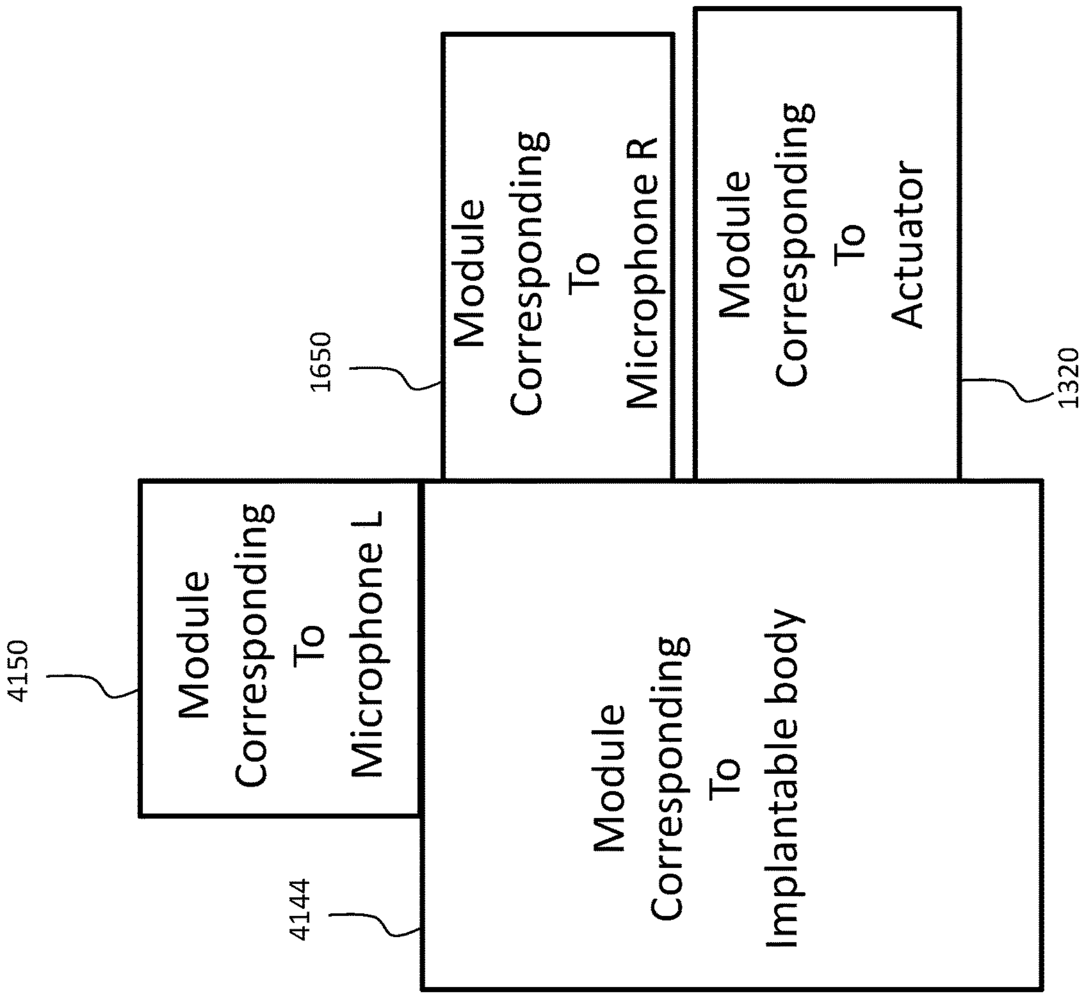
FIG. 41 is a functional block diagram representing an exemplary hearing prostheses according to some of the teachings detailed herein in modularized format.

Note also that the utilitarian teachings detailed herein and/or variations thereof can be also applicable to bilateral implants. In this regard, FIG. 40 depicts an exemplary embodiment of a bilateral hearing prosthesis, having an implantable body 4044 including a sound processor 730 which is in signal communication with three separate connectors 610. The bilateral hearing prosthesis includes two separate pendulum microphones 950L and 950R, each in signal communication with the sound processor 730 via connectors 610. In an exemplary embodiment, microphones 950L and 950R are respectively implanted or otherwise intended to be implanted on the left and right side of the recipient, respectively. Also as can be seen, the intelligent actuator 620 is in signal communication with the sound processor 730. According to the embodiments where such an embodiment is modularized, FIG. 41 depicts module 4144, which corresponds to implantable body 4044, module 1320, which corresponds to the intelligent actuator 630 concomitant with the teachings detailed above, module 1650, which corresponds to microphone 950R, and module 4150, which corresponds to microphone 950L. In an exemplary embodiment, the microphones 950L and 950R are intelligent microphones in that the microphones can vary their output based on changing circumstances or otherwise to accommodate a given implantation regime, etc. In an exemplary embodiment, the microphones 950L and 950R include memory devices, analogous or otherwise the same as that detailed above, in which data is stored.

In an exemplary embodiment, each of the modules 650 and 4150 are initially programmed with information which resides in the memory thereof. In an exemplary embodiment, the memory includes identifying information identifying the microphones as the left side microphone and right side microphone respectively. Still further, in an exemplary embodiment, the memory can include (e.g., in another block thereof) fitting parameters specific to the recipient and the microphone. By way of example only and not by way of limitation, such fitting parameters can include identification of the left or right side, and equalization curve for sensitivity, and/or desired group delay, etc. Any information that has utilitarian value with respect to operating a bilateral prosthesis can be stored in the memory in at least some exemplary embodiments.

In view of the above, it is to be understood that at least some exemplary embodiments include an implantable module that is configured to effectively differentiate between other modules placed into signal communication therewith. With respect to this exemplary embodiment, the aforementioned implantable module can correspond to module 4144, and the functional component can be sound processor 730. The plurality of different second modules mentioned above can be implantable microphones having recorded therein data indicating which side of the recipient the implantable microphones are implanted. The second modules can correspond to modules 1650 and 4150 detailed above. Still further, the implantable module (e.g., module 4144) can be configured to at least one of read the data in the microphones or receive a signal from the microphones with the respective data and adjust operation of the functional component based on the data. In this exemplary embodiment where the functional component is the sound processor, the sound processor will be adjusted so as to take into account the difference in timing between sound being captured on, for example, the left side microphone and sound being captured on for example the right side microphone. In an exemplary embodiment where the actuator module 1320 is implanted such that it provides mechanical stimulation to the recipient's right side cochlea (where such an exemplary embodiment can also include the actuator that includes a memory in which is located data indicating which side of the recipient the actuator is implanted—indeed, in an exemplary embodiment, module 4144 is configured to at least one of read the data in the actuator and/or receive a signal from the actuator indicating which side the actuator is implanted—that said, in an alternative embodiment, the module 4144 is simply programmed with such data), the sound processor can impart a delay with respect to the input from one of the microphones relative to the other so as to provide a more realistic hearing percept vis-à-vis the fact that one ear will naturally hear a sound originating at one side of the recipient relative to another side of the recipient.

In an exemplary embodiment, module 4144 includes a memory unit, concomitant with the other modules with the implantable sound processor detailed above, and the memory can include data corresponding to parameters that take into account the location of the microphones as well as the implanted actuator location. (In this regard, module 1320 can include a memory that includes the implantation side of the actuator (left or right side, etc.)—in an exemplary embodiment, module 4144 is configured to read this memory or otherwise access this memory so as to determine which side the actuator is located on the recipient, and adjust the processing regime of the signal processor accordingly.) In an exemplary embodiment, module 4144 is configured to read the memories of the microphones to determine which microphones are located on which side of the recipient, and adjust the processing regime of the sound processor accordingly.

Figure 42:
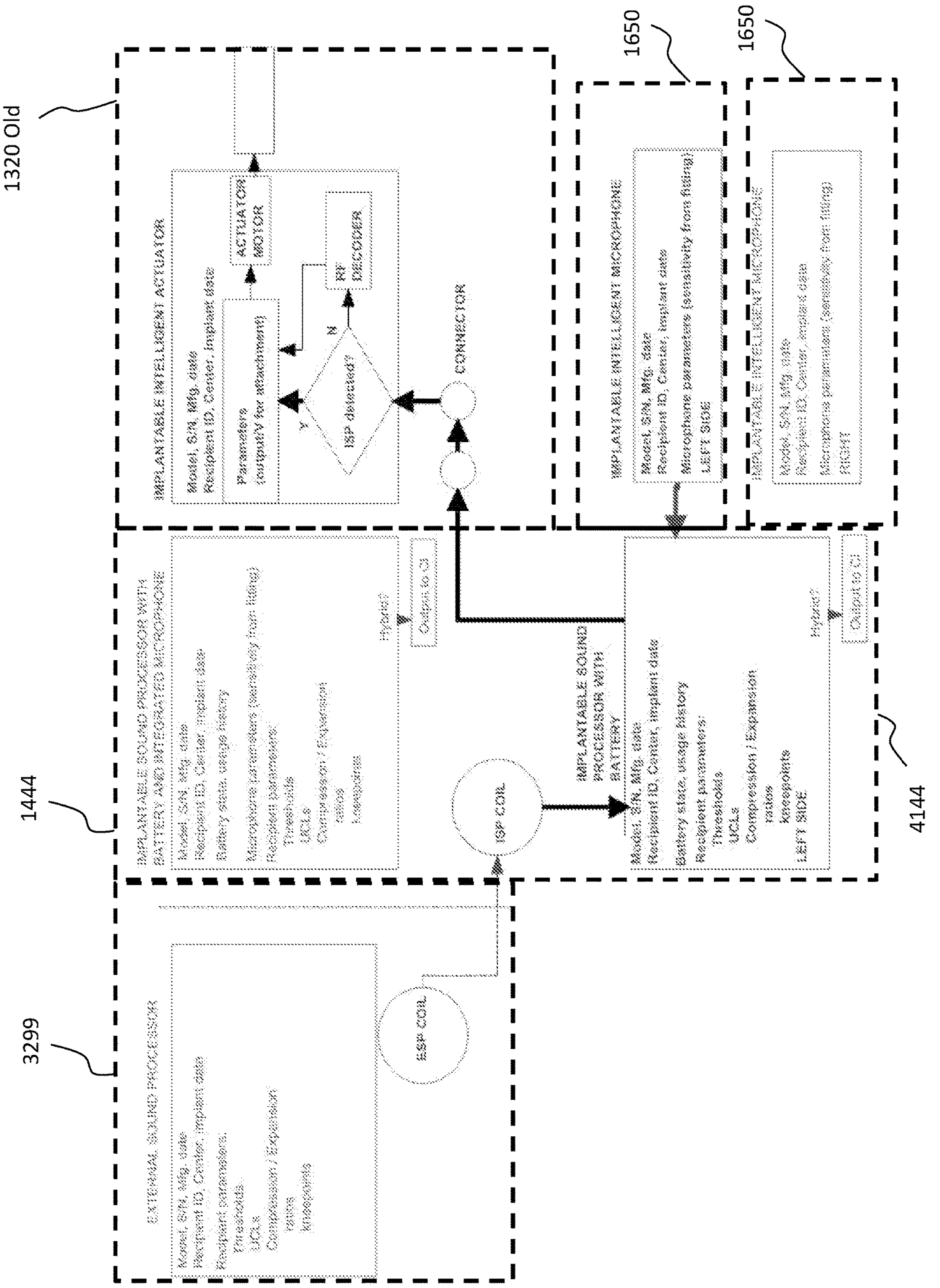
FIG. 42 depicts a functional block diagram of an exemplary system according to an exemplary embodiment with logic details and memory details.

FIG. 42 depicts an illustration of the logical flow assigning functions to the modules of the embodiment of FIG. 41, wherein external sound processor 3299 has been added to that system. Note also that the module 4144 can include data associated with the side on which the implantable sound processor is located. Such can have utilitarian value with respect to evaluating how to process the signals from the left and right microphones. In this regard, if the module 4144 does not know which side is implanted on, the information regarding the fact that a given microphone is implanted on the left or right side may not be utilitarian. Because the memory of the module 4144 includes data relating to the side of the recipient on which is implanted, the module 4144 can evaluate the signals based one such data. Corollary to this is that in an exemplary embodiment, the data stored in the implantable module 4144 can correspond to the side on which the tissue stimulator is implanted. Such can have utilitarian value in that that can have a significant driver on how the signals are processed. Note also that in an exemplary embodiment, module 4144 can include both information relating to the side of the recipient on which the module is implanted, and the side of the recipient on which the tissue stimulator is located. Such can have utilitarian value with respect to a module 4144 that includes an integral microphone (as opposed to a remote microphone) in a manner analogous to the utilitarian value of knowing which sides of the recipient the pendulum microphones are implanted.

Still with reference to an exemplary embodiment corresponding to a bimodal hearing prosthesis, in an exemplary embodiment, as noted above, there is an exemplary implantable system that includes a first implantable module having a first role in the implantable system, wherein the first implantable module is configured to adopt a second roll automatically upon a changed circumstance. In this exemplary embodiment, the first implantable module includes a sound processor, and the first role is a role of a sound processor that processes sound captured by the implantable microphone only on a first side of the recipient. The second role is a role of the sound processor that processes sound captured by an implantable microphone on a second side of the recipient. Note that in this exemplary embodiment, the second role can also include processing sound captured by the implantable microphone on the first side of the recipient.

It is noted that the teachings detailed herein are also applicable to external acoustic hearing aids, whether or not such be part of a hybrid system, such as the embodiment of FIG. 20 detailed above, or as part of a standalone system.

It is noted that some exemplary embodiments of the systems detailed herein are such that sound streaming from an external source can utilize the same communications protocol as that for the external microphone. That said, in some alternate embodiments, a different communications protocol is utilized for streaming sounds than that utilized for the external microphone. Accordingly, by way of example only and not by way of limitation, at least one of the implantable modules is configured to recognize whether or not an external module in signal communication therewith is providing streaming sound data and/or sound data captured from a microphone, and adjust the functionality thereof accordingly. Note also that some exemplary embodiments utilize different frequencies other than the communications frequency to recharge the implantable battery(s). In such an exemplary embodiment, this can enable concurrent charging and sound streaming. Accordingly, an exemplary embodiment can determine whether or not a recharging module or the like is in signal communication with the implanted modules detailed herein and adjust the functionality of such modules accordingly. An exemplary change in the functionality thereof could be adjusting the internal circuitry so as to be receptive to the different frequencies utilized by the battery charger.

Figure 43:
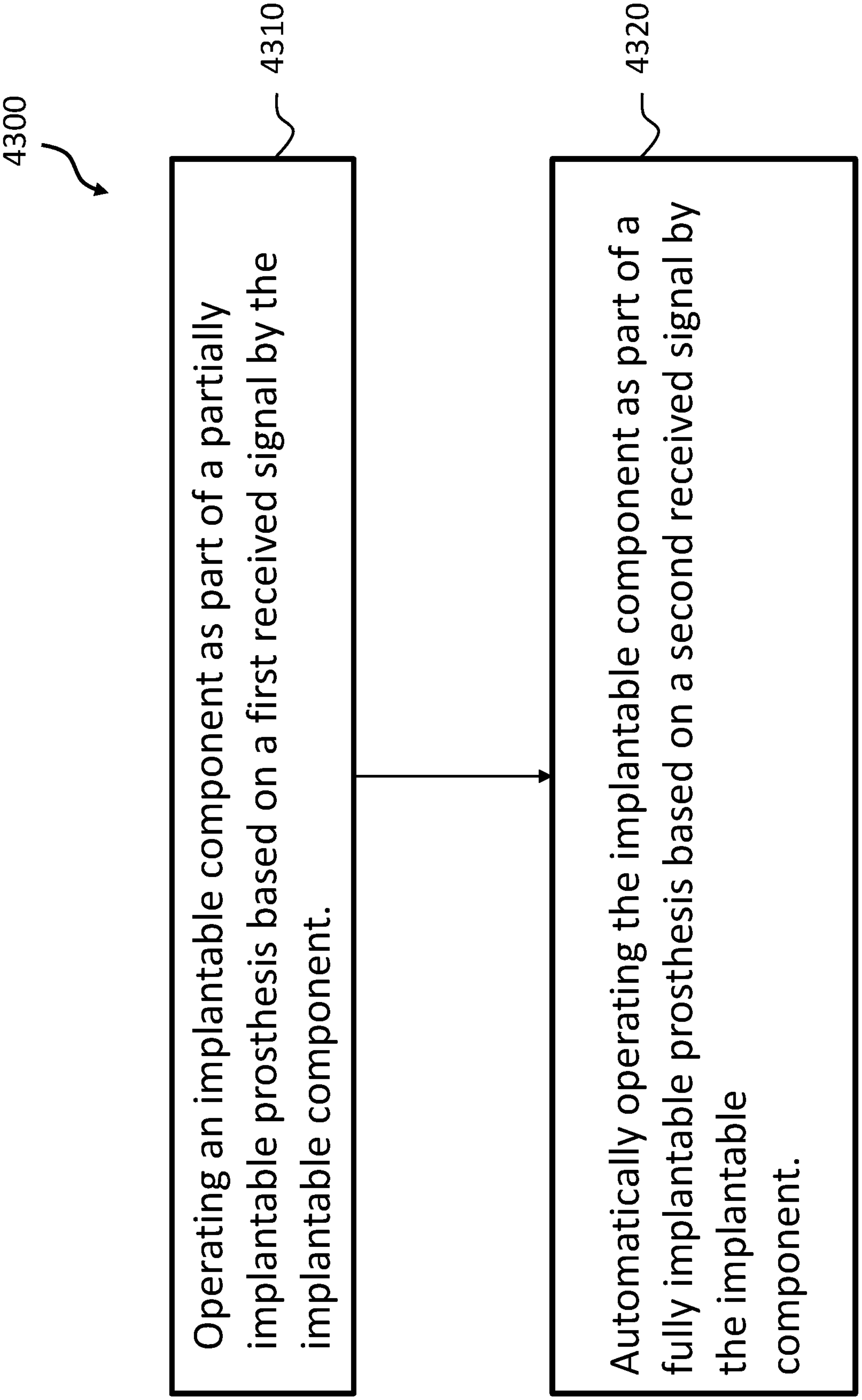
FIG. 43 depicts a flowchart for an exemplary method according to an exemplary embodiment.

In view of the above, it is to be understood that some exemplary embodiments include exemplary methods utilizing the teachings detailed herein. In this regard, FIG. 43 depicts an exemplary flowchart representing method 4300. Method 4300 includes method action 4310, which entails operating an implantable component as part of a partially implantable prosthesis based on a first receive signal by the implantable component. In an exemplary embodiment, this can entail operating the intelligent actuator 620/the module 1320. In an exemplary embodiment, this can entail operating those components as part of the embodiment depicted in FIG. 31. The first received signal can be a signal from the implanted receiver unit 644/module 1344. Still further, method 4300 includes method action 4320, which entails automatically operating the implantable component as part of a fully implantable prosthesis based on a second received signal by the implantable component. In an exemplary embodiment, the second received signal can be a signal sent from the implantable body 744/the module 1444. In this exemplary embodiment, this method action 4320 can occur when the intelligent actuator 620/the module 1320 is part of the system of FIG. 34. In an exemplary embodiment, the automatic operation of the implantable component (e.g., the intelligent actuator) can occur because the intelligent actuator is configured to analyze the output of the module 1444 and determine that it is not an RF signal such as that which would be the case with respect to output from the module 1344 during method action 4310, but instead a signal from a sound processor 730. In an exemplary embodiment, the automatic operation of the implantable component can occur, because the intelligent actuator received a signal (the second signal) from the module 1444 indicating that the module 1320 should operate as part of a fully implantable prosthesis, or at least should operate in a manner where the module 1320 receives stimulation/drive signals and actuates accordingly (e.g., the module 1320 operates in the slave mode noted above). In an exemplary embodiment, the automatic operation of the implantable component can occur because the intelligent actuator received a signal from the module 1444 indicating that the signals provided thereto are provided from an implantable sound processor, and thus logic or otherwise programming in the intelligent actuator is such that the intelligent actuator is configured to reconfigure itself to operate accordingly. Still further, in an exemplary embodiment, the second received signal is a result of an interrogation by the module 1220 of the module 1444 when module 1444 is placed into signal communication with module 1320. For example, the second received signal can be the results of the module 1320 reading the memory of module 1444.

Again, the operation of the implantable component as part of a fully implantable prosthesis occurs automatically based on the second received signal. This is as distinguished from a scenario where the surgeon or the like modifies or otherwise adjusts the operation of the implantable component prior to operation thereof.

In an exemplary embodiment, the action of operating the implantable component as part of a partially implantable prosthesis is executed prior to the action of operating the implantable component is part of a fully implantable prosthesis. In an exemplary embodiment, such a temporal regime corresponds to that which would result from upgrading a partially implantable hearing prosthesis to a fully implantable hearing prosthesis.

Figure 44:
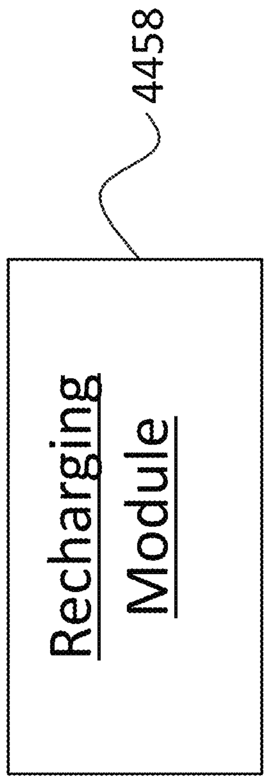
FIG. 44 depicts another flowchart for another exemplary method according to an exemplary embodiment.
Figure 45:
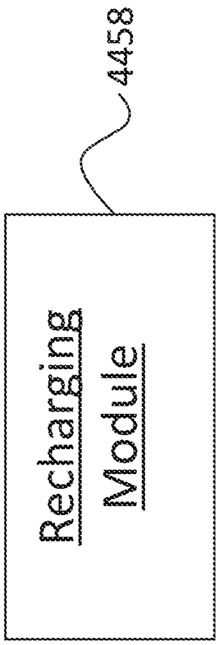
FIG. 45 shows the recharging module 4458.

Referring now to FIG. 44, it can be seen that there is a flowchart for an exemplary method 4400, which includes method action 4410, which entails executing method 4300. Method 4400 further includes method action 4420, which entails, subsequent to the actions of operating the implantable component as part of a fully implantable prosthesis, operating the implantable component as part of a partially implantable prosthesis based on a third received signal by the implantable component. In an exemplary embodiment, such can occur by way of example only and not by way of limitation, as a result of a failure mode and/or a deficiency mode associated with the implantable components of the hearing prosthesis as detailed above (e.g., a failed component, reduced battery power/discharged battery, a recipient desires to utilize an external microphone, etc.). Continuing with the exemplary embodiment where the implantable component is the intelligent actuator 620/the module 1320, such automatic operation can be a result of any of the aforementioned scenarios, albeit in reverse (e.g., the module 1320 receives an RF signal, and module 1320 is configured to recognize that it should operate in the intelligent actuator mode because it is receiving an RF signal; module 1320 receives instructions for module 14442 operate in the intelligent actuator mode, etc.).

Concomitant with the concept of operating the implantable component as part of a partially implantable prosthesis even though the prostheses is configured to operate in the fully implantable mode (albeit circumstances prevent such), in view of the above, it is to be understood that the action of operating the implantable component as part of a partially implantable prosthesis based on the third receive signal can be executed automatically by the implantable component based on an analysis of a state of the system by the implantable component and executed while the structure for a fully implantable prosthesis is implanted in the recipient. This analysis of the state of the system can be based on an analysis of the third signal received by the implantable component. Also concomitant with the exemplary embodiments detailed above, the second received signal can be a signal from a second implantable component (e.g., module 1444) having an implantable microphone (e.g., microphone 740) and/or in signal communication with an implantable microphone (e.g., microphone 950). Still further, the action of operating the implantable component as part of a fully implantable prosthesis is executed automatically upon an analysis of the second received signal by the implantable component.

Still, in an exemplary embodiment, there is any of the methods detailed above and/or below, wherein at least one of: (i) the second implantable component is configured to embed a code in the received signal indicating that the second signal is from a component that enables the implantable component to operate as part of a totally implantable configuration (e.g., module 1444 embeds a signal into a stimulator/driver signal output therefrom); or (ii) the implantable component is configured to extrapolate from the second signal the source thereof and determine that the second signal is from a component that enables the implantable component to operate as part of a totally implantable configuration (e.g., the input to module 1320 is not an RF signal/the input to module 1320 is stimulator/driver signals, and thus the module 1320 recognizes that it should operate in the aforementioned standard mode/slave mode, etc.).

It is noted that in an exemplary embodiment of method action 4300, the implantable component is an implanted sound processor in wired communication with an implanted microphone. In this regard, in an exemplary embodiment, this can be the case where method action 4310 corresponds to the scenario where there is been a failure mode or a deficiency mode where the recipient seeks to utilize an external microphone, etc.

As noted above, there is an exemplary implantable system that includes a first implantable module having a first role in the implantable system, wherein the first implantable module is configured to adopt a second roll automatically upon a changed circumstance. An exemplary embodiment includes a method action comprising surgically implanting at least a portion of the system that includes the first implantable module. In this exemplary method, the first implantable module adopts the second roll automatically during the implantation process upon the establishment of signal communication with a second implantable module. It is noted that by "surgically implanting a system," that action need not include the action of implanting the first implantable module. In this regard, the first implantable module can be already implanted (e.g., such could be the module 1320, etc.).

As detailed above, the various modules include recorded or otherwise stored therein data. It is noted that in an exemplary embodiment, any one or more of the modules detailed herein and/or variations thereof where generic model in general is configured to at least one of transmit at least a portion of the data stored in the memory to another module or enable another module to read at least a portion of the data stored in the memory. In an exemplary embodiment, the data stored in the memory can correspond to any of the data detailed herein and/or variations thereof. In an exemplary embodiment, the system utilizing the innovative modules detailed herein and/or variations thereof utilizes the data so as to reconfigure a given module or otherwise adjust the operation of the given module or otherwise change the role of a given module, etc., according to the teachings detailed herein.

It is noted that any device and/or system detailed herein also corresponds to a disclosure of a method of operating that device and/or using that device. Furthermore, any device and/or system detailed herein also corresponds to a disclosure of manufacturing or otherwise providing that device and/or system. Corollary to this is that any disclosure of a method herein corresponds to a disclosure of a device and/or system of implementing that method and/or a program product for implementing that method on a computer apparatus. Still further, any functionality of any device and/or system detailed herein corresponds to a method of taking action to achieve such functionality.

Any teaching of any embodiment detailed herein can be combined with one or more of other teachings of other embodiments detailed herein, providing that the art enables such, unless otherwise specified. It is further noted that any particular one or more teachings detailed herein can be omitted from an embodiment when implementing some exemplary embodiments. To be clear, any feature detailed herein can be combined with any other feature detailed herein unless otherwise noted, and/or unless the prior art does not enable such.

While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. A method comprising:

operating an implantable component as part of a partially implantable prosthesis based on a first received signal received by the implantable component;

automatically operating the implantable component as at least part of a fully implantable prosthesis based on a change in input to the implantable component, wherein when operating the implantable component as at least part of the fully implantable prosthesis, all sound capture executed to evoke a hearing percept by the implantable component is executed without the use of a non-implanted device; and operating an external component of a hearing prosthesis, while worn on a recipient of the implantable component, to capture sound, process the captured sound and communicate radio frequency signals to the implantable component based on the processed sound while the implantable component operates as part of a partially implantable prosthesis so that the implantable component can evoke a hearing percept and while a power storage device that powers the implantable component is being recharged by the external component, wherein the implantable component is configured to determine whether or not a recharging module is in signal communication with the implantable component and adjust a functionality of the implantable component based on the determination, the method further comprises obtaining the recharging module and transcutaneously recharging the power storage device, wherein the recharging module is a separate and different device from the external component, and the method further comprises:

subsequent to the actions of operating the implantable component as part of a fully implantable prosthesis and as part of a partially implantable prosthesis, automatically operating the implantable component as part of a partially implantable prosthesis while the power storage device is being recharged by the external component and while the external component is providing encoded data signals to the implantable component, which encoded data signals are based on processed output from a microphone of the external component processed by a sound processing unit of the external component.

2. The method of claim 1, wherein:

the action of operating the implantable component as part of a partially implantable prosthesis is executed prior to the action of operating the implantable component as at least part of a fully implantable prostheses.

3. The method of claim 2, wherein:

the action operating the implantable component as part of a partially implantable prosthesis is based on a second received signal received by the implantable component and is executed automatically by the implantable component based on an analysis of a state of the system by the implantable component and executed while the structure for a fully implantable hearing prosthesis is implanted in a recipient of the implantable component.

4. The method of claim 1, wherein:

the action of operating the implantable component as part of a partially implantable prosthesis is executed after the action of operating the implantable component as part of a fully implantable prosthesis.

5. The method of claim 1, wherein:

the action of operating the implantable component as part of a partially implantable prosthesis is executed after the action of operating the implantable component as at least part of a fully implantable hearing prosthesis, and the action of operating the implantable component as part of a partially implantable prosthesis is executed as a result of a determination that the power storage device of the implantable component has a low or depleted charge, the action of operating the implantable component as part of a partially implantable prosthesis enabling the implantable component to continue to evoke hearing percepts even though the power storage device has a low and/or depleted charge relative to that which would otherwise have been the case.

6. The method of claim 1, wherein the external component includes:

an RF transmitter configured to execute the action of communicating the radio frequency signals to the implantable component.

7. The method of claim 1, wherein:

the change in input is a second received signal received by the implantable component.

8. The method of claim 1, wherein:

the action of automatically operating the implantable component as at least part of a fully implantable prostheses is executed because the power storage device has been recharged from the discharged state, and the action of operating the implantable component as part of a partially implantable prosthesis occurs before the action of automatically operating the implantable component as at least part of a fully implantable prosthesis.

9. The method of claim 1, wherein the external component is a behind-the-ear (BTE) device.

10. The method of claim 1, wherein:

the implantable component includes an inductance coil; and the method further comprises capturing sound with a remote microphone unit separate from the implantable component and separate from the external component and providing a signal based on the captured sound to the implantable component.

11. A system, comprising:

a first implantable module having a first role in the system, wherein the first implantable module is configured to adopt a second role automatically upon a changed circumstance, the second role is that of a component of a partially implantable hearing prosthesis, the first role is that of a component of a totally implantable hearing prosthesis, wherein when operating in the role of a totally implantable hearing prosthesis, all sound capture executed to evoke a hearing percept using the first implantable module is executed using only implantable device(s);

the first implantable module is part of an implantable assembly that is configured to determine whether or not a recharging module is in signal communication with the implantable assembly and adjust a functionality of the implantable assembly based on the determination, the system includes an external device including a processor, the external device being configured to control the first implantable module when the first implantable module adopts the second role so that the implantable assembly evokes a hearing percept based on data from the external device, the system includes the recharging module, the system is configured so that a sound processor of the implantable assembly does not process sound when the implantable assembly is functioning in the second role;

the system is a modular cochlear implant system including a cochlear implant electrode array and a stimulator in electrical communication with the array;

the sound processor of the implantable assembly is in signal communication with the stimulator and an implantable microphone in signal communication with the sound processor of the implantable assembly, wherein the sound processor of the implantable assembly is in a separate module from a module in which the stimulator is located;

the system includes a connector configured to detachably connect the sound processor of the implantable assembly and the implantable microphone and to provide communication between sound processor of the implantable assembly and the implantable microphone when attached;

the sound processor of the implantable assembly is configured to receive an input signal from the implantable microphone and output a signal to the stimulator based on the received input signal;

the stimulator is configured to provide an electrical signal to the array based on the signal outputted to the stimulator by the sound processor of the implantable assembly; and at least one of the sound processor of the implantable assembly or the stimulator is part of the first implantable module.

12. The system of claim 11, wherein:

the system includes a second module, wherein the second module has a functionality of a tissue stimulator, the second module being part of the implantable assembly;

the first role is also that of a sound processor that receives a sound signal from a microphone in communication with the sound processor and outputs a first control signal to the second module which is in signal communication with the first module to cause the second module to stimulate tissue based on the first control signal; and the second role is also that of at least one of:

- a device that receives a signal from an external module external to a recipient of the implantable component and provides a stimulator control signal based on the received signal to activate the second module to stimulate tissue; or
- a pass-through device that receives the signal from the external module external to the recipient and provides the signal to the second module to activate the second module to stimulate tissue based on the received signal.

13. The system of claim 11, wherein:

the first implantable module includes the sound processor of the implantable assembly and the first role is also as a sound processor role which processes sound as at least part of the totally implantable hearing prosthesis; and the changed circumstance is a low charge of an implanted power storage device of the system, wherein the power storage device powers the sound processor.

14. The system of claim 13, wherein:

the second role is also a pass-through role which is different from the sound processor role.

15. The system of claim 11, wherein:

the external device is configured to capture sound and process sound and output a signal that is transmitted transcutaneously to the implantable assembly, wherein the implantable assembly is configured to receive the signal that is transmitted transcutaneously and evoke a hearing percept based thereon when the first implantable module is in the second role.

16. The system of claim 15, wherein:

the external device is also configured to recharge the implantable assembly.

17. A system, comprising:

an implantable component including a sound processor, a microphone, a tissue stimulating device and a power storage device, wherein the implantable component is configured to variously function as a totally implantable hearing prosthesis to evoke a hearing percept using only components that are implanted in a recipient of the system and a partially implantable hearing prosthesis; and an external component including a sound processor and a microphone, wherein the implantable component is configured to function as the totally implantable hearing prosthesis and function as the partially implantable hearing prosthesis upon the occurrence of different scenarios, the external component is configured to provide power content signals and sound content signals to variously recharge the power storage device of the implantable component and to enable the implantable component to stimulate tissue to evoke a hearing percept while the power content signals are being provided to the implantable component and the power storage device is being recharged based on the power content signals, the implantable component is configured to receive the power content signals and sound content signals to variously recharge the power storage device of the implantable component and to stimulate tissue to evoke a hearing percept while the power content signals are being received by the implantable component and the power storage device is being recharged based on the power content signals, the implantable component is configured to determine whether or not a recharging module is in signal communication with the implantable component and adjust a functionality of the implantable component based on the determination so that the implantable component functions as the totally implantable hearing prosthesis instead of the partially implantable hearing prosthesis, the system includes an external recharging device separate from the external component, the recharging module being at least part of the external recharging device, and the implantable component is configured to automatically transition to function as the totally implantable hearing prosthesis from functioning as the partially implantable hearing prosthesis.

18. The system of claim 17, wherein:

the implantable component is configured to automatically identify at least one of:

a first scenario where the implantable component cannot operate as a totally implantable hearing prosthesis; or a second scenario where the implantable component soon will not be able to operate as a totally implantable hearing prosthesis; and the implantable component is configured to automatically transition to function as a partially implantable hearing prosthesis from functioning as a totally implantable hearing prosthesis upon the identification of the first scenario and/or upon the identification of the second scenario.

19. The system of claim 17, wherein:

the system is configured so that the sound processor of the implantable component does not process sound when the implantable component is functioning as the partially implantable hearing prosthesis.

20. The system of claim 17, further comprising:

an implantable microphone module including a second microphone in signal communication with the implantable component so that the system includes two implantable microphones corresponding to the microphone of the implantable component and the second microphone.

* * * * *